US012746202B2

(12) United States Patent
Tamada et al.

(10) Patent No.: US 12,746,202 B2
(45) Date of Patent: Sep. 29, 2026

(54) CATIONIC LIPID HAVING DISULFIDE BOND, LIPID MEMBRANE STRUCTURE INCLUDING SAME, NUCLEIC ACID INTRODUCTION AGENT AND PHARMACEUTICAL COMPOSITION CONTAINING ANY ONE OF SAME, METHOD FOR INTRODUCING NUCLEIC ACID INTO CELL OR TARGET CELL, AND METHOD FOR PRODUCING CELLULAR PHARMACEUTICAL

(71) Applicants: NOF Corporation, Tokyo (JP); National University Corporation Chiba University, Chiba (JP)

(72) Inventors: Masamichi Tamada, Kawasaki (JP); Tokihiro Tanaka, Kawasaki (JP); Shinya Tamagawa, Kawasaki (JP); Kota Tange, Kawasaki (JP); Yuta Nakai, Kawasaki (JP); Kasumi Ito, Kawasaki (JP); Hidetaka Akita, Chiba (JP); Hiroki Tanaka, Chiba (JP); Yu Sakurai, Chiba (JP); Yuka Sato, Chiba Chiba (JP)

(73) Assignees: NOF Corporation, Tokyo (JP); National University Corporation Chiba University, Chiba (JP)

(*) Notice: Subject to any disclaimer, the term of this patent is extended or adjusted under 35 U.S.C. 154(b) by 133 days.

(21) Appl. No.: 18/852,405

(22) PCT Filed: Mar. 24, 2023

(86) PCT No.: PCT/JP2023/011839
§ 371 (c)(1),
(2) Date: Sep. 27, 2024

(87) PCT Pub. No.: WO2023/190166
PCT Pub. Date: Oct. 5, 2023

(65) Prior Publication Data

US 2025/0213478 A1 Jul. 3, 2025

(30) Foreign Application Priority Data

Mar. 28, 2022 (JP) ................................ 2022-051912

(51) Int. Cl.

| | |
|---|---|
| ***A61K 9/127*** | (2025.01) |
| ***A61K 9/1272*** | (2025.01) |
| ***A61K 9/51*** | (2006.01) |
| ***A61K 48/00*** | (2006.01) |
| ***C07C 323/12*** | (2006.01) |
| ***C07C 323/25*** | (2006.01) |
| ***C07C 323/41*** | (2006.01) |

(Continued)

(52) U.S. Cl.
CPC .......... *A61K 9/1272* (2013.01); *A61K 9/5123* (2013.01); *A61K 48/0033* (2013.01); *C07C 323/12* (2013.01); *C07C 323/25* (2013.01); *C07C 323/41* (2013.01); *C07D 211/14* (2013.01); *C12N 15/88* (2013.01)

(58) Field of Classification Search
None
See application file for complete search history.

(56) References Cited

U.S. PATENT DOCUMENTS

| | | | | |
|---|---|---|---|---|
| 9,708,628 | B2 | 7/2017 | Tange et al. | |
| 2014/0335157 | A1* | 11/2014 | Tange .................... | A61K 47/20 546/196 |
| 2018/0155304 | A1 | 6/2018 | Nakai et al. | |
| 2021/0023008 | A1 | 1/2021 | Nakai et al. | |
| 2023/0127080 | A1 | 4/2023 | Tamagawa et al. | |

FOREIGN PATENT DOCUMENTS

| | | | |
|---|---|---|---|
| WO | WO 2013/073480 | A1 | 5/2013 |
| WO | WO 2016/121942 | A1 | 8/2016 |
| WO | WO 2019/188867 | A1 | 10/2019 |
| WO | WO 2021/193397 | A1 | 9/2021 |
| WO | WO 2022/016089 | A2 | 1/2022 |
| WO | WO 2022/016089 | A3 | 1/2022 |

OTHER PUBLICATIONS

Puchkov et al., ChemistrySelect, 2020, vol. 5, 4509-4514. (Year: 2020).*
Akita, "Development of Intracellular Environment-responsive Lipid Like Material for the Nucleic Acid Delivery," *Medchem News*, 30(1): 30-36 (2020).

(Continued)

*Primary Examiner* — Brian Gulledge
(74) *Attorney, Agent, or Firm* — Leydig, Voit & Mayer, Ltd.

(57) ABSTRACT

The present invention provides a cationic lipid that can be used as a nucleic acid delivery carrier with good intracellular dynamics, a lipid membrane structure containing the same, a nucleic acid-introducing agent and a pharmaceutical composition containing any of them, a method for introducing nucleic acid into cells or target cells, and a method for producing a cell medicine. A cationic lipid represented by the formula (1) (definitions of symbols in the formula are as described in the specification), a lipid membrane structure using the aforementioned cationic lipid, a nucleic acid-introducing agent and a pharmaceutical composition using the aforementioned cationic lipid or the aforementioned lipid membrane structure, a method for introducing nucleic acid into cells or target cells by using the aforementioned nucleic acid-introducing agent, and a method for producing a cell medicine by using the aforementioned nucleic acid-introducing agent.

$$X\text{—}(R^1\text{—}L^1)_k\text{—}R^x\text{—}S\text{—}S\text{—}R^y\text{—}L^2\text{—}R^2\text{—}Y \quad (1)$$

20 Claims, No Drawings

(51) Int. Cl.
*C07D 211/14* (2006.01)
*C12N 15/88* (2006.01)

(56) References Cited

OTHER PUBLICATIONS

Hama et al., "Quantitative Comparison of Intracellular Trafficking and Nuclear Transcription between Adenoviral and Lipoplex Systems," *Mol. Ther.*, 13(4): 786-794 (2006).
Jayaraman et al., "Maximizing the Potency of siRNA Lipid Nanoparticles for Hepatic Gene Silencing In Vivo," *Angew. Chem. Int. Ed.*, 51(34): 8529-8533 (2012).
Morille et al., "Progress in Developing Cationic Systems for Non-Viral Vector Systemic Gene Therapy against Cancer," *Biomaterials*, 29(24-25): 3477-3496 (2008).
Sato et al., "Relationship Between the Physicochemical Properties of Lipid Nanoparticles and the Quality of siRNA Delivery to Liver Cells," *Mol. Ther.*, 24(4): 788-795 (2016).
Japan Patent Office, International Search Report in International Patent Application No. PCT/JP2023/011839 (Jun. 13, 2023).
Japan Patent Office, Written Opinion of the International Searching Authority in International Patent Application No. PCT/JP2023/011839 (Jun. 13, 2023).

* cited by examiner

CATIONIC LIPID HAVING DISULFIDE BOND, LIPID MEMBRANE STRUCTURE INCLUDING SAME, NUCLEIC ACID INTRODUCTION AGENT AND PHARMACEUTICAL COMPOSITION CONTAINING ANY ONE OF SAME, METHOD FOR INTRODUCING NUCLEIC ACID INTO CELL OR TARGET CELL, AND METHOD FOR PRODUCING CELLULAR PHARMACEUTICAL

TECHNICAL FIELD

The present invention relates to a cationic lipid having a disulfide bond, a lipid membrane structure containing same, a nucleic acid-introducing agent and a pharmaceutical composition containing any of these, a method for introducing nucleic acid into a cell or a target cell, and a method for producing a cell medicine.

BACKGROUND ART

For practicalization of nucleic acid therapy, an effective and safe nucleic acid delivery carrier is demanded. While virus vectors are nucleic acid delivery carriers with good expression efficiency, the development of non-viral nucleic acid delivery carriers that can be used more safely is ongoing. Among them, carriers using a cationic lipid are non-viral nucleic acid delivery carriers most generally used at present.

Cationic lipids are largely composed of an amine moiety and a lipid moiety. In cationic lipids, the amine moiety showing cationicity and a polyanion nucleic acid electrostatically interact to form a liposome or lipid membrane structure, which promotes uptake into cells and delivers the nucleic acid into cells.

As known cationic lipids generally and widely used, 1,2-dioleoyloxy-3-trimethylammonium propane (DOTAP) and 1,2 -dioleoyloxy-3-dimethylaminopropane (DODAP) can be mentioned. These known cationic lipids form a positively-charged liposome or lipid membrane structure when combined with a phospholipid, which electrostatically interacts with a nucleic acid to be able to deliver the nucleic acid to the target cells (see, for example, non-Patent Literature 1).

On the other hand, for a lipid membrane structure using a cationic lipid to exhibit a practical effect in vivo as a nucleic acid delivery carrier, good pharmacokinetics are required. Specifically, high stability in blood, property to highly accumulate in the target tissues such as liver, tumor, and the like need to be fulfilled. As regards this problem, it is known that a lipid membrane structure having a surface pKa adjusted to near neutral and having a PEG lipid introduced therein exhibits a long life in the blood after intravenous injection and accumulates at the tumor site. Furthermore, there are examples where pharmacokinetics were improved by adjusting surface pKa of lipid membrane structures.

For example, Non Patent Literature 2 and Non Patent Literature 3 show that pharmacokinetics and distribution in each cell in the liver can be controlled by adjusting the surface pKa of lipid membrane structures. These literatures show that escape of lipid membrane structures from endosomes is promoted and nucleic acids can be efficiently delivered into the cytoplasm by adjusting the pKa of lipid membrane structures to a value for endosome escape.

CITATION LIST

Patent Literature

[Patent Literature 1]
U.S. Pat. No. 9,708,628
[Patent Literature 2]
WO 2016/121942
[Patent Literature 3]
WO 2019/188867
[Patent Literature 4]
WO 2021/193397

Non Patent Literature

[Non Patent Literature 1]
Biomaterials 29(24-25):3477-96, 2008
[Non Patent Literature 2]
Molecular Therapy 24(4):788-795, 2016
[Non Patent Literature 3]
Angewante Chemie International Edition 51:8529-8533, 2012
[Non Patent Literature 4]
Molecular Therapy 13(4):786-794, 2006

SUMMARY OF INVENTION

Technical Problem

While cationic lipids having improved pharmacokinetics have been developed as shown above, in view of the property of the nucleic acid delivery carriers that they generally introduce exogenous substances into cells, a large effect output from a small uptake amount is desired. That is, when a lipid membrane structure is used as a delivery carrier of an expression vector into cells, it is desired to increase the expression level per unit lipid membrane structure incorporated into the cells and enhance intracellular expression efficiency. To enhance the intracellular expression efficiency, it is necessary to also improve, besides pharmacokinetics, intracellular kinetics such as uptake process into cells, escape from endosome, nuclear membrane permeation, and the like (see, for example, non-Patent Literature 4).

In order to improve expression efficiency, there are methods to impart biodegradability to cationic lipids (see, for example, Patent Literatures 1 to 4). These patent literatures show a cationic lipid having a structure linked by a biodegradable disulfide bond. These literatures show that the cationic lipid can improve intracellular dynamics by dissociating nucleic acid from a lipid membrane structure by utilizing intracellular cleavage of a disulfide bond. Such cationic lipids show high nucleic acid delivery efficiency, compared to DOTAP and DODAP which are known cationic lipids. That is, it has been clarified that the cationic lipids described in Patent Literatures 1 to 4 can improve intracellular dynamics such as improvement of delivery efficiency of nucleic acid into the cytoplasm and the like. Furthermore, the effect of reducing toxicity is expected by imparting degradability.

However, nucleic acid therapy targets a wide variety of diseases. In order to establish a treatment method suitable for each disease, it is desired to further improve intracellular dynamics.

In view of the above-mentioned problem, the present invention aims to provide a cationic lipid that can be used as a nucleic acid delivery carrier with good intracellular dynamics, a lipid membrane structure containing the same, a nucleic acid-introducing agent and a pharmaceutical composition containing any of them, a method for introducing nucleic acid into cells or target cells, and a method for producing a cell medicine.

Solution to Problem

In view of the above-mentioned problems, the present inventors have conducted intensive studies and found that the cationic lipid represented by the following formula (1) can efficiently deliver nucleic acid to a target cell. Specifically, the cationic lipid represented by the following formula (1) is an asymmetric cationic lipid having a lipid moiety containing an aromatic ring and an amine moiety introduced via a disulfide bond. Since the disulfide bond is cleaved in cells, it also affords an effect of dissociating a nucleic acid from a lipid membrane structure. In addition, they have found that a lipid membrane structure containing the novel cationic lipid can deliver nucleic acid efficiently into the cytoplasm.

Accordingly, the present invention includes the following.

[1]A cationic lipid having a disulfide bond represented by the formula (1):

$$X-(R^1-L^1)_k-R^x-S-S-R^y-L^2-R^2-Y \quad (1)$$

wherein

X is a nitrogen-containing aliphatic group containing one or more tertiary nitrogens, $R^1$ is an aliphatic hydrocarbon group having not more than 8 carbon atoms, $L^1$ is an ester bond, an amide bond, a carbanate bond, an N-alkylcarbamate bond, a carbonate bond or a urea bond, k is 0 or 1, $R^x$ and $R^y$ are each independently an alkylene group having 2-5 carbon atoms, $L^2$ is an ester bond, an amide bond, a carbamate bond, a carbonate bond, an ether bond or a urea bond, $R^2$ is an alkylene group having not more than 8 carbon atoms, or absent, and Y is a group which (i) contains one or more divalent groups derived from an aromatic compound optionally having a hetero atom, (ii) contains a group containing at least one selected from the group consisting of an ester bond and a carbonate bond on the aromatic ring of the aforementioned divalent group, and (iii) contains at least one selected from the group consisting of an aliphatic hydrocarbon group having 10-37 carbon atoms, a liposoluble vitamin residue, and a residue of a sterol derivative.

[2] The cationic lipid having a disulfide bond of [1], wherein

X is a group represented by the formula (2):

$$R^{\alpha}-N(R^{\beta})- \quad (2)$$

wherein $R^{\alpha}$ is an aliphatic hydrocarbon group, and $R^{\beta}$ is an aliphatic hydrocarbon group, an aliphatic group containing one or more hetero atoms other than nitrogen, or an aliphatic group containing one or more tertiary amines, or $R^{\alpha}$ and $R^{\beta}$ are optionally bonded to form a 3- to 8-membered nitrogen-containing alicyclic ring.

[3] The cationic lipid having a disulfide bond of [1], wherein

X is a dialkylamino group (wherein the two alkyl groups of the dialkylamino group each independently have 1 to 8 carbon atoms), a 3- to 6-membered cyclic amino group optionally having a hetero atom, or $-N(R^a)-R^b$, $R^a$ is an alkyl group having 1-8 carbon atoms, $R^b$ is $-(CH_2)q-O-R^c$, $R^c$ is a hydrogen or an alkyl group having 1-8 carbon atoms, and q is an integer of 2 to 4.

[4] The cationic lipid having a disulfide bond of any one of [1] to [3], wherein $R^1$ is an alkylene group having not more than 8 carbon atoms, or an alkenylene group having not more than 8 carbon atoms.

[5] The cationic lipid having a disulfide bond of any one of [1] to [4], wherein Y is a group represented by the formula (3):

(3)

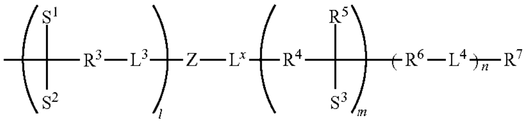

wherein $R^3$ is an alkylene group having not more than 8 carbon atoms, $L^3$ is an ester bond or a carbonate bond, $S^1$ is a hydrogen, an alkyl group having 1-8 carbon atoms, $-R^e-L^a-R^{7'}$, or $-R^e-L^a-Z'-L^b-R^{7'}$, $S^2$ is $-R^{e'}-L^a-R^{7'}1$ or $-R^{e'}-L^a-Z'-L^b-R^{7''}$, $R^e$ and $R^{e'}$ are each independently an alkylene group having not more than 8 carbon atoms, $L^a$ is an ester bond or a carbonate bond, $L^b$ is an ester bond or a carbonate bond, 1 is 0 or 1, Z, Z' and Z" are each independently a divalent group derived from an aromatic compound having 3-16 carbon atoms and at least one aromatic ring, and optionally having a hetero atom, $L^x$ is an ester bond or a carbonate bond, $R^4$ is an alkylene group having not more than 8 carbon atoms, or absent, $R^5$ is a hydrogen or an alkyl group having 1-8 carbon atoms, $S^3$ is $-R^{6'}-L^{4'}-R^{7'''}$, m is 0 or 1, $R^6$ and $R^{6'}$ are each independently an alkylene group having not more than 8 carbon atoms, or absent, $L^4$ and $L^{4'}$ are each independently an ester bond or a carbonate bond, $R^7$, $R^{7'}$, $R^{7''}$ and $R^{7'''}$ are each independently an aliphatic hydrocarbon group having 10-37 carbon atoms, or $-(CH_2)p-C(=O)-R^f$, $R^f$ is a residue of a liposoluble vitamin having a hydroxyl group or a residue of a sterol derivative having a hydroxyl group, and p is 2 or 3, and n is 0 or 1.

[6] The cationic lipid having a disulfide bond of any one of [1] to [5], wherein Z, Z' and Z" are each a group represented by the formula (4):

(4)

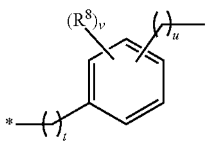

wherein t is an integer of 0 to 3, u is an integer of 0 to 3, v is an integer of 0 to 4, and $R^8$ in the number of v are each independently a substituent, and is the bonding position with $L^3$ or $L^a$.

[7] The cationic lipid having a disulfide bond of any one of [1] to [6], wherein $R^x$ and $R^y$ are each an ethylene group.

[8] The cationic lipid having a disulfide bond of any one of [1] to [7], wherein $R^7$, $R^{7'}$, $R^{7''}$ and $R^{7'''}$ are each independently an aliphatic hydrocarbon group having 10 to 37 carbon atoms, or $-(CH_2)_2-C(=O)-R^f$, and $R^f$ is a residue of a liposoluble vitamin having a hydroxyl group.

[9]A lipid membrane structure comprising the cationic lipid having a disulfide bond of any one of [1] to [8] as a constituent lipid of a membrane.

[10]A lipid membrane structure comprising the cationic lipid having a disulfide bond of any one of [1] to [8] as a constituent lipid of a membrane, and further comprising a nucleic acid.

[11]A nucleic acid-introducing agent comprising the cationic lipid having a disulfide bond of any one of [1] to [8], or the lipid membrane structure of [10].

[12]A pharmaceutical composition comprising the cationic lipid having a disulfide bond of any one of [1] to [8], or the lipid membrane structure of [10].

[13]A method for introducing a nucleic acid into a cell in vitro, comprising bringing the nucleic acid-introducing agent of [11] into contact with the cell, wherein the nucleic acid is encapsulated in the nucleic acid-introducing agent.

[14]A method for introducing a nucleic acid into a target cell, comprising administering the nucleic acid-introducing agent of [11] to a living organism to allow for delivery of the nucleic acid to the target cell, wherein the nucleic acid is encapsulated in the nucleic acid-introducing agent.

[15]A method for producing a cell medicine comprising a cell expressing a specific gene, comprising contacting a cell with the nucleic acid-introducing agent of [11] encapsulating a nucleic acid, and introducing the nucleic acid into the cell.

Advantageous Effects of Invention

The cationic lipid of the present invention has a disulfide bond showing biodegradability. Therefore, the disulfide bond is cleaved in the intracellular reductive environment, thus promoting release of materials (nucleic acid) enclosed therein. Hence, the cationic lipid of the present invention or a lipid membrane structure containing same can achieve high efficiency of nucleic acid delivery into the cytoplasm. Therefore, it is advantageous for gene transfer in cells or living organisms, and is particularly useful as a pharmaceutical composition. In addition, since the aforementioned nucleic acid-introducing agent is superior in efficiency of gene transfer into cells, cells expressing a specific gene can be produced with high efficiency, and the agent is useful in the production of cell medicine containing cells expressing a specific gene.

DESCRIPTION OF EMBODIMENTS

While the embodiments of the present invention are described in the following, the present invention is not limited thereto.

The present invention provides a cationic lipid represented by the formula (1):

$$X-(R^1-L^1)_k-R^x-S-S-R^y-L^2-R^2-Y. \quad (1)$$

Only one kind of the above-mentioned cationic lipid may be used, or two or more kinds thereof may be used in combination. In the following, the "cationic lipid represented by the formula (1) having a disulfide bond" is sometimes to be abbreviated as "cationic lipid (1)". The compounds and the like represented by other formulas may also be sometimes abbreviated in the same manner.

X is a nitrogen-containing aliphatic group containing one or more tertiary nitrogens, $R^1$ is an aliphatic hydrocarbon group having not more than 8 carbon atoms, $L^1$ is an ester bond, an amide bond, a carbamate bond, an N-alkylcarbamate bond, a carbonate bond or a urea bond, k is 0 or 1, $R^x$ and $R^y$ are each independently an alkylene group having 2-4 carbon atoms, $L^2$ is an ester bond, an amide bond, a carbamate bond, a carbonate bond, an ether bond or a urea bond, $R^2$ is an alkylene group having not more than 8 carbon atoms, or absent, and Y is a group which (i) contains one or more divalent groups derived from an aromatic compound optionally having a hetero atom, (ii) contains a group containing at least one selected from the group consisting of an ester bond and a carbonate bond on the aromatic ring of the aforementioned divalent group, and (iii) contains at least one selected from the group consisting of an aliphatic hydrocarbon group having 10-37 carbon atoms, a liposoluble vitamin residue, and a residue of a sterol derivative.

One embodiment of preferred X can be represented by the following formula (2).

$$R^{\alpha}-N(R^{\beta})- \quad (2)$$

wherein $R^{\alpha}$ is an aliphatic hydrocarbon group, $R^{\beta}$ is an aliphatic hydrocarbon group, an aliphatic group containing one or more hetero atoms other than nitrogen, or an aliphatic group containing one or more tertiary amines, or $R^\alpha$ and $R^\beta$ may be bonded to form a 3- to 8-membered nitrogen-containing alicyclic ring.

More preferred example of X is a dialkylamino group (wherein the two alkyl groups of the dialkylamino group each independently have 1 to 8 carbon atoms), a 3- to 6-membered cyclic amino group optionally having a hetero atom, or —N($R^a$)—$R^b$, $R^a$ is an alkyl group having 1-8 carbon atoms, $R^b$ is —($CH_2$)q-O—$R^c$, $R^c$ is a hydrogen or an alkyl group having 1-8 carbon atoms, and q is an integer of 2 to 4.

The number of carbon atoms in the two alkyl groups in the dialkylamino group is preferably each independently 1 to 5, more preferably each independently 1 to 4. The alkyl group may be linear, branched, or cyclic.

Specifically, methyl group, ethyl group, propyl group, isopropyl group, cyclopropyl group, n-butyl group, sec-butyl group, isobutyl group, tert-butyl group, cyclobutyl group, pentyl group, isopentyl group, neopentyl group, tert-pentyl group, 1,2-dimethylpropyl group, 2-methylbutyl group, cyclopentyl group and the like can be mentioned. It is preferably each independently methyl group, ethyl group, propyl group or isopropyl group, more preferably each independently methyl group or ethyl group.

The 3- to 6-membered cyclic amino group optionally having a hetero atom means a group in which the substituents of the amino group are bonded to form a ring, the number of atoms forming the ring is 3 to 6, and which may have a hetero atom such as oxygen. The 3- to 6-membered cyclic amino group optionally having a hetero atom is preferably a 5- or 6-membered cyclic amino group optionally having a hetero atom, more preferably a 6-membered cyclic amino group optionally having a hetero atom. As the cyclic amino group, an amino group in which the ring is formed only of a nitrogen atom and a methylene group (—$CH_2$—) is preferred, and may contain an oxygen atom therein. It is specifically a 1-pyrrolidinyl group, a 1-piperidyl group, or a morpholino group (4-morpholinyl group), preferably a 1-piperidyl group or a morpholino group.

The aliphatic hydrocarbon group having not more than 8 carbon atoms for $R^1$ is preferably an alkylene group, an alkenylene group, or an alkynylene group, and more preferably an alkylene group or an alkenylene group.

The alkylene group having not more than 8 carbon atoms may be linear or branched chain. The carbon number of the above-mentioned alkylene group is preferably not more than 6, more preferably not more than 4. The alkylene group having not more than 8 carbon atoms is preferably methylene group, ethylene group, trimethylene group, tetramethylene group, isopropylene group (—$CH(CH_3)CH_2$—, —$CH_2CH(CH_3)$—), isobutylene group (—$C(CH_3)_2CH_2$—, —$CH_2C(CH_3)_2$—), pentamethylene group, or hexamethylene group, more preferably methylene group, ethylene group, trimethylene group, isopropylene group (—$CH(CH_3)CH_2$—, —$CH_2CH(CH_3)$—), tetramethylene group, or isobutylene group (—$C(CH_3)_2CH_2$—, —$CH_2C(CH_3)_2$—).

The alkenylene group having not more than 8 carbon atoms may be linear or branched chain. The carbon number of the above-mentioned alkenylene group is preferably not more than 6, more preferably not more than 4. The alkenylene group having not more than 8 carbon atoms is preferably propenylene group (—$CH_2CH{=}CH$—, —$CH{=}CHCH_2$—), butenylene group, isopropenylene group, isobutenylene group, pentenylene group, hexaylene group, more preferably propenylene group (—$CH_2CH{=}CH$—, —$CH{=}CHCH_2$—), butenylene group, isopropenylene group, or isobutenylene group.

$L^1$ is an ester bond, an amide bond, a carbamate bond, an N-alkylcarbamate bond, a carbonate bond or a urea bond, preferably an ester bond, an amide bond, a carbamate bond, an N-methylcarbamate bond or a carbonate bond.

In the present specification, N-alkylcarbamate bond is —$NR^9$—CO—O— or —O—CO—$NR^9$—, and $R^9$ is an alkyl group having 1-8 carbon atoms. The alkyl group having 1-8 carbon atoms may be linear, branched chain or cyclic. The carbon number of the above-mentioned alkyl group is preferably 1 to 6, more preferably 1 to 4. Specifically, methyl group, ethyl group, propyl group, isopropyl group, cyclopropyl group, n-butyl group, sec-butyl group, isobutyl group, tert-butyl group, cyclobutyl group, pentyl group, isopentyl group, neopentyl group, tert-pentyl group, 1,2-dimethylpropyl group, 2-methylbutyl group, cyclopentyl group and the like can be mentioned. It is preferably a methyl group, an ethyl group, a propyl group or an isopropyl group, more preferably a methyl group.

k is 0 or 1. Here, when k is 0, it means that $R^1$-$L^1$ does not exist, that is, X and $R^x$ are directly bonded. The same applies when l, m, n, and the like are 0.

The alkylene group having 2-5 carbon atoms for $R^x$ or $R^y$ may be linear or branched chain, preferably linear. The carbon number of the above-mentioned alkylene group is preferably 2 to 4, more preferably 2.

It is specifically an ethylene group, a trimethylene group, a tetramethylene group, an isopropylene group (—$CH(CH_3)CH_2$—, —$CH_2CH(CH_3)$—), or an isobutylene group (—$C(CH_3)_2CH_2$—, —$CH_2C(CH_3)_2$—), preferably an ethylene group or a trimethylene group, more preferably an ethylene group.

$L^2$ is an ester bond, an amide bond, a carbamate bond, a carbonate bond, an ether bond or a urea bond, preferably an ester bond or an amide bond, more preferably an ester bond.

$R^2$ is an alkylene group having not more than 8 carbon atoms, or absent. That $R^2$ is absent means that $L^2$ and Y are directly bonded.

The alkylene group having not more than 8 carbon atoms for $R^2$ may be linear or branched chain, preferably linear. The carbon number of the above-mentioned alkylene group is preferably not more than 6, more preferably not more than 4. The alkylene group having not more than 8 carbon atoms is preferably methylene group, ethylene group, trimethylene group, tetramethylene group, isopropylene group (—$CH(CH_3)CH_2$—, —$CH_2CH(CH_3)$—), isobutylene group (—$C(CH_3)_2CH_2$—, —$CH_2C(CH_3)_2$—), pentamethylene group, hexamethylene group, more preferably methylene group, ethylene group, trimethylene group, isopropylene group (—$CH(CH_3)CH_2$—, —$CH_2CH(CH_3)$—), tetramethylene group, or isobutylene group (—$C(CH_3)_2CH_2$—, —$CH_2C(CH_3)_2$—).

The alkyl group having 1-8 carbon atoms for $R^a$ or $R^c$ may be linear or branched chain, preferably linear. The carbon number of the above-mentioned alkyl group is preferably 1 to 6, more preferably 1 to 4. Specific examples of the alkyl group having 1-8 carbon atoms include methyl group, ethyl group, propyl group, isopropyl group, n-butyl group, sec-butyl group, isobutyl group, tert-butyl group, pentyl group, isopentyl group, neopentyl group, tert-pentyl group, 1,2-dimethylpropyl group, 2-methylbutyl group and the like. It is preferably methyl group, ethyl group, propyl group or isopropyl group, more preferably methyl group.

One embodiment of preferred Y can be represented by the following formula (3).

(3)

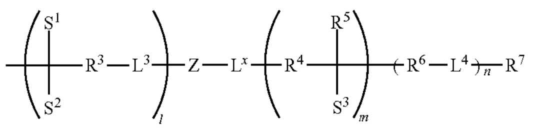

wherein $R^3$ is an alkylene group having not more than 8 carbon atoms, $L^3$ is an ester bond or a carbonate bond, $S^1$ is a hydrogen, an alkyl group having 1-8 carbon atoms, $—R^e-L^a-R^{7'}$, or $—R^e-L^a-Z'-L^b-R^{7'}$, $S^2$ is $—R^{e'}-L^a-R^{7''}$ or $—R^{e'}-L^a-Z'-L^b-R^{7''}$, $R^e$ and $R^{e'}$ are each independently an alkylene group having not more than 8 carbon atoms, $L^a$ is an ester bond or a carbonate bond, $L^b$ is an ester bond or a carbonate bond, 1 is 0 or 1, Z, Z' and Z" are each independently a divalent group derived from an aromatic compound having 3-16 carbon atoms and at least one aromatic ring, and optionally having a hetero atom, $L^x$ is an ester bond or a carbonate bond, $R^4$ is an alkylene group having not more than 8 carbon atoms, or absent, $R^5$ is a hydrogen or an alkyl group having 1-8 carbon atoms, $S^3$ is $—R^{6'}-L^{4'}-R^{7'''}$, m is 0 or 1, $R^6$ and $R^{6'}$ are each independently an alkylene group having not more than 8 carbon atoms, or absent, $L^4$ and $L^{4'}$ are each independently an ester bond or a carbonate bond, $R^7$, $R^{7'}$, $R^{7''}$ and $R^{7'''}$ are each independently an aliphatic hydrocarbon group having 10-37 carbon atoms, or $—(CH_2)p-C(═O)—R^f$, $R^f$ is a residue of a liposoluble vitamin having a hydroxyl group or a residue of a sterol derivative having a hydroxyl group, and p is 2 or 3, and n is 0 or 1.

$R^4$ is an alkylene group having not more than 8 carbon atoms, or absent. That $R^4$ is absent means that the carbon atom to which $R^5$ and $S^3$ are bonded and $L^x$ are directly bonded.

$R^6$ and $R^{6'}$ are each independently an alkylene group having not more than 8 carbon atoms, or absent. That $R^6$ is absent means that when m=0, $L^x$ and $L^4$ are directly bonded and when m=1, the carbon atom to which $R^5$ and $S^3$ are bonded and $L^4$ are directly bonded. That $R^{6'}$ is absent means that the carbon atom to which $R^4$ and $R^5$ are bonded and $L^{4'}$ are directly bonded.

The alkylene group having not more than 8 carbon atoms for $R^3$, $R^4$, $R^6$, $R^{6'}$, $R^e$ or $R^{e'}$ may be linear or branched chain, preferably linear. The carbon number of the above-mentioned alkylene group is preferably not more than 6, more preferably not more than 4. The alkylene group having not more than 8 carbon atoms is preferably methylene group, ethylene group, trimethylene group, tetramethylene group, isopropylene group ($—CH(CH_3)CH_2—$, $—CH_2CH(CH_3)—$), isobutylene group ($—C(CH_3)_2CH_2—$, $—CH_2C(CH_3)_2—$), pentamethylene group, or hexamethylene group, more preferably methylene group, ethylene group, trimethylene group, isopropylene group ($—CH(CH_3)CH_2—$, $—CH_2CH(CH_3)—$), tetramethylene group, or isobutylene group ($—C(CH_3)_2CH_2—$, $—CH_2C(CH_3)_2—$).

The alkyl group having 1-8 carbon atoms for $R^5$ or $S^1$ may be linear or branched, preferably linear. The carbon number of the above-mentioned alkyl group is preferably 1-6, more preferably 1-4. Specific examples of the alkyl group having 1-8 carbon atoms include methyl group, ethyl group, propyl group, isopropyl group, n-butyl group, sec-butyl group, isobutyl group, tert-butyl group, pentyl group, isopentyl group, neopentyl group, tert-pentyl group, 1,2-dimethylpropyl group, 2-methylbutyl group, and the like. Preferably, it is a methyl group, an ethyl group, a propyl group or an isopropyl group, more preferably a methyl group.

$L^x$, $L^3$, $L^4$, $L^{4'}$, $L^a$ and $L^b$ are each an ester bond or a carbonate bond, preferably an ester bond.

Z, Z' and Z" are each independently a divalent group derived from an aromatic compound having 3-16 carbon atoms and at least one aromatic ring, and optionally having a hetero atom. Here, the divalent group means a divalent group having a structure obtained by removing two hydrogen atoms from the above-mentioned aromatic compound. The number of carbon atoms of the above-mentioned aromatic compound is preferably 6 to 12, more preferably 6 or 7. The number of aromatic rings of the above-mentioned aromatic compound is preferably 1. Z, Z' and Z" may be the same or different, and Z, Z' and Z" are preferably the same.

The aromatic ring of the above-mentioned aromatic compound may be either an aromatic hydrocarbon ring or an aromatic hetero ring. Examples of the aromatic hydrocarbon ring include a benzene ring, a naphthalene ring, and an anthracene ring. Examples of the aromatic hetero ring include an imidazole ring, a pyrazole ring, an oxazole ring, an isoxazole ring, a thiazole ring, an isothiazole ring, a triazine ring, a pyrrole ring, a furanthiophene ring, a pyrimidine ring, a pyridazine ring, a pyrazine ring, a pyridine ring, a purine ring, a pteridine ring, a benzimidazole ring, an indole ring, a benzofuran ring, a quinazoline ring, a phthalazine ring, a quinoline ring, an isoquinoline ring, a coumarin ring, a chromone ring, a benzodiazepine ring, a phenoxazine ring, a phenothiazine ring, and an acridine ring. The aromatic ring of the aromatic compound is preferably a benzene ring, a naphthalene ring, or an anthracene ring, more preferably a benzene ring.

The aromatic ring of the above-mentioned aromatic compound may have a substituent. Examples of the substituent include an acyl group having 2-4 carbon atoms, an alkoxycarbonyl group having 2-4 carbon atoms, a carbamoyl group having 2-4 carbon atoms, an acyloxy group having 2-18 carbon atoms, an acylamino group having 2-4 carbon atoms, an alkoxycarbonylamino group having 2-4 carbon atoms, a fluorine atom, a chlorine atom, a bromine atom, an iodine atom, an alkylsulfanyl group having 1-4 carbon atoms, an alkylsulfonyl group having 1-4 carbon atoms, an arylsulfonyl group having 6-10 carbon atoms, a nitro group, a trifluoromethyl group, a cyano group, an alkyl group having 1-4 carbon atoms, a ureido group having 1-4 carbon atoms, an alkoxy group having 1-4 carbon atoms, an aryl group having 6-10 carbon atoms, and an aryloxy group having 6-10 carbon atoms. Preferred examples of the above-mentioned substituent include an acetyl group, a methoxycarbonyl group, a methylcarbamoyl group, an acetoxy group, an acetamido group, a methoxycarbonylamino group, a fluorine atom, a chlorine atom, a bromine atom, an iodine atom, a methylsulfanyl group, a phenylsulfonyl group, a nitro group, a trifluoromethyl group, a cyano group, a methyl group, an ethyl group, a propyl group, an isopropyl group, a tert-butyl group, a ureido group, a methoxy group, an ethoxy group, a propoxy group, an isopropoxy group, a tert-butoxy group, a phenyl group, a phenoxy group, and the like.

Z, Z' and Z" are preferably each independently the formula (4):

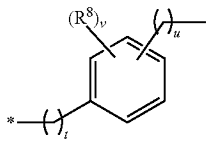

(4)

wherein t is an integer of 0 to 3, u is an integer of 0 to 3, v is an integer of 0 to 4, and $R^8$ in the number of v are each independently a substituent, is the bonding position with $L^3$ or $L^a$, t is preferably 0 or 1, more preferably 1.

u is preferably an integer of 0 to 2, more preferably 0.

v is preferably an integer of 0 to 2, more preferably 0 or 1, further preferably 0.

Examples of $R^8$ include acyl group having 2-4 carbon atoms, alkoxycarbonyl group having 2-4 carbon atoms, carbamoyl group having 2-4 carbon atoms, acyloxy group having 2-18 carbon atoms, acylamino group having 2-4 carbon atoms, alkoxycarbonylamino group having 2-4 carbon atoms, fluorine atom, chlorine atom, bromine atom, iodine atom, alkylsulfanyl group having 1-4 carbon atoms, alkylsulfonyl group having 1-4 carbon atoms, arylsulfonyl group having 6-10 carbon atoms, nitro group, trifluoromethyl group, cyano group, alkyl group having 1-4 carbon atoms, ureido group having 1-4 carbon atoms, alkoxy group having 1-4 carbon atoms, aryl group having 6-10 carbon atoms, aryloxy group having 6-10 carbon atoms, and the like. Preferred examples of $R^e$ include acetyl group, methoxycarbonyl group, methylcarbamoyl group, acetoxy group, propanoyloxy group, butanoyloxy group, pentanoyloxy group, hexanoyloxy group, heptanoyloxy group, octanoyloxy group, nonanoyloxy group, decanoyloxy group, undecanoyloxy group, dodecanoyloxy group, tridecanoyloxy group, tetradecanoyloxy group, pentadecanoyloxy group, hexadecanoyloxy group, heptadecanoyloxy group, octadecanoyloxy group, yloxy group, octadecenoyloxy group, octadecadienoyloxy group, acetamido group, methoxycarbonylamino group, fluorine atom, chlorine atom, bromine atom, iodine atom, methylsulfanyl group, phenylsulfonyl group, nitro group, trifluoromethyl group, cyano group, methyl group, ethyl group, propyl group, isopropyl group, tert-butyl group, ureido group, methoxy group, ethoxy group, propoxy group, isopropoxy group, tert-butoxy group, phenyl group, phenoxy group, and the like. When $R^8$ is present in plurality, each $R^8$ may be the same or different.

$R^7$, $R^{7'}$, $R^{7''}$ and $R^{7'''}$ are each independently an aliphatic hydrocarbon group having 10-37 carbon atoms or $-(CH_2)p-C(=O)-R^f$, $R^f$ is a residue of a liposoluble vitamin having a hydroxyl group or a residue of a sterol derivative having a hydroxyl group, and p is 2 or 3. $R^7$, $R^{7'}$, $R^{7''}$ and $R^{7'''}$ each may be the same or different.

In the present specification, the residue of a liposoluble vitamin having a hydroxyl group is a monovalent group having a structure obtained by removing a hydrogen atom from the hydroxyl group of liposoluble vitamin. In addition, the residue of a sterol derivative having a hydroxyl group is a monovalent group having a structure obtained by removing a hydrogen atom from the hydroxyl group of a sterol derivative.

The aliphatic hydrocarbon group having 10-37 carbon atoms may be linear or branched chain. The carbon number of the above-mentioned aliphatic hydrocarbon group is preferably 12 to 37, more preferably 13 to 37, further preferably 15 to 37.

The above-mentioned aliphatic hydrocarbon group may be saturated or unsaturated. When the above-mentioned aliphatic hydrocarbon group is an unsaturated aliphatic hydrocarbon group, the number of the unsaturated bond is preferably 1 to 6, more preferably 1 to 3, further preferably 1 or 2. While the unsaturated bond may be a carbon-carbon double bond or a carbon-carbon triple bond, it is preferably a carbon-carbon double bond. The above-mentioned aliphatic hydrocarbon group is preferably an alkyl group or an alkenyl group.

Examples of the aliphatic hydrocarbon group having 10-37 carbon atoms include decyl group, undecyl group, dodecyl group, tridecyl group, tetradecyl group, pentadecyl group, hexadecyl group, heptadecyl group, octadecyl group, nonadecyl group, icosyl group, henicosyl group, docosyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group, henicosenyl group, heneicosenyl group, docosenyl group, dodecadienyl group, tridecadienyl group, tetradecadienyl group, pentadecadienyl group, hexadecadienyl group heptadecadienyl group, octadecadienyl group, nonadecadienyl group, icosadienyl group, henicosadienyl group, heneicosadienyl group, docosadienyl group, octadecatrienyl group, icosatrienyl group, icosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group, 1-dodecyltridecyl group, 1-tetradecylpentadecyl group, 1-hexadecylheptadecyl group, 1-octadecylnonadecyl group and the like.

The aliphatic hydrocarbon group having 10-37 carbon atoms is preferably undecyl group, dodecyl group, tridecyl group, tetradecyl group, pentadecyl group, hexadecyl group, heptadecyl group, octadecyl group, nonadecyl group, icosyl group, henicosyl group, docosyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group, henicosenyl group, heneicosenyl group, docosenyl group, dodecadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, heneicosadienyl group, docosadienyl group, octadecatrienyl group, icosatrienyl group, icosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group, 1-dodecyltridecyl group, 1-tetradecylpentadecyl group, 1-hexadecylheptadecyl group, or 1-octadecylnonadecyl group, particularly preferably pentadecyl group, hexadecyl group, heptadecyl group, octadecyl group, nonadecyl group, icosyl group, henicosyl group, docosyl group, heptadecenyl group, dodecadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, heneicosadienyl group, docosadienyl group, octadecatrienyl group, icosatrienyl group, icosatetraenyl group, icosapentaenyl group, docosahexaenyl group, isostearyl group, 1-hexylheptyl group, 1-hexylnonyl group, 1-octylnonyl group, 1-octylundecyl group, 1-decylundecyl group, 1-dodecyltridecyl group, 1-tetradecylpentadecyl group, 1-hexadecylheptadecyl group, or 1-octadecylnonadecyl group.

The liposoluble vitamin having a hydroxyl group is, for example, retinol, ergosterol, 7-dehydrocholesterol, calciferol, cholecalciferol, dihydroergocalciferol, dihydrotachysterol, tocopherol, tocotrienol and the like. Preferred example of the liposoluble vitamin having a hydroxyl group is tocopherol.

Examples of the sterol derivative having a hydroxyl group include cholesterol, cholestanol, stigmasterol, β-sitosterol, lanosterol, and ergosterol and the like. The sterol derivative having a hydroxyl group is preferably cholesterol or cholestanol.

$R^f$ is preferably a residue of a liposoluble vitamin having a hydroxyl group. p is preferably 2.

l, m, n are each 0 or 1. Preferred combinations of l, m, n include l=0, m=0, n=0
l=0, m=0, n=1
l=0, m=1, n=1
l=1, m=0, n=0,
particularly preferably
l=0, m=0, n=0
l=0, m=1, n=1
l=1, m=0, n=0.

Preferred examples of the cationic lipid (1) of the present invention include the following cationic lipid.

Cationic lipid (1) wherein

X is a dialkylamino group (carbon numbers of two alkyl groups of the aforementioned dialkylamino group are each independently 1 to 8), a 3- to 6-membered cyclic amino group optionally having a hetero atom, or —N($R^a$)—$R^b$, $R^a$ is alkyl group having 1-8 carbon atoms, $R^b$ is —($CH_2$)q-O—$R^c$, $R^c$ is a hydrogen or an alkyl group having 1-8 carbon atoms, q is an integer of 2 to 4;

$R^1$ is an alkylene group having not more than 6 carbon atoms, or an alkenylene group having not more than 6 carbon atoms;

$L^1$ is an ester bond, an amide bond, a carbamate bond or a carbonate bond k is 0 or 1;

$R^x$ and $R^y$ are each independently an alkylene group having 2-4 carbon atoms group;

$L^2$ is an ester bond or an amide bond;

$R^2$ is an alkylene group having not more than 6 carbon atoms, or absent;

Y is a group represented by the formula (Y):

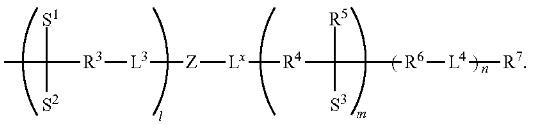

wherein $R^3$ is an alkylene group having not more than 6 carbon atoms, $L^3$ is an ester bond, $S^1$ is a hydrogen, an alkyl group having 1-8 carbon atoms, —$R^e$-$L^a$-$R^{7'}$, or —$R^e$-$L^a$-Z'-$L^b$-$R^{7'}$, $S^2$ is —$R^{e'}$-$L^a$-$R^{7''}$ or —$R^{e'}$-$L^a$-Z'-$L^b$-$R^{7''}$, $R^e$ and $R^{e'}$ are each independently an alkylene group having not more than 6 carbon atoms, $L^a$ is an ester bond, $L^b$ is an ester bond, l is 0 or 1, $L^x$ is an ester bond or a carbonate bond, $R^4$ is an alkylene group having not more than 6 carbon atoms, or absent, $R^5$ is a hydrogen or an alkyl group having 1-8 carbon atoms, $S^3$ is —$R^{6'}$-$L^{4'}$-$R^{7'''}$, m is 0 or 1, $R^6$ and $R^{6'}$ are each independently an alkylene group having not more than 6 carbon atoms, or absent, $L^4$ and $L^{4'}$ are each an ester bond, $R^7$, $R^{7'}$, $R^{7''}$ and $R^{7'''}$ are each independently an aliphatic hydrocarbon group having 10-37 carbon atoms, or —($CH_2$)p-C(=O)—$R^f$, $R^f$ is a residue of a liposoluble vitamin having a hydroxyl group or a residue of a sterol derivative having a hydroxyl group, and p is 2 or 3, and n is 0 or 1;

Z, Z' and Z'' are each independently a group represented by the formula (Z):

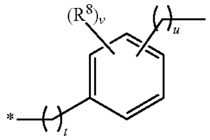

wherein t is an integer of 0 or 1, u is an integer of 0 to 2, v is an integer of 0 to 2, and $R^8$ in the number of v are each independently an acyl group having 2-4 carbon atoms, an alkoxycarbonyl group having 2-4 carbon atoms, a carbamoyl group having 2-4 carbon atoms, an acyloxy group having 2-18 carbon atoms, an acylamino group having 2-4 carbon atoms, an alkoxycarbonylamino group having 2-4 carbon atoms, a fluorine atom, a chlorine atom, a bromine atom, an iodine atom, an alkylsulfanyl group having 1-4 carbon atoms, an alkylsulfonyl group having 1-4 carbon atoms, an arylsulfonyl group having 6-10 carbon atoms, a nitro group, a trifluoromethyl group, a cyano group, an alkyl group having 1-4 carbon atoms, a ureido group having 1-4 carbon atoms, an alkoxy group having 1-4 carbon atoms, an aryl group having 6-10 carbon atoms, or an aryloxy group having 6-10 carbon atoms.

The cationic lipid (1) of the present invention may exist as geometric isomer, stereoisomers such as optical isomer, tautomer, or the like, and the cationic lipid (1) of the present invention includes all possible isomers and mixtures thereof, including these. In a mixture of plural isomers, the ratio of each isomer is not particularly limited.

The cationic lipid (1) of the present invention may form a salt. The salt is not particularly limited as long as it is a pharmacologically acceptable salt. Examples thereof include salts with inorganic acids such as hydrochloric acid, hydrobromic acid, nitric acid, sulfuric acid, phosphoric acid, and the like and salts with organic acids such as acetic acid, oxalic acid, maleic acid, fumaric acid, benzoic acid, methanesulfonic acid and the like.

Preferred specific examples of the compound of the present invention include the compounds described in Example 1 to Example 46 below, but the present invention is not limited thereto. The compounds described in Example 1 to Example 46 are referred to as compound 1 to compound 46, respectively.

The cationic lipid (1) of the present invention is preferably at least one selected from the group consisting of these, more preferably at least one selected from the group consisting of compounds 5, 7, 8, 9, 10, 11, 15, 19, 21, 22, 23, 24, 25, 28, 29, 30, 31, 32, 34, 35, 36, and 42, even more preferably at least one selected from the group consisting of compounds 5, 7, 8, 9, 10, 11, 15, 21, 22, 24, 31, 32, 34, 35, and 36, most preferably compound 31 or compound 34.

TABLE 1

| name | structure |
|---|---|
| compound 1 | 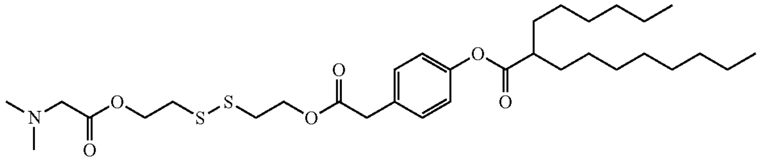 [SMILES: CCCCCCCCC(CCCCCC)C(=O)Oc1ccc(CC(=O)OCCSSCCOC(=O)CN(C)C)cc1] |
| compound 2 | 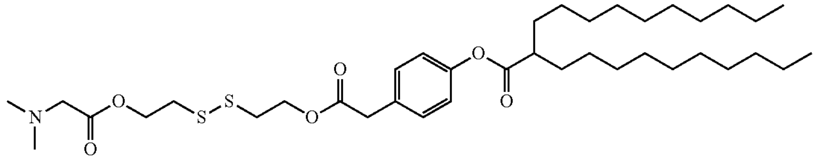 [SMILES: CCCCCCCCCCC(CCCCCCCCCC)C(=O)Oc1ccc(CC(=O)OCCSSCCOC(=O)CN(C)C)cc1] |
| compound 3 | 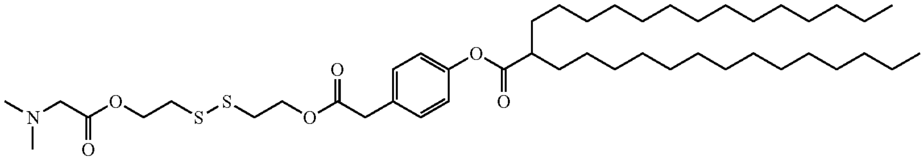 [SMILES: CCCCCCCCCCCCCCC(CCCCCCCCCCCCCC)C(=O)Oc1ccc(CC(=O)OCCSSCCOC(=O)CN(C)C)cc1] |
| compound 4 | 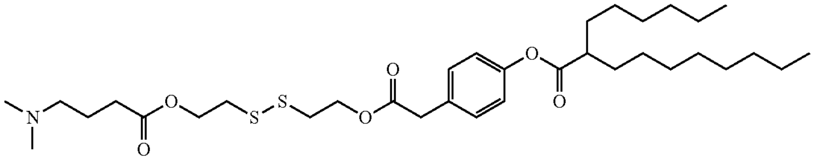 [SMILES: CCCCCCCCC(CCCCCC)C(=O)Oc1ccc(CC(=O)OCCSSCCOC(=O)CCCN(C)C)cc1] |
| compound 5 | 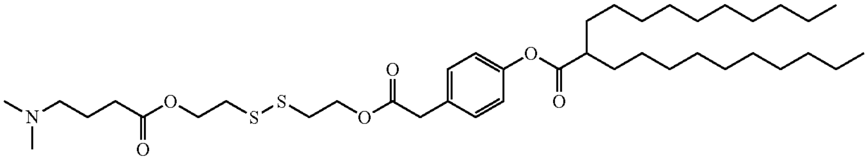 [SMILES: CCCCCCCCCCC(CCCCCCCCCC)C(=O)Oc1ccc(CC(=O)OCCSSCCOC(=O)CCCN(C)C)cc1] |
| compound 6 | 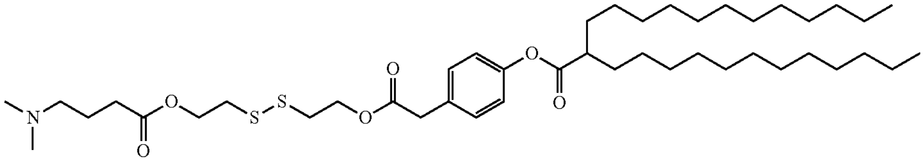 [SMILES: CCCCCCCCCCCCC(CCCCCCCCCCCC)C(=O)Oc1ccc(CC(=O)OCCSSCCOC(=O)CCCN(C)C)cc1] |
| compound 7 | 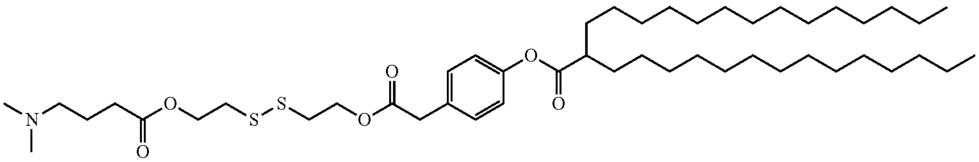 [SMILES: CCCCCCCCCCCCCCC(CCCCCCCCCCCCCC)C(=O)Oc1ccc(CC(=O)OCCSSCCOC(=O)CCCN(C)C)cc1] |
| compound 8 | 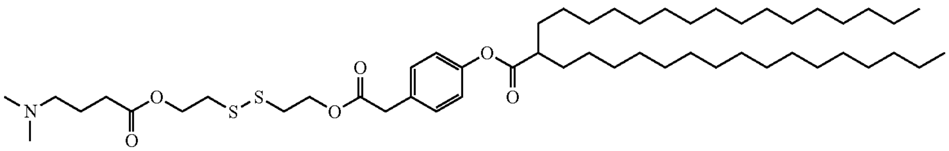 [SMILES: CCCCCCCCCCCCCCCCC(CCCCCCCCCCCCCCCC)C(=O)Oc1ccc(CC(=O)OCCSSCCOC(=O)CCCN(C)C)cc1] |

TABLE 1-continued
| name | structure |
| --- | --- |
| compound 9 | 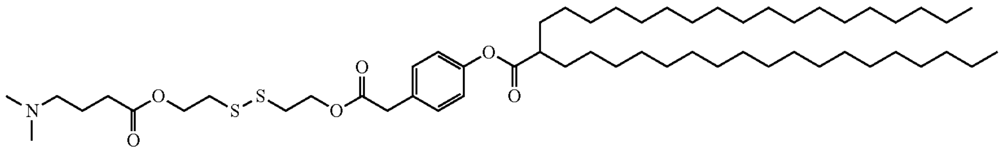 [SMILES: CCCCCCCCCCCCCCCCCCC(CCCCCCCCCCCCCCCCCC)C(=O)Oc1ccc(CC(=O)OCCSSCCOC(=O)CCCN(C)C)cc1] |
| compound 10 | 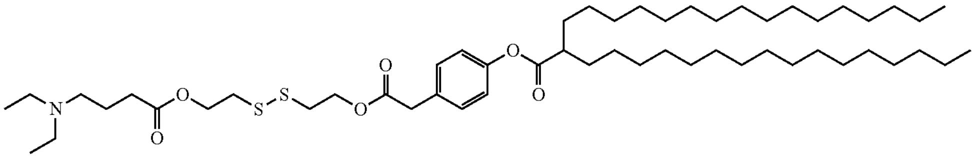 [SMILES: CCCCCCCCCCCCCCCCC(CCCCCCCCCCCCCCCC)C(=O)Oc1ccc(CC(=O)OCCSSCCOC(=O)CCCN(CC)CC)cc1] |
| compound 11 | 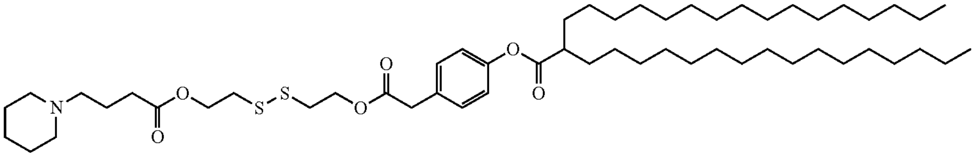 [SMILES: CCCCCCCCCCCCCCCCC(CCCCCCCCCCCCCCCC)C(=O)Oc1ccc(CC(=O)OCCSSCCOC(=O)CCCN2CCCCC2)cc1] |
| compound 12 | 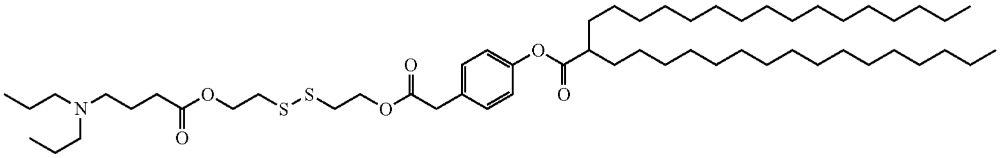 [SMILES: CCCCCCCCCCCCCCCCC(CCCCCCCCCCCCCCCC)C(=O)Oc1ccc(CC(=O)OCCSSCCOC(=O)CCCN(CCC)CCC)cc1] |
| compound 13 | 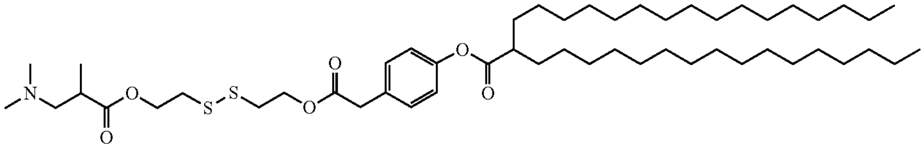 [SMILES: CCCCCCCCCCCCCCCCC(CCCCCCCCCCCCCCCC)C(=O)Oc1ccc(CC(=O)OCCSSCCOC(=O)C(C)CN(C)C)cc1] |
| compound 14 | 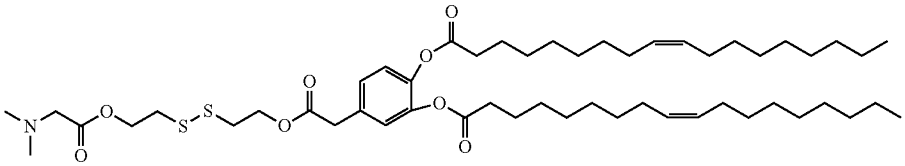 [SMILES: CCCCCCCC/C=C\CCCCCCCC(=O)Oc1ccc(CC(=O)OCCSSCCOC(=O)CN(C)C)cc1OC(=O)CCCCCCC/C=C\CCCCCCCC] |
| compound 15 | 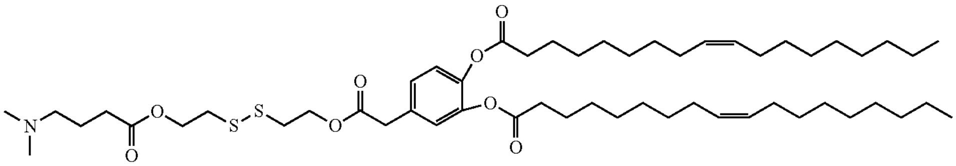 [SMILES: CCCCCCCC/C=C\CCCCCCCC(=O)Oc1ccc(CC(=O)OCCSSCCOC(=O)CCCN(C)C)cc1OC(=O)CCCCCCC/C=C\CCCCCCCC] |
| compound 16 | 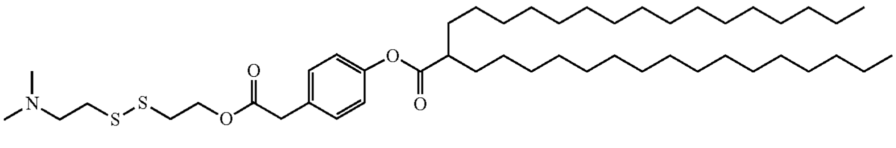 [SMILES: CCCCCCCCCCCCCCCCC(CCCCCCCCCCCCCCCC)C(=O)Oc1ccc(CC(=O)OCCSSCCN(C)C)cc1] |
| compound 17 | 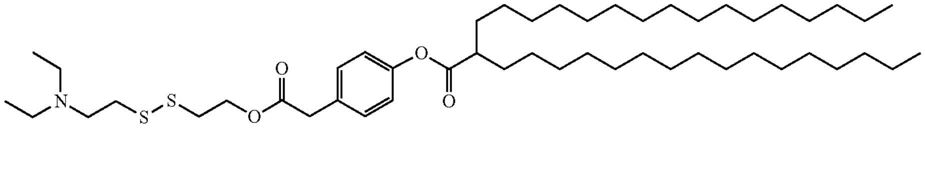 [SMILES: CCCCCCCCCCCCCCCCC(CCCCCCCCCCCCCCCC)C(=O)Oc1ccc(CC(=O)OCCSSCCN(CC)CC)cc1] |

TABLE 1-continued
| name | structure |
| --- | --- |
| compound 18 | 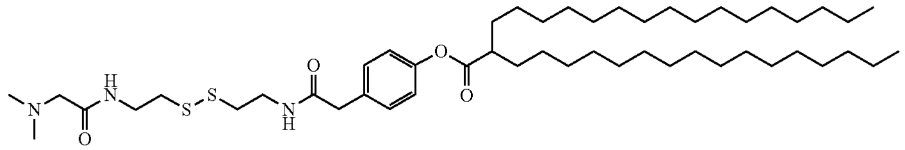 [SMILES: CCCCCCCCCCCCCCCCC(CCCCCCCCCCCCCCCC)C(=O)Oc1ccc(CC(=O)NCCSSCCNC(=O)CN(C)C)cc1] |
| compound 19 | 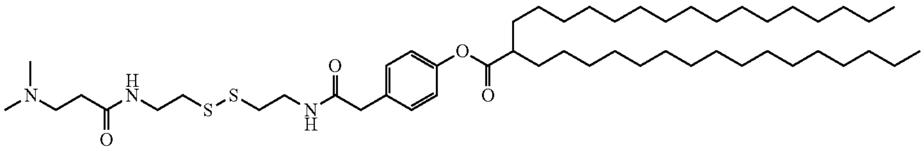 [SMILES: CCCCCCCCCCCCCCCCC(CCCCCCCCCCCCCCCC)C(=O)Oc1ccc(CC(=O)NCCSSCCNC(=O)CCN(C)C)cc1] |
| compound 20 | 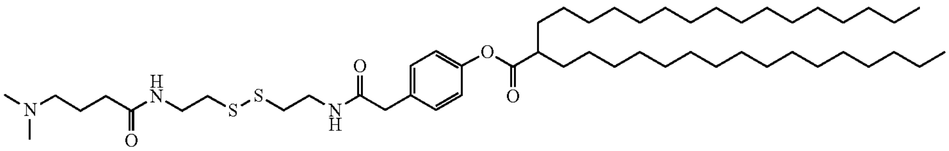 [SMILES: CCCCCCCCCCCCCCCCC(CCCCCCCCCCCCCCCC)C(=O)Oc1ccc(CC(=O)NCCSSCCNC(=O)CCCN(C)C)cc1] |
| compound 21 | 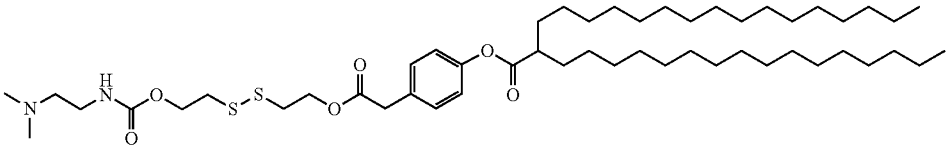 [SMILES: CCCCCCCCCCCCCCCCC(CCCCCCCCCCCCCCCC)C(=O)Oc1ccc(CC(=O)OCCSSCCOC(=O)NCCN(C)C)cc1] |
| compound 22 | 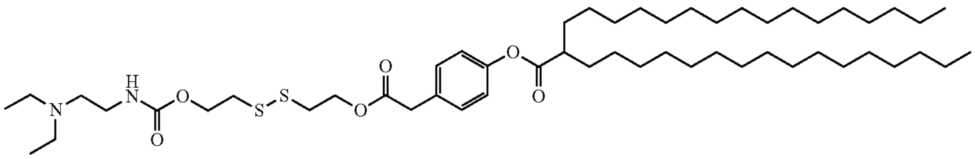 |
| compound 23 | 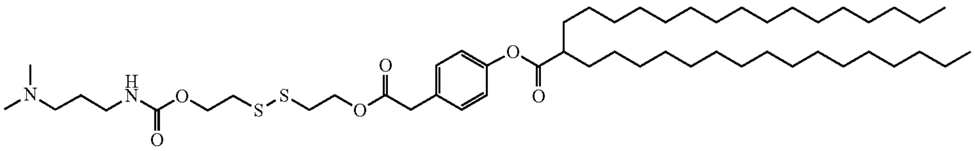 |
| compound 24 | 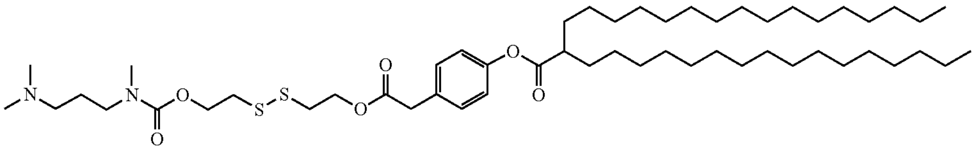 [SMILES: CCCCCCCCCCCCCCCCC(CCCCCCCCCCCCCCCC)C(=O)Oc1ccc(CC(=O)OCCSSCCOC(=O)N(C)CCCN(C)C)cc1] |
| compound 25 | 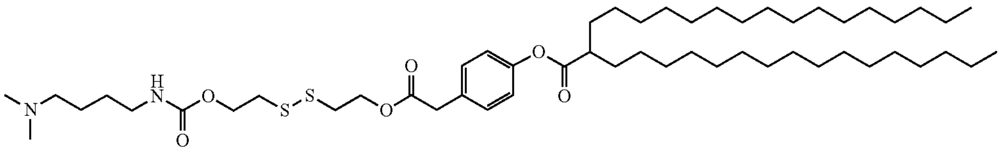 [SMILES: CCCCCCCCCCCCCCCCC(CCCCCCCCCCCCCCCC)C(=O)Oc1ccc(CC(=O)OCCSSCCOC(=O)NCCCCN(C)C)cc1] |
| compound 26 | 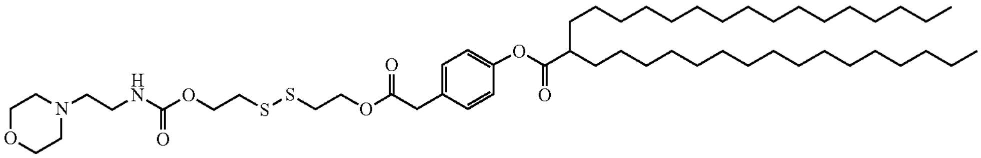 [SMILES: CCCCCCCCCCCCCCCCC(CCCCCCCCCCCCCCCC)C(=O)Oc1ccc(CC(=O)OCCSSCCOC(=O)NCCN2CCOCC2)cc1] |

TABLE 1-continued
| name | structure |
| --- | --- |
| compound 27 | 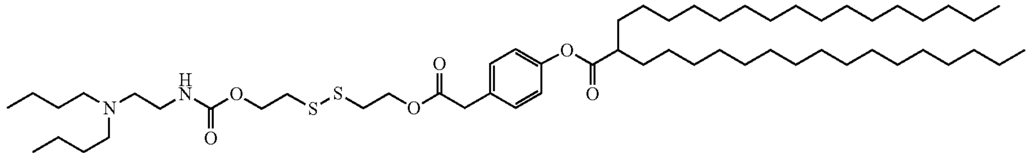 [SMILES: CCCCCCCCCCCCCCCCC(CCCCCCCCCCCCCCCC)C(=O)Oc1ccc(CC(=O)OCCSSCCOC(=O)NCCN(CCCC)CCCC)cc1] |
| compound 28 | 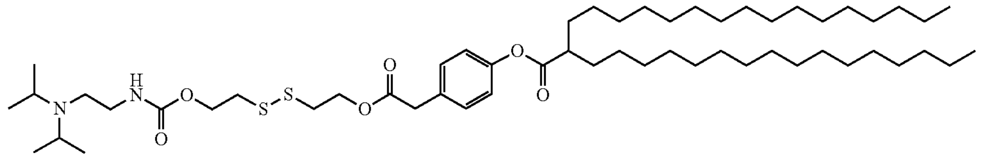 [SMILES: CCCCCCCCCCCCCCCCC(CCCCCCCCCCCCCCCC)C(=O)Oc1ccc(CC(=O)OCCSSCCOC(=O)NCCN(C(C)C)C(C)C)cc1] |
| compound 29 | 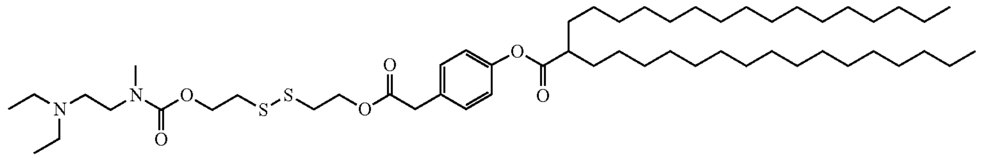 [SMILES: CCCCCCCCCCCCCCCCC(CCCCCCCCCCCCCCCC)C(=O)Oc1ccc(CC(=O)OCCSSCCOC(=O)N(C)CCN(CC)CC)cc1] |
| compound 30 | 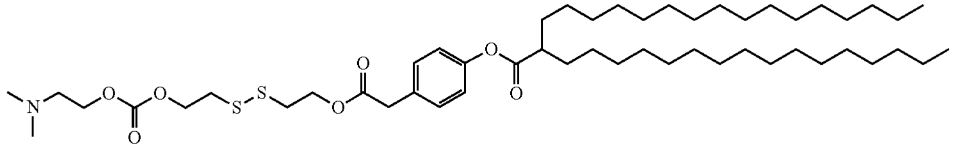 [SMILES: CCCCCCCCCCCCCCCCC(CCCCCCCCCCCCCCCC)C(=O)Oc1ccc(CC(=O)OCCSSCCOC(=O)OCCN(C)C)cc1] |
| compound 31 | 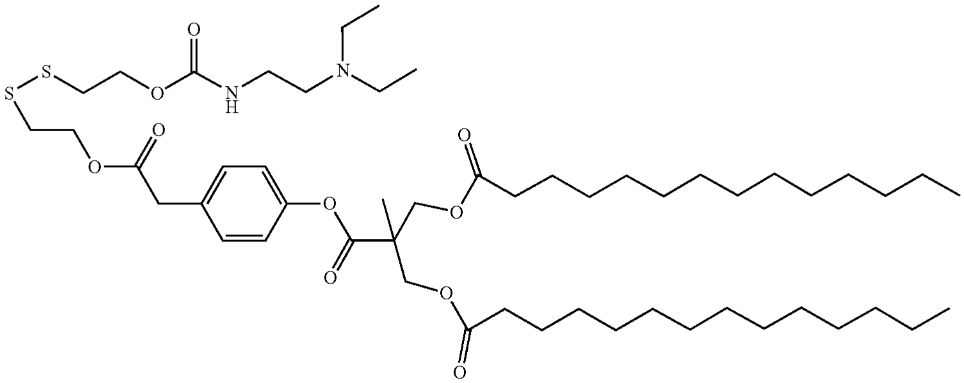 [SMILES: CCCCCCCCCCCCCC(=O)OCC(C)(COC(=O)CCCCCCCCCCCCC)C(=O)Oc1ccc(CC(=O)OCCSSCCOC(=O)NCCN(CC)CC)cc1] |
| compound 32 | 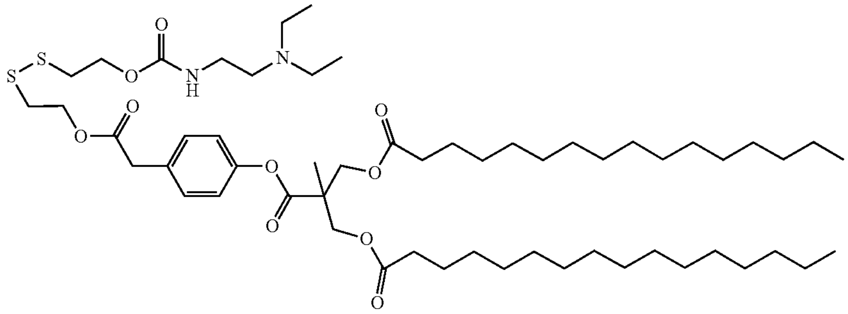 [SMILES: CCCCCCCCCCCCCCCC(=O)OCC(C)(COC(=O)CCCCCCCCCCCCCCC)C(=O)Oc1ccc(CC(=O)OCCSSCCOC(=O)NCCN(CC)CC)cc1] |

TABLE 1-continued
| name | structure |
| --- | --- |
| compound 33 | 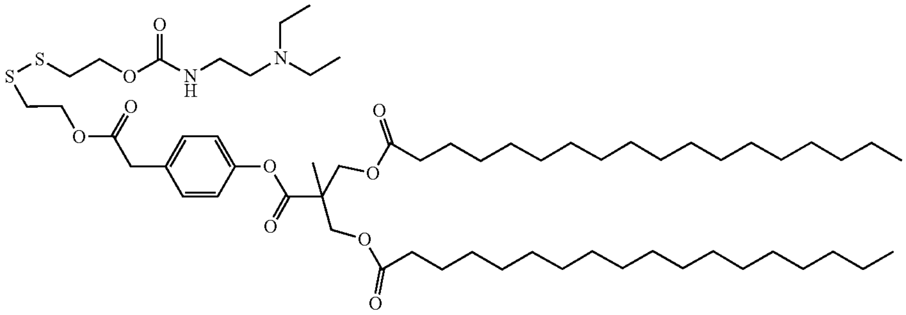 [SMILES: CCCCCCCCCCCCCCCCCC(=O)OCC(C)(COC(=O)CCCCCCCCCCCCCCCCC)C(=O)Oc1ccc(CC(=O)OCCSSCCOC(=O)NCCN(CC)CC)cc1] |
| compound 34 | 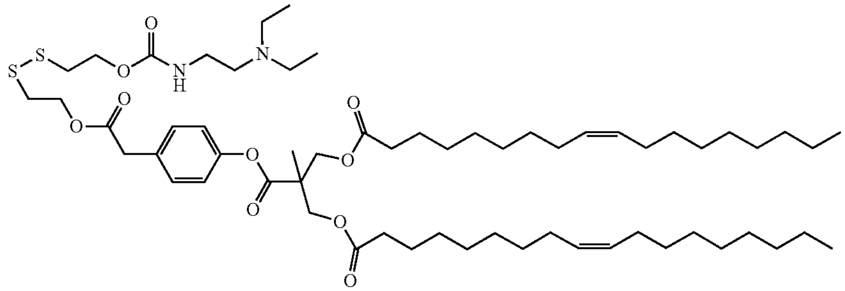 [SMILES: CCCCCCCC/C=C\CCCCCCCC(=O)OCC(C)(COC(=O)CCCCCCC/C=C\CCCCCCCC)C(=O)Oc1ccc(CC(=O)OCCSSCCOC(=O)NCCN(CC)CC)cc1] |
| compound 35 | 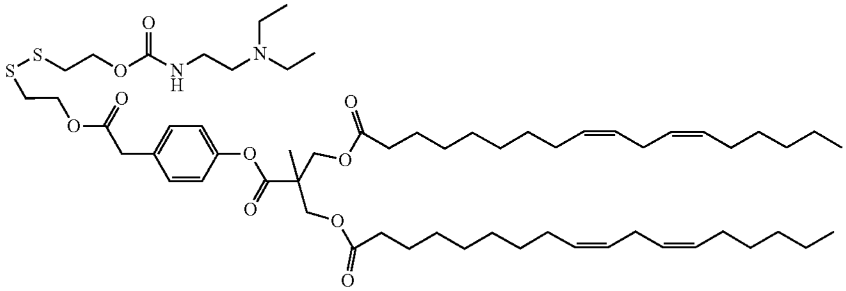 [SMILES: CCCCC/C=C\C/C=C\CCCCCCCC(=O)OCC(C)(COC(=O)CCCCCCC/C=C\C/C=C\CCCCC)C(=O)Oc1ccc(CC(=O)OCCSSCCOC(=O)NCCN(CC)CC)cc1] |
| compound 36 | 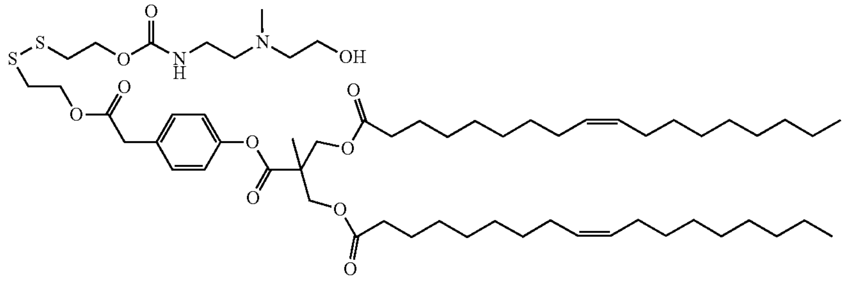 [SMILES: CCCCCCCC/C=C\CCCCCCCC(=O)OCC(C)(COC(=O)CCCCCCC/C=C\CCCCCCCC)C(=O)Oc1ccc(CC(=O)OCCSSCCOC(=O)NCCN(C)CCO)cc1] |
| compound 37 | 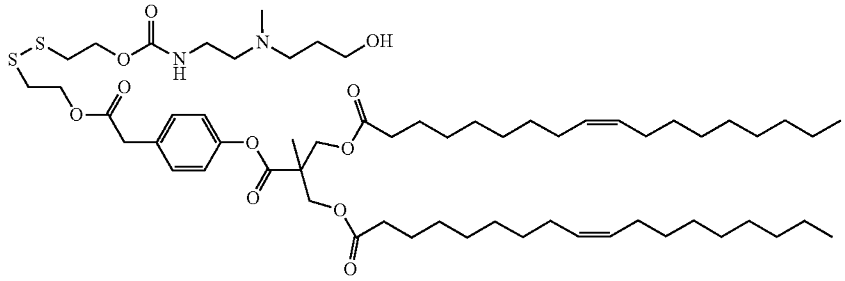 [SMILES: CCCCCCCC/C=C\CCCCCCCC(=O)OCC(C)(COC(=O)CCCCCCC/C=C\CCCCCCCC)C(=O)Oc1ccc(CC(=O)OCCSSCCOC(=O)NCCN(C)CCCO)cc1] |

TABLE 1-continued
| name | structure |
| --- | --- |
| compound 38 | 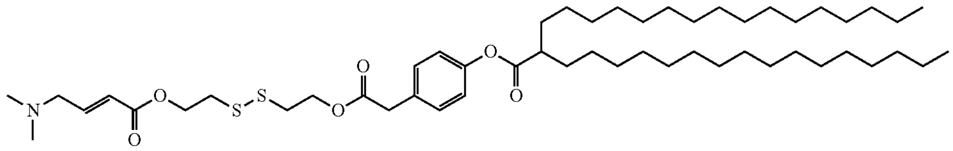 [SMILES: CCCCCCCCCCCCCCCCC(CCCCCCCCCCCCCCCC)C(=O)Oc1ccc(CC(=O)OCCSSCCOC(=O)/C=C/CN(C)C)cc1] |
| compound 39 | 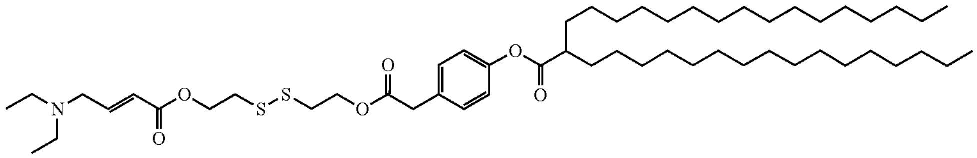 [SMILES: CCCCCCCCCCCCCCCCC(CCCCCCCCCCCCCCCC)C(=O)Oc1ccc(CC(=O)OCCSSCCOC(=O)/C=C/CN(CC)CC)cc1] |
| compound 40 | 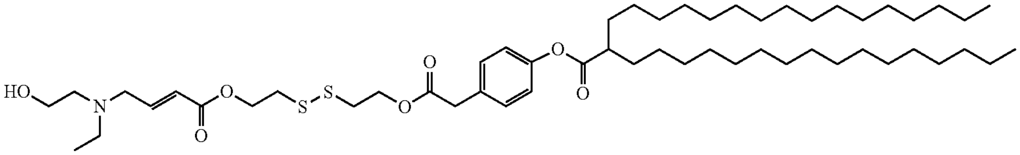 [SMILES: CCCCCCCCCCCCCCCCC(CCCCCCCCCCCCCCCC)C(=O)Oc1ccc(CC(=O)OCCSSCCOC(=O)/C=C/CN(CC)CCO)cc1] |
| compound 41 | 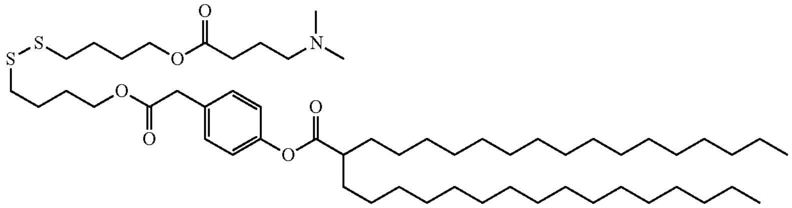 [SMILES: CCCCCCCCCCCCCCCCC(CCCCCCCCCCCCCCCC)C(=O)Oc1ccc(CC(=O)OCCCCSSCCCCOC(=O)CCCN(C)C)cc1] |
| compound 42 | 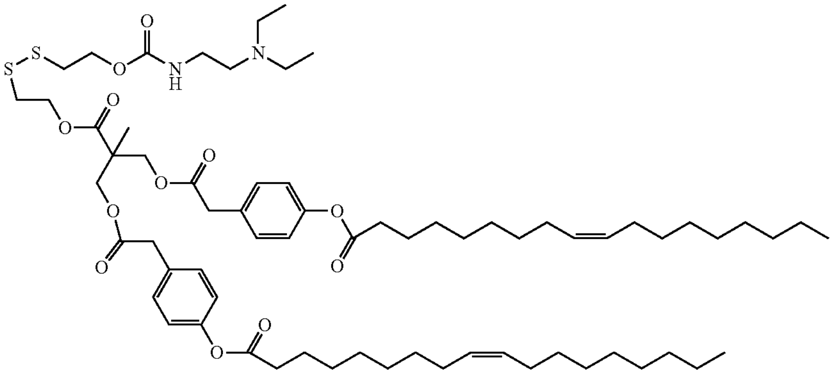 [SMILES: CCCCCCCC/C=C\CCCCCCCC(=O)Oc1ccc(CC(=O)OCC(C)(COC(=O)Cc2ccc(OC(=O)CCCCCCC/C=C\CCCCCCCC)cc2)C(=O)OCCSSCCOC(=O)NCCN(CC)CC)cc1] |
| compound 43 | 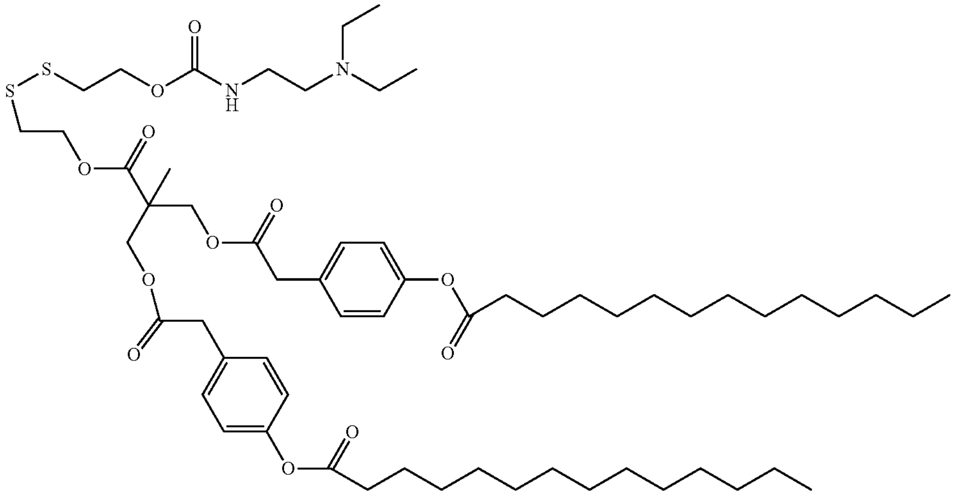 [SMILES: CCCCCCCCCCCCCC(=O)Oc1ccc(CC(=O)OCC(C)(COC(=O)Cc2ccc(OC(=O)CCCCCCCCCCCCC)cc2)C(=O)OCCSSCCOC(=O)NCCN(CC)CC)cc1] |

TABLE 1-continued

| name | structure |
| --- | --- |
| compound 44 | 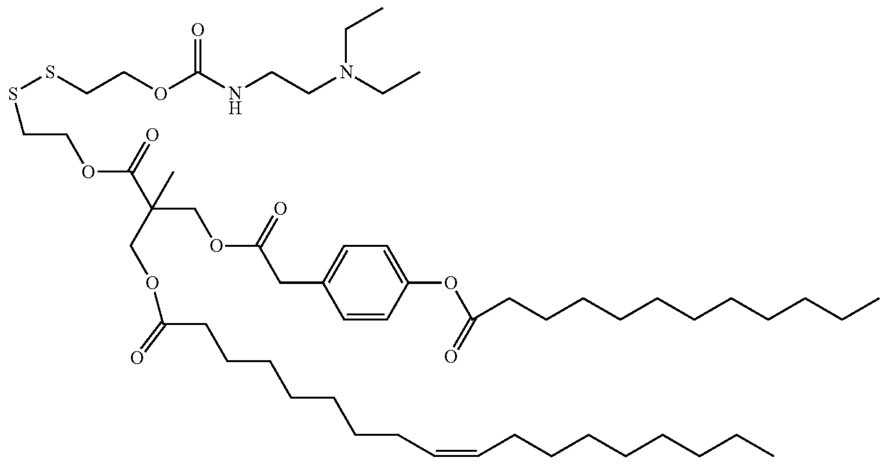 [SMILES: CCCCCCCC/C=C\CCCCCCCC(=O)OCC(C)(COC(=O)Cc1ccc(OC(=O)CCCCCCCCCCC)cc1)C(=O)OCCSSCCOC(=O)NCCN(CC)CC] |
| compound 45 | 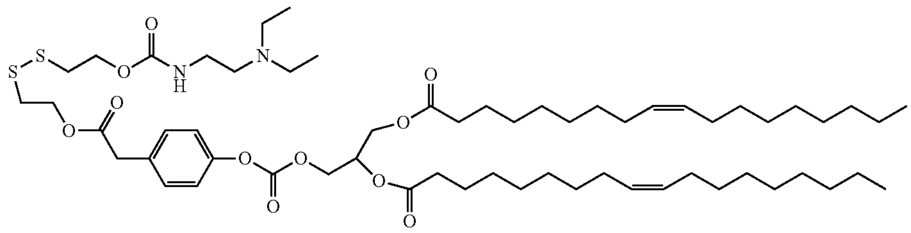 [SMILES: CCCCCCCC/C=C\CCCCCCCC(=O)OCC(COC(=O)Oc1ccc(CC(=O)OCCSSCCOC(=O)NCCN(CC)CC)cc1)OC(=O)CCCCCCC/C=C\CCCCCCCC] |
| compound 46 | 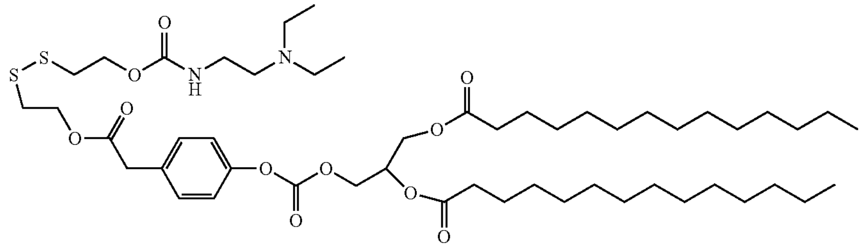 [SMILES: CCCCCCCCCCCCCC(=O)OCC(COC(=O)Oc1ccc(CC(=O)OCCSSCCOC(=O)NCCN(CC)CC)cc1)OC(=O)CCCCCCCCCCCCC] |

The production method of the cationic lipid (1) of the present invention is described now.

The cationic lipid (1) in the present invention has an —S—S— (disulfide) bond. Therefore, the production method of the cationic lipid (1) of the present invention includes (A) a method including producing a thiol represented by X—($R^1$-$L^1$)$_k$-$R^X$—SH and a thiol represented by HS—$R^y$-$L^2$-$R^2$—Y, and subjecting them to oxidation and coupling, (B) a method including sequentially bonding necessary parts to a starting compound containing an —S—S— bond to finally obtain the cationic lipid (1) of the present invention, and the like. The production method of the cationic lipid (1) of the present invention is preferably the method of (B).

The method of (B) is described below; however, the production method of the cationic lipid (1) of the present invention is not limited thereto.

The raw materials, reagents, and compounds used and obtained in each step of the following production methods may each form a salt. Examples of such salt include those similar to the salts in the compounds of the aforementioned present invention.

When the compound obtained in each step is a free compound, it can be converted into the desired salt by a known method. Conversely, when the compound obtained in each step is a salt, it can be converted into the free form or another type of desired salt by a known method.

The compound obtained in each step can be used in the next reaction either as a reaction solution or after being obtained as a crude product. Alternatively, the compound obtained in each step can be appropriately purified by a general purification method, for example, extraction from reaction mixture, recrystallization, adsorption, reprecipitation, column chromatography, ion exchange chromatography and the like.

When the raw materials and reagent compounds for each step are commercially available, the commercially available products can be used as is.

In the reactions of each step, the reaction time is generally 1 min to 48 hr, preferably 10 min to 22 hr, unless otherwise specified.

In the reactions of each step, the reaction temperature is generally −78° C. to 300° C., preferably −78° C. to 150° C.

In the reactions of each step, the reagent is used in an amount of 0.5 equivalents to 20 equivalents, preferably 0.8 equivalents to 8 equivalents 0.5 to 20 equivalents, preferably 0.8 to 8 equivalents, relative to the substrate, unless otherwise specified. When a reagent is used as a catalyst, the reagent is used in an amount of 0.001 equivalents-1 equivalents, preferably 0.01 equivalents-0.4 equivalents, relative to the substrate. When a reagent also serves as a reaction solvent, the reagent is used in an amount equal to the solvent.

In the reactions of each step, unless otherwise specified, the reactions are performed without solvent or by dissolving or suspending in a suitable solvent. Specific examples of solvents include those described in the Examples, methanol, ethanol, isopropanol, tert-butyl alcohol, tetrahydrofuran, toluene, cyclohexane, hexane, heptane, N,N-dimethylformamide, N-methylpyrrolidone, chloroform, dichloromethane, acetonitrile, dimethylsulfoxide, ethyl acetate, acetone, water, and the like. Two or more of the above solvents may be mixed in an appropriate ratio.

When a base is used in the reaction of each step, examples thereof include the bases described in the Examples, sodium hydroxide, potassium hydroxide, sodium carbonate, calcium carbonate, sodium hydrogen carbonate, triethylamine, N,N-diisopropylethylamine, pyridine, 4-dimethylaminopyridine, 1,8-diazabicyclo[5.4.0]-7-undecene (DBU), imidazole, piperidine, sodium ethoxide, potassium tert-butoxide, sodium tert-butoxide, lithium hydride and the like.

When a acid or acidic catalyst is used in the reaction of each step, examples thereof include the acids and acidic catalysts described in the Examples, hydrochloric acid, sulfuric acid, nitric acid, phosphoric acid, acetic acid, trifluoroacetic acid, methanesulfonic acid, p-toluenesulfonic acid, pyridinium p-toluenesulfonate, boron trifluoride diethyl ether complex, and the like.

In each step, the protection or deprotection reaction of the functional group is performed using known reagents and methods (e.g., reagents and methods described in GREENE'S PROTECTIVE GROUPS IN ORGANIC SYNTHESIS, 4th Edition, WILEY-INTERSCIENCEM) or in accordance with the methods described in the Examples.

Protective groups for hydroxyl groups of alcohols and phenolic hydroxyl groups include, for example, ether-type protective groups such as tetrahydropyranyl ether, methoxymethyl ether, benzyl ether, p-methoxybenzyl ether, t-butyldimethylsilyl ether, t-butyldiphenylsilyl ether and the like; carboxylate-type protective groups such as acetate and the like; sulfonate-type protective groups such as methanesulfonate and the like; and carbonate-type protective groups such as t-butyl carbonate and the like.

Protective groups can be removed by known methods such as using acid, base, ultraviolet light, hydrazine, phenylhydrazine, sodium N-methyldithiocarbamate, tetrabutylammonium fluoride, palladium acetate, trialkylsilyl halide, reduction method, and the like.

When a carbonation reaction or carbamation reaction is performed in each step, reagents to be used include N,N'-disuccinimidyl carbonate (DSC), 4-nitrophenyl chloroformate (pNPCl), and bases (basic salts, organic bases, and the like). When carbonation is performed, an additive such as 4-dimethylaminopyridine (DMAP) and the like may be further added.

In each step, when a mesylation reaction is performed, the reagents to be used are methanesulfonyl chloride and a base (basic salts, organic bases, and the like).

In each step, when an esterification reaction, an amidation reaction, or a urea reaction is performed, the reagents to be used include activated carboxylic acids such as acyl halides such as acid chlorides, acid anhydrides, and activated esters. Examples of activator for carboxylic acid include carbodiimide-based condensing agents such as 1-ethyl-3-(3-dimethylaminopropyl)carbodiimide hydrochloride (EDC), triazine-based condensing agents such as 4-(4,6-dimethoxy-1,3,5-triazin-2-yl)-4-methylmorpholinium chloride n-hydrate (DMT-MM), O-(7-azabenzotriazol-1-yl)-N,N,N',N'-tetramethyluronium hexafluorophosphate (HATU), and combinations thereof. When a carbodiimide-based condensing agent is used, additives such as 1-hydroxybenzotriazole (HOBt), N-hydroxysuccinimide (HOSu), 4-dimethylaminopyridine (DMAP) and the like may be further added to the reaction.

In each step, when nucleophilic substitution reactions such as amination and the like are performed, a nucleophile (such as amines) and a base (such as basic salts or organic bases) are used as reagents. Additives such as potassium iodide (KI), tetrabutylammonium iodide (TBAI) and the like may also be added to the reaction.

Cationic lipid (1) can be produced, for example, by the following production methods. In addition, salts of the cationic lipid (1) can be obtained by appropriate mixing with an inorganic acid or an organic acid.

Production method A: k=1, l=0, m=0, n=0, $R^x$ and $R^y$ are both ethylene groups

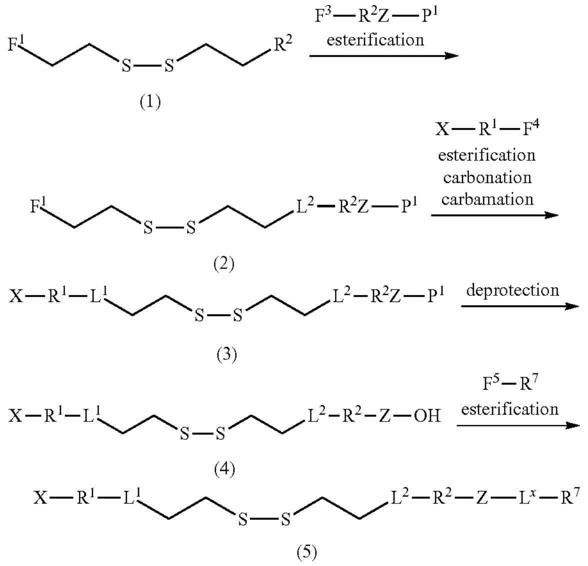

Production method B: k=1, l=0, m=1, n=1, $R^x$ and $R^y$ are both ethylene groups
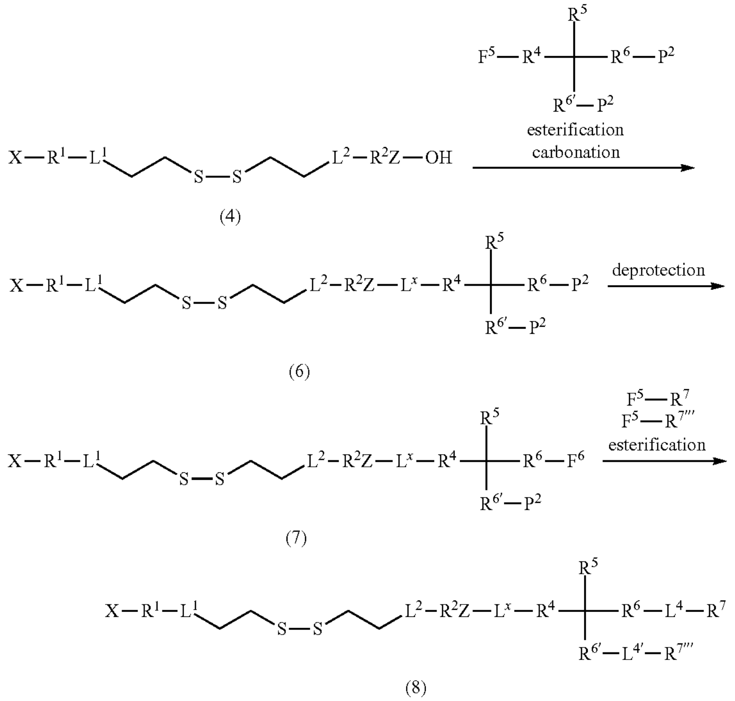
(4)
(6)
(7)
(8)
Production method C: k=1, l=1, m=0, n=0, $R^x$ and $R^y$ are both ethylene groups, $S^1$ is hydrogen or alkyl group
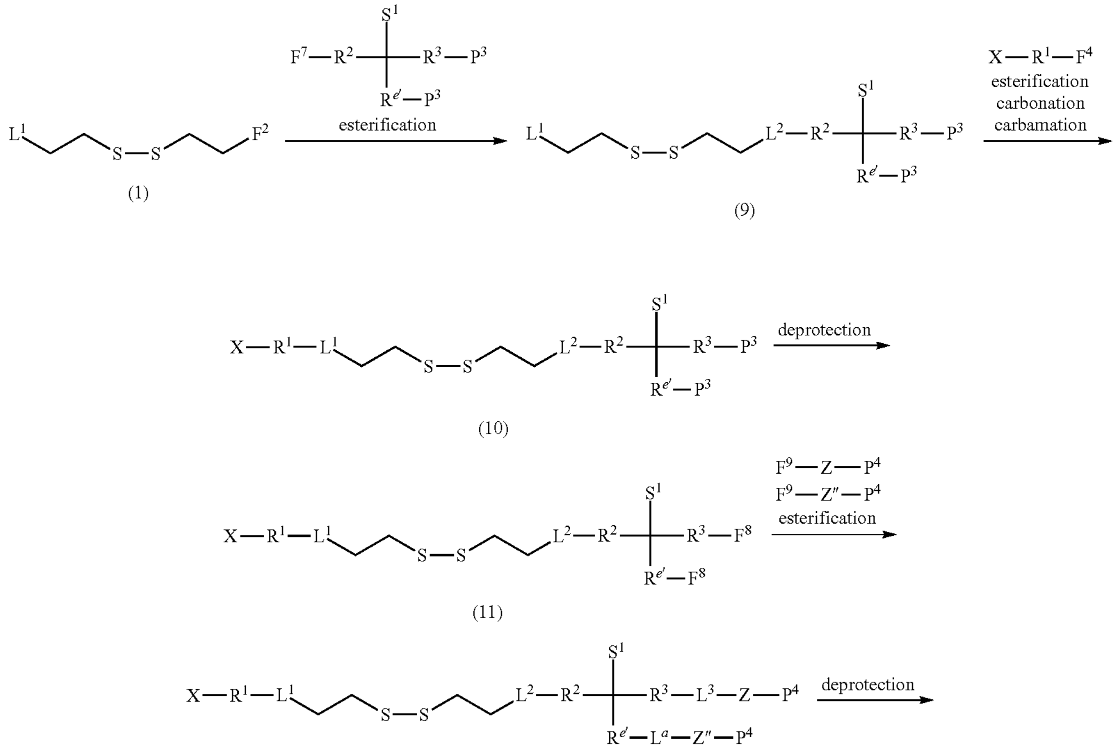
(1)
(9)
(10)
(11)
(12)

-continued

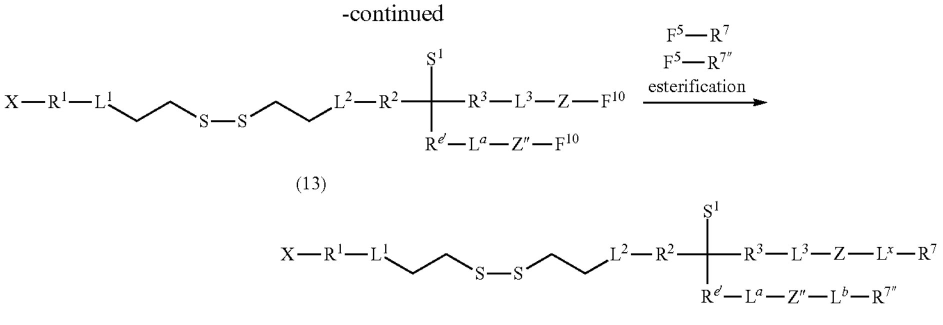

(13)

(14)

Production method D: k=0, l=0, m=0, n=0, $R^x$ and $R^y$ are both ethylene groups

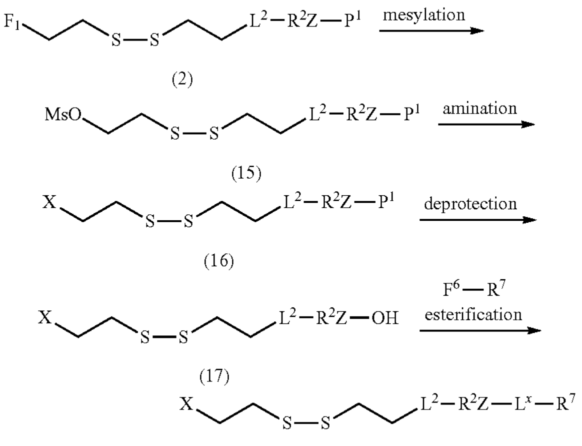

(2)

(15)

(16)

(17)

(18)

In the above-mentioned formula, $F^1$ to $F^{10}$ each independently represent a reactive functional group, and $P^1$ to $P^4$ each independently represent a protecting group.

Specific production methods are described in Examples 1 to 46 described later. Those of ordinary skill in the art can produce a desired cationic lipid (1) by appropriately selecting the starting material and performing the reaction according to the methods described in Examples 1 to 46.

The lipid membrane structure of the present invention is now described.

The lipid membrane structure of the present invention contains the cationic lipid (1) of the present invention as a membrane-constituting material (constituent lipid). As used herein, the "lipid membrane structure" in the present invention means a structure having a membrane structure in which the hydrophilic groups of amphipathic lipid are arranged in the interface, facing the aqueous phase side. The "amphiphilic lipid" means a lipid having both a hydrophilic group and a hydrophobic group. Examples of the amphiphilic lipid include cationic lipid, phospholipid, and the like.

While the form of the lipid membrane structure of the present invention is not particularly limited, for example, liposome (e.g., monolayer liposome, multilayer liposome, and the like), O/W emulsion, W/O emulsion, spherical micelle, worm-like micelle, lipid nano particles (Lipid Nanoparticle, sometimes to be abbreviated as "LNP" in the present specification), disordered layer structure, and the like can be mentioned as a form of the cationic lipid (1) of the present invention dispersed in an aqueous solvent. The lipid membrane structure of the present invention is preferably LNP.

The lipid membrane structure of the present invention may further contain other constituent components in addition to the cationic lipid (1) of the present invention. Examples of other constituent component include lipid (phospholipid (phosphatidylinositol, phosphatidylethanolamine, phosphatidylserine, phosphatidic acid, phosphatidylglycerol, phosphatidylcholine, and the like), glycolipid, peptide lipid, cholesterol, cationic lipid other than the cationic lipid (1) of the present invention, PEG lipid, and the like), surfactant (e.g., 3-[(3-cholamidopropyl)dimethylammonio]propanesulfonate, sodium cholate salt, octylglycoside, N-D-gluco-N-methylalkanamides, and the like), polyethylene glycol, protein, and the like. The content of other constituent components in the lipid membrane structure of the present invention is preferably 5 to 95 mol %, more preferably 10 to 90 mol %, further preferably 30 to 80 mol %, with respect to all constituent components in the lipid membrane structure of the present invention (i.e., total of the cationic lipid (1) of the present invention and other constituent components).

While the content of the cationic lipid (1) of the present invention in the lipid membrane structure of the present invention is not particularly limited, when the lipid membrane structure is used as the below-mentioned nucleic acid-introducing agent, the cationic lipid (1) of the present invention is contained in an amount sufficient for introducing a nucleic acid. For example, the content of the cationic lipid (1) of the present invention in the lipid membrane structure of the present invention is preferably 5 to 100 mol %, more preferably 10 to 90 mol %, further preferably 20 to 70 mol %, with respect to all lipids in the lipid membrane structure of the present invention.

The lipid membrane structure of the present invention can be prepared by dispersing the cationic lipid (1) of the present invention and other constituent components (lipid and the like) in a suitable solvent or dispersion medium, for example, aqueous solvent and alcoholic solvent, and performing an operation to induce organization as necessary.

Examples of the "operation to induce organization" include, but are not limited to, methods known per se such as ethanol dilution method using a micro flow path or vortex, simple hydration method, sonication, heating, vortex, ether injecting method, French press method, cholic acid method, $Ca^{2+}$ fusion method, freeze-thaw method, reversed-phase evaporation method, and the like.

A nucleic acid can be introduced into a cell in vivo and/or in vitro by encapsulating the nucleic acid in the lipid membrane structure containing the cationic lipid of the present invention and contacting the lipid membrane structure with the cell. Therefore, the present invention provides a nucleic acid-introducing agent, containing the above-mentioned cationic lipid (1) or lipid membrane structure of the present invention.

The nucleic acid-introducing agent of the present invention can introduce any nucleic acid into a cell. While any of single-stranded to triple-stranded nucleic acids can be used, single-stranded or double-strand one is preferred.

Examples of the nucleic acid include, but are not limited to, DNA, RNA, chimera nucleic acid of RNA, DNA/RNA hybrid, and the like. Nucleic acids other than DNA, RNA, chimera nucleic acid of RNA, and DNA/RNA hybrid may also be used (hereinafter to be indicated as "other nucleic acid"). Examples of other nucleic acid include nucleotides having N-glycoside of a purine or pyrimidine base, oligomers having a non-nucleotide backbone (e.g., commercially available peptide nucleic acid (PNA) and the like), oligomers containing a special bond (said oligomer containing a nucleotide having a base pairing or a configuration permitting attachment of base, which are found in DNA and RNA), and the like.

Furthermore, the nucleic acid may also be, for example, a nucleic acid added with known modification, a nucleic acid with a label known in the pertinent field, a nucleic acid with a cap, a methylated nucleic acid, a nucleic acid in which one or more natural nucleotides substituted by an analog, a nucleic acid with intramolecularly crosslinked nucleotide, a nucleic acid with a non-charge bond (e.g., methylphosphonate, phosphotriester, phosphoramidate, carbamate, and the like), a nucleic acid with a charged bond or sulfur-containing bond (e.g., phosphorothioate, phosphorodithioate, and the like), for example, a nucleic acid with a side chain group such as protein (nuclease, nuclease inhibitor, toxin, antibody, signal peptide, poly-L-lysine, and the like), sugar (e.g., monosaccharide and the like), and the like, a nucleic acid containing an intercalating compound (e.g., acridine, psoralen, and the like), a nucleic acid with a chelate compound (e.g., metal, radioactive metal, boron, oxidative metal, and the like), a nucleic acid containing an alkylating agent, a nucleic acid with a modified bond (e.g., a anomer-type nucleic acid and the like), or the like.

The type of the DNA that can be used in the present invention is not particularly limited, and can be selected as appropriate according to the purpose of use. Examples of the DNA include plasmid DNA, cDNA, antisense DNA, chromosomal DNA, PAC, BAC, CpG oligo, and the like. Among these, plasmid DNA, cDNA, and antisense DNA are preferred, and plasmid DNA is more preferred. Circular DNA such as plasmid DNA and the like can be digested as appropriate with restriction enzymes and the like, and also used as a linear DNA.

The type of the RNA that can be used in the present invention is not particularly limited, and can be selected as appropriate according to the purpose of use. Examples of the RNA include siRNA, miRNA, shRNA, antisense RNA, messenger RNA (mRNA), single strand RNA genome, double strand RNA genome, RNA replicon, transfer RNA, ribosomal RNA, and the like. Among these, siRNA, miRNA, shRNA, mRNA, antisense RNA, and RNA replicon are preferred.

The nucleic acid used in the present invention is preferably purified by a method generally used by those of ordinary skill in the art.

The nucleic acid-introducing agent of the present invention encapsulating a nucleic acid can be administered in vivo for the purpose of, for example, prevention and/or treatment of diseases. Therefore, the nucleic acid to be used in the present invention is preferably one having a preventive and/or therapeutic activity against a given disease (prophylactic/therapeutic nucleic acid). Examples of such nucleic acid include nucleic acids used for so-called gene therapy, and the like.

The lipid membrane structure of the present invention encapsulating a nucleic acid (i.e., the nucleic acid-introducing agent of the present invention encapsulating the nucleic acid) can be formed by achieving the co-presence of the nucleic acid of interest and the constituent components (lipid and the like) of the lipid membrane structure of the present invention when forming the lipid membrane structure of the present invention.

For example, when the lipid membrane structure of the present invention is formed as a liposome by an ethanol dilution method, an aqueous nucleic acid solution and an ethanol solution of the constituent components (lipid and the like) of the lipid membrane structure are vigorously mixed in a vortex, micro flow path, or the like, and the obtained mixture is diluted with an appropriate buffer, whereby the lipid membrane structure of the present invention encapsulating a nucleic acid (i.e., the nucleic acid-introducing agent of the present invention encapsulating a nucleic acid) can be formed.

In addition, when the lipid membrane structure of the present invention is formed as a liposome by a simple hydration method, the constituent components of the lipid membrane structure are dissolved in an appropriate organic solvent, and the solution is placed in a glass container and dried under reduced pressure to evaporate the solvent, whereby a lipid thin film is obtained. Then, to the obtained lipid thin film is added an aqueous nucleic acid solution and after hydration, the mixture is sonicated by a sonicator, whereby the lipid membrane structure of the present invention encapsulating the nucleic acid (i.e., the nucleic acid-introducing agent of the present invention encapsulating the nucleic acid) can be formed.

One form of the lipid membrane structure of the present invention encapsulating a nucleic acid is LNP encapsulating the nucleic acid by forming an electrostatic complex between the nucleic acid and a cationic lipid. This LNP can be used for a drug delivery system for selectively delivering a nucleic acid and the like into a particular cell, and is useful for, for example, DNA vaccines, gene therapy drugs for tumor, nucleic acid pharmaceutical products (pharmaceutical compositions) that suppress expression of target genes by utilizing RNA interference, and the like, based on introduction of antigen gene into dendritic cells.

The particle size of the lipid membrane structure of the present invention encapsulating a nucleic acid is not particularly limited, and is preferably 10 nm to 500 nm, more preferably 30 nm to 300 nm. The particle size can be measured by using a particle size distribution measuring device such as Zetasizer Nano (Malvern) and the like. The particle size of the lipid membrane structure can be appropriately adjusted by the method for preparing the lipid membrane structure.

The zeta potential of the lipid membrane structure of the present invention encapsulating a nucleic acid is not particularly limited and preferably −15 to +15 mV, more preferably −5 to +15 mV. In conventional gene transfer, particles electrically charged to have a plus surface potential have been mainly used. This is useful as a method for promoting electrostatic interactions with negatively-charged heparin sulfate on the cell surface to enhance uptake into cells. However, the positive surface charge may suppress (a) release of nucleic acid from the carrier in the cell due to the interaction with a nucleic acid to be delivered, or (b) protein synthesis due to the interaction between mRNA and a nucleic acid to be delivered. This problem can be solved by adjusting the zeta potential to fall within the above-mentioned range. The zeta potential can be measured using a zeta potential measuring apparatus such as Zetasizer Nano and the like. The zeta potential of the lipid membrane structure can be adjusted by the composition of the constituent component of the lipid membrane structure containing the cationic lipid (1) of the present invention.

The lipid membrane surface pKa (hereinafter sometimes to be abbreviated as "Liposomal pKa") of the lipid membrane structure of the present invention is not particularly limited, and the pKa is preferably 5.0 to 9.0, further preferably 5.3 to 8.5. Liposomal pKa is used as an index indicating the susceptibility of protonation of a lipid membrane structure which is incorporated by endocytosis in an endosome in a weakly acidic environment inside the endosome. As described in non-Patent Literatures 2 and 3, to escape from an endosome and deliver a nucleic acid into a cytoplasm, it is important to set the Liposomal pKa to a value preferable for the escape from the endosome. By adjusting the Liposomal pKa to fall within the above ranges, a nucleic acid can be efficiently delivered into a cytoplasm. The Liposomal pKa can be appropriately adjusted by selecting the cationic lipid (1) of the present invention used as the constituent component of a lipid membrane structure.

The nucleic acid-introducing agent of the present invention encapsulating a nucleic acid is brought into contact with cells to introduce the nucleic acid into the cells. The kind of the cell is not particularly limited, and a prokaryotic or eukaryotic cell can be used. The cell is preferably a eukaryote cell. The kind of the eukaryote is not particularly limited and for example, vertebrates such as mammals including human (e.g., human, monkey, mouse, rat, hamster, bovine, and the like), birds (e.g., chicken, ostrich, and the like), amphibia (e.g., frog and the like), fishes (e.g., zebrafish, rice-fish, and the like) and the like, invertebrates such as insects (silk moth, moth, *Drosophila*, and the like), and the like, plants, microorganisms (e.g., yeasts), and the like can be mentioned. The cell is more preferably an animal or plant cell, further preferably a mammalian cell. The cell may be a culture cell line including a cancer cell, or a cell isolated from an individual or tissue, or a cell of a tissue or tissue piece. The cell may be an adherent cell or a non-adherent cell.

The step of contacting the nucleic acid-introducing agent of the present invention encapsulating a nucleic acid with a cell in vitro is specifically described below.

Cells are suspended in a suitable medium several days before contact with a nucleic acid-introducing agent encapsulating a nucleic acid, and cultured under appropriate conditions. At the time of contact with the nucleic acid-introducing agent, the cells may or may not be in a proliferative phase.

The culture medium at the time of contact of the cell and the nucleic acid-introducing agent encapsulating a nucleic acid of the present invention may be a serum-containing medium or a serum-free medium. The serum concentration of the medium is preferably not more than 30 wt %, more preferably not more than 20 wt %. When the medium contains excess proteins such as serum and the like, the contact between the nucleic acid-introducing agent and the cell may be inhibited.

The cell density at the time of contact of the cell and the nucleic acid-introducing agent of the present invention encapsulating a nucleic acid is not particularly limited, and can be appropriately determined in consideration of the kind of the cell and the like. It is generally within the range of $1\times10^4$ to $1\times10^7$ cells/mL.

For example, a dispersion of the aforementioned nucleic acid-introducing agent of the present invention encapsulating a nucleic acid is added to cells. The amount of the dispersion to be added is not particularly limited, and can be appropriately determined in consideration of the cell number and the like. The concentration of the nucleic acid-introducing agent in the dispersion when contacting cells is not particularly limited as long as the desired introduction of the nucleic acid into the cells can be achieved. The lipid concentration in the dispersion is generally 1 to 100 nmol/ml, preferably 10 to 50 nmol/ml, and the concentration of the nucleic acid in the dispersion is generally 0.01 to 100 μg/ml, preferably 0.1 to 10 μg/ml.

After the aforementioned dispersion is added to cells, the cells are cultured. The temperature, humidity and $CO_2$ concentration during culturing are appropriately determined in consideration of the kind of the cell. When the cell is derived from a mammal, generally, the temperature is about 37° C., the relative humidity is about 95%, and the $CO_2$ concentration is about 5 vol %. While the culture time can also be appropriately determined in consideration of the conditions such as the kind of the cell and the like, it is generally a range of 0.1 to 76 hr, preferably a range of 0.2 to 24 hr, more preferably a range of 0.5 to 12 hr. When the above-mentioned culture time is too short, the nucleic acid is not sufficiently introduced into the cells, and when the culture time is too long, the cells may become weak.

By the above-mentioned culture, a nucleic acid is introduced into cells. The culture is further continued preferably by exchanging the medium with a fresh medium, or adding a fresh medium to the medium. When the cell is a mammal-derived cell, the fresh medium preferably contains a serum or nutrition factor.

A nucleic acid can be introduced into cells not only outside the body (in vitro) but also in the body (in vivo) by using the nucleic acid-introducing agent of the present invention encapsulating a nucleic acid. That is, by administration of the nucleic acid-introducing agent to a subject, the nucleic acid-introducing agent reaches and contacts with the target cells, and a nucleic acid is introduced into the cells in vivo. The subject to which the nucleic acid-introducing agent can be administered is not particularly limited and, for example, vertebrates such as mammals (e.g., human, monkey, mouse, rat, hamster, bovine, and the like), birds (e.g., chicken, ostrich, and the like), amphibia (e.g., frog and the like), fishes (e.g., zebrafish, rice-fish, and the like), and the like, invertebrates such as insects (e.g., silk moth, moth, *Drosophila*, and the like) and the like, plants, and the like can be mentioned. The subject of administration of the nucleic acid-introducing agent is preferably human or other mammals.

The kind of the target cell is not particularly limited, and a nucleic acid can be introduced into cells in various tissues (e.g., liver, kidney, pancreas, lung, spleen, heart, blood, muscle, bone, brain, stomach, small intestine, large intestine, skin, adipose tissue, lymph node, tumor, and the like) by using the nucleic acid-introducing agent of the present invention.

The administration method of the nucleic acid-introducing agent of the present invention encapsulating a nucleic acid to a target (e.g., vertebrate, invertebrate and the like) is not particularly limited as long as the nucleic acid-introducing agent of the present invention reaches and contacts with the target cells, and the nucleic acid can be introduced into the cell, and an administration method known per se (e.g., oral administration, parenteral administration (e.g., intravenous administration, intramuscular administration, topical administration, transdermal administration, subcutaneous administration, intraperitoneal administration, spray, and the like), and the like) can be appropriately selected in consideration of the kind of the nucleic acid to be introduced, the kind and the site of the target cell, and the like. The dose of the nucleic acid-introducing agent is not particularly limited as long as the introduction of the nucleic acid into the cells can be achieved, and can be appropriately selected in consideration of the kind of the subject of administration, the administration method, the kind of the nucleic acid to be introduced, the kind and the site of the target cell, and the like.

The cationic lipid (1) and lipid membrane structure of the present invention can also be used for introducing a compound other than nucleic acids into a cell.

A nucleic acid-introducing agent containing the cationic lipid (1) or lipid membrane structure of the present invention can be formulated according to a conventional method.

When the nucleic acid-introducing agent of the present invention is provided as a reagent for studies, the nucleic acid-introducing agent of the present invention may be provided as a sterile solution or dispersion containing the cationic lipid (1) or lipid membrane structure of the present invention, and water or other physiologically acceptable solvent (e.g., water-soluble solvent (e.g., malic acid buffer and the like), organic solvent (e.g., ethanol, methanol, DMSO, tert-butanol, and the like), or a mixture of aqueous solvent and organic solvent), or it may be provided as a nucleic acid-introducing agent free of solvent. The nucleic acid-introducing agent of the present invention may appropriately contain physiologically acceptable additives (e.g., excipient, vehicle, preservative, stabilizer, binder, and the like), which is known per se.

When the nucleic acid-introducing agent of the present invention is provide as a medicament, the nucleic acid-introducing agent of the present invention may be provided as an oral preparation (e.g., tablet, capsule, and the like) or a parenteral agent (e.g., injection, spray, and the like), which is obtained by mixing the cationic lipid (1) or lipid membrane structure of the present invention with pharmaceutically acceptable known additives (e.g., carrier, flavor, excipient, vehicle, preservative, stabilizer, binder, and the like), or may be provided as a nucleic acid-introducing agent free of known additives. The nucleic acid-introducing agent of the present invention as a medicament is preferably a parenteral agent, more preferably an injection. In addition, the nucleic acid-introducing agent of the present invention may be a preparation for adults or a preparation for children.

The nucleic acid-introducing agent of the present invention can also be provided in the form of a kit. The kit can contain, in addition to the cationic lipid (1) or lipid membrane structure of the present invention, a reagent used for the introduction of a nucleic acid. In one embodiment, the nucleic acid-introducing agent (or kit) of the present invention further contains a polycation (e.g., protamine). Using the nucleic acid-introducing agent (or kit) of the present invention in this embodiment, an electrostatic complex of a nucleic acid and a polycation (e.g., protamine) can be encapsulated in the lipid membrane structure of the present invention, whereby the nucleic acid can be more effectively introduced into cells.

The present invention provides a method for producing a cell medicine containing a cell expressing a specific gene, including contacting a cell with the nucleic acid-introducing agent of the present invention encapsulating a nucleic acid, and introducing the nucleic acid into the cell.

A cell expressing a specific gene refers to a cell in which a gene of interest is expressed by introducing a nucleic acid into the cell.

The nucleic acid-introducing agent of the present invention encapsulating a nucleic acid is brought into contact with cells in vitro to introduce the nucleic acid into the cells. By administering cells expressing a specific gene of interest to a subject, diseases can be treated or prevented. The step of contacting the nucleic acid-introducing agent of the present invention encapsulating a nucleic acid with a cell in vitro can be performed by a method similar to that in the aforementioned explanation.

The cells used in the production of cell medicines are not particularly limited as long as they are immune cells, and examples thereof include T cell, B cell, NK cell, dendritic cell, macrophage, monocyte, and the like. The T cells used in the production of cell medicines may be T cells induced to differentiate from lymphocyte precursor cells, including pluripotent cells, into T cells. Examples of lymphocyte precursor cells, including pluripotent cells, include embryonic stem cell (ES cell), induced pluripotent stem cell (iPS cell), and the like. Undifferentiated cells, such as pluripotent cell and the like, can be differentiated into T cells by a known method.

Examples of nucleic acids used in the production of cell medicines include nucleic acids encoding chimeric antigen receptor (CAR) and T cell receptor (TCR).

The nucleic acid encoding CAR used in the production of cell medicines contains an antigen-binding domain of an antibody capable of specifically recognizing the surface antigen to be recognized by the target immune cell, an extracellular hinge domain, a transmembrane domain, and an intracellular T cell signaling domain.

The nucleic acid encoding TCR used in the production of cell medicines is a nucleic acid encoding the a chain and p chain of the TCR capable of specifically recognizing the surface antigen to be recognized by the target T cell.

Examples of the type of nucleic acid encoding CAR and TCR include, but are not limited to, DNA, RNA, RNA chimeric nucleic acid, DNA/RNA hybrid, and the like.

The cell medicine contains cells expressing a specific gene, and may further contain pharmaceutically acceptable additives (e.g., carrier, excipient, vehicle, preservative, stabilizer, etc.). The cell medicine is preferably a parenteral agent, more preferably an injection.

The cell medicine can be used for the treatment or prevention of diseases such as cancer and the like. The cancer to which the medicament of the present invention is applied is not particularly limited, and examples thereof include, but are not limited to, lung cancer, breast cancer, gastric cancer, colon cancer, uterine cancer, ovarian cancer, osteosarcoma, chondrosarcoma, rhabdomyosarcoma, leiomyosarcoma, fibrosarcoma, liposarcoma, angiosarcoma, leukemia, malignant lymphoma, myeloma and the like.

The subjects to which the cell medicine can be administered are not particularly limited, and examples thereof include mammals (e.g., human, monkey, mouse, rat, hamster, bovine, etc.). The subjects to which the cell medicine can be administered are preferably humans or other mammals.

The administration method of the cell medicine is not particularly limited as long as the cell can express the gene of interest and, for example, parenteral administration (e.g., intravenous administration, intramuscular administration, topical administration, transdermal administration, subcutaneous administration, intraperitoneal administration, spray etc.) and the like can be appropriately selected in consideration of the kind of the type of the cell, target disease and the like. The dose of the cell medicine is not particularly limited as long as the cells can express the gene of interest and can be appropriately selected in consideration of the kind of the subject of administration, administration method, the type of the cell, the target disease and the like.

EXAMPLE

The Examples of the present invention are described in further detail in the following, but the present invention is not limited in any way by the Examples.

The abbreviations used in the description of Examples each mean the following.

DCM: dichloromethane
THF: tetrahydrofuran
IPA: 2-propanol
DHP: 3,4-dihydro-2H-pyran
PPTS: pyridinium p-toluenesulfonate
THP: 2-tetrahydropyranyl
DMAP: 4-dimethylaminopyridine
DMT-MM: 4-(4,6-dimethoxy-1,3,5-triazin-2-yl)-4-methylmorpholinium chloride n-hydrate
DSC: di(N-succinimidyl) carbonate
EDC: 1-(3-dimethylaminopropyl)-3-ethylcarbodiimide hydrochloride
TEA: triethylamine
TBAI: tetrabutylammonium iodide
DIPEA: N,N-diisopropylethylamine
NPM: 4-phenylmorpholine
MsCl: methanesulfonyl chloride
Ms: methanesulfonyl
pNPCl: 4-nitrophenyl chloroformate
mRNA: messenger RNA
Chol: cholesterol
DMG-PEG2k: 1,2-dimyristoyl-sn-glycero-3-methoxypolyethylene glycol (weight average molecular weight of polyethylene glycol chain: 2000)
DOPC: 1,2-dioleoyl-sn-glycero-3-phosphocholine
PBS: phosphate buffered saline
MES: 2-morpholinoethanesulfonic acid
TNS: sodium 6-(p-toluidino)-2-naphthalenesulfonate Tables 2 and 3 show the names and structures of the cationic lipids produced in the following Examples and Comparative Example. Comparative Example was produced according to the production methods of Patent Literature 3.

TABLE 2

| Ex. No. | name and structure (X, Y, Z correspond to formula (1)) | correspondence 1 with parameters in formulas (1) to (4) | correspondence 2 with parameters in formulas (1) to (4) |
| --- | --- | --- | --- |
| 1 | 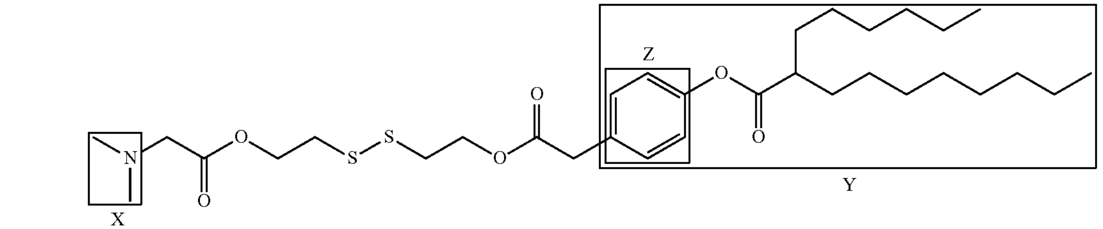 compound 1 | $R^1$: methylene<br>$R^2$: methylene<br>$R^x$: ethylene<br>$R^y$: ethylene<br>$R^7$: 1-hexylnonyl<br>$L^1$: ester<br>$L^2$: ester<br>$L^x$: ester | k = 1<br>l = 0<br>m = 0<br>n = 0<br>t = 0<br>u = 0<br>v = 0 |
| 2 | 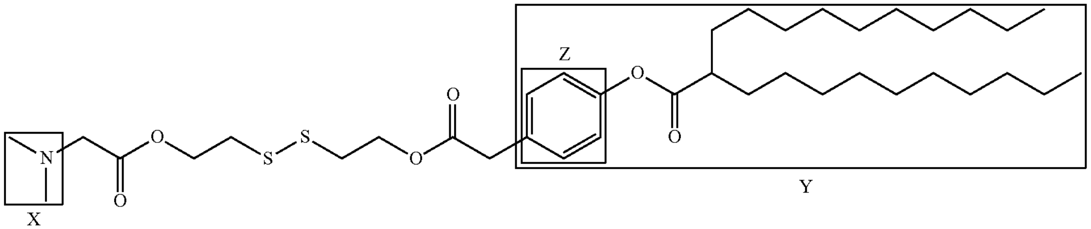 compound 2 | $R^1$: methylene<br>$R^2$: methylene<br>$R^x$: ethylene<br>$R^y$: ethylene<br>$R^7$: 1-decylundecyl<br>$L^1$: ester<br>$L^2$: ester<br>$L^x$: ester | k = 1<br>l = 0<br>m = 0<br>n = 0<br>t = 0<br>u = 0<br>v = 0 |
| 3 | 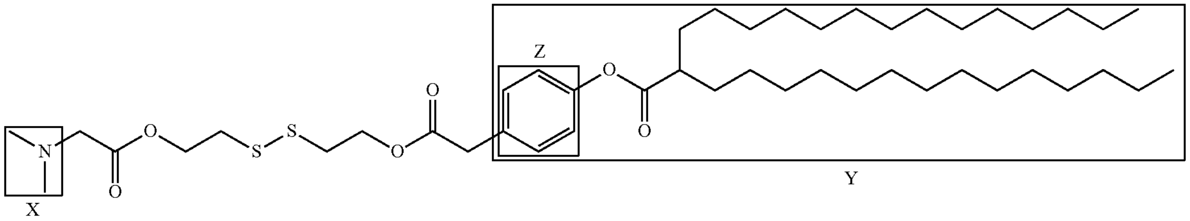 compound 3 | $R^1$: methylene<br>$R^2$: methylene<br>$R^x$: ethylene<br>$R^y$: ethylene<br>$R^7$: 1-tetradecyl-pentadecyl<br>$L^1$: ester<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 4 | 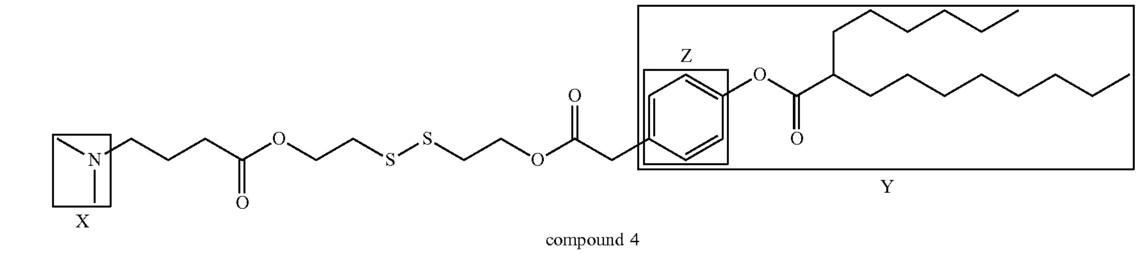<br>compound 4 | $R^1$: trimethylene<br>$R^2$: methylene<br>$R^x$: ethylene<br>$R^y$: ethylene<br>$R^7$: 1-hexylnonyl<br>$L^1$: ester<br>$L^2$: ester<br>$L^x$: ester | k = 1<br>l = 0<br>m = 0<br>n = 0<br>t = 0<br>u = 0<br>v = 0 |
| 5 | 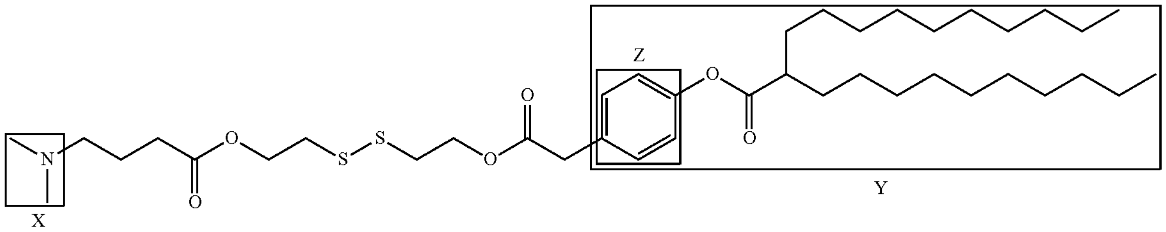<br>compound 5 | $R^1$: trimethylene<br>$R^2$: methylene<br>$R^x$: ethylene<br>$R^y$: ethylene<br>$R^7$: 1-decylundecyl<br>$L^1$: ester<br>$L^2$: ester<br>$L^x$: ester | k = 1<br>l = 0<br>m = 0<br>n = 0<br>t = 0<br>u = 0<br>v = 0 |
| 6 | 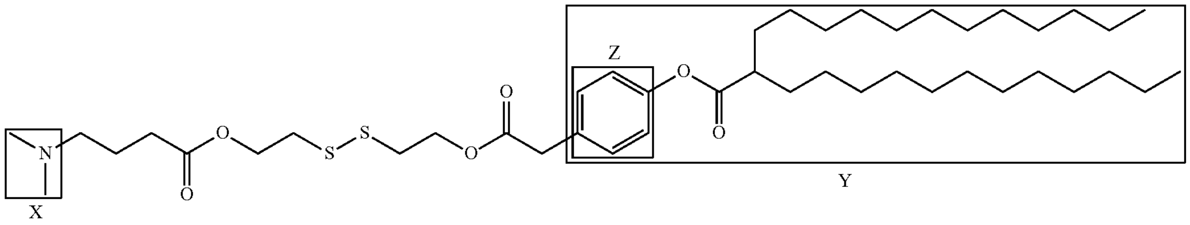<br>compound 6 | $R^1$: trimethylene<br>$R^2$: methylene<br>$R^x$: ethylene<br>$R^y$: ethylene<br>$R^7$: 1-dodecyltridecyl<br>$L^1$: ester<br>$L^2$: ester<br>$L^x$: ester | k = 1<br>l = 0<br>m = 0<br>n = 0<br>t = 0<br>u = 0<br>v = 0 |
| 7 | 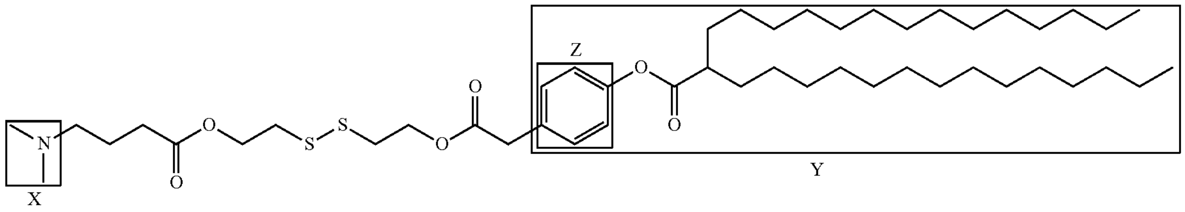 | $R^1$: trimethylene<br>$R^2$: methylene<br>$R^x$: ethylene<br>$R^y$: ethylene<br>$R^7$: 1-tetradecyl-pentadecyl<br>$L^1$: ester<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| | compound 7 | | |
| 8 | 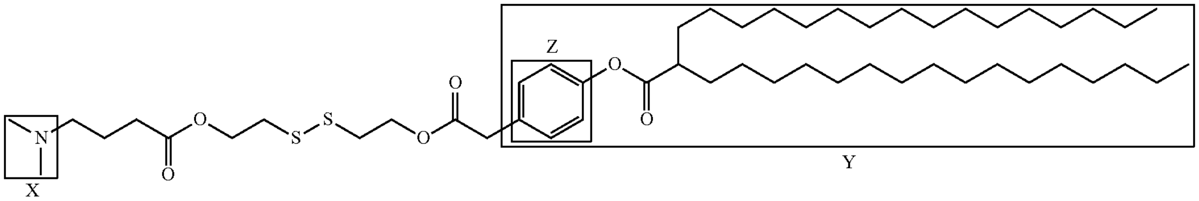<br>compound 8 | $R^1$: trimethylene<br>$R^2$: methylene<br>$R^x$: ethylene<br>$R^y$: ethylene<br>$R^7$: 1-hexadecyl-heptadecyl<br>$L^1$: ester<br>$L^2$: ester<br>$L^x$: ester | k = 1<br>l = 0<br>m = 0<br>n = 0<br>t = 0<br>u = 0<br>v = 0 |
| 9 | 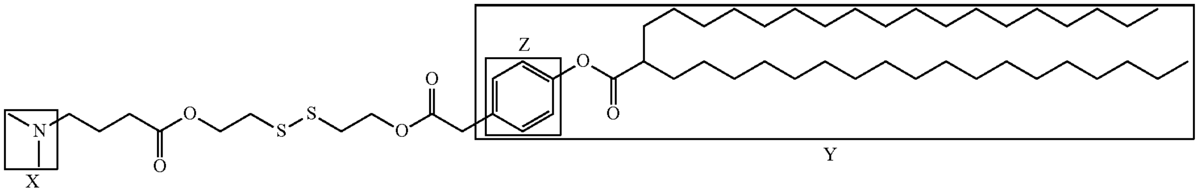<br>compound 9 | $R^1$: trimethylene<br>$R^2$: methylene<br>$R^x$: ethylene<br>$R^y$: ethylene<br>$R^7$: 1-octadecyl-nonadecyl<br>$L^1$: ester<br>$L^2$: ester<br>$L^x$: ester | k = 1<br>l = 0<br>m = 0<br>n = 0<br>t = 0<br>u = 0<br>v = 0 |
| 10 | 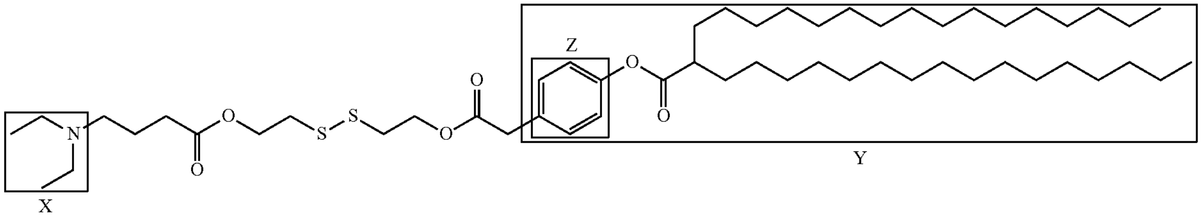<br>compound 10 | $R^1$: trimethylene<br>$R^2$: methylene<br>$R^x$: ethylene<br>$R^y$: ethylene<br>$R^7$: 1-hexadecyl-heptadecyl<br>$L^1$: ester<br>$L^2$: ester<br>$L^x$: ester | k = 1<br>l = 0<br>m = 0<br>n = 0<br>t = 0<br>u = 0<br>v = 0 |
| 11 | 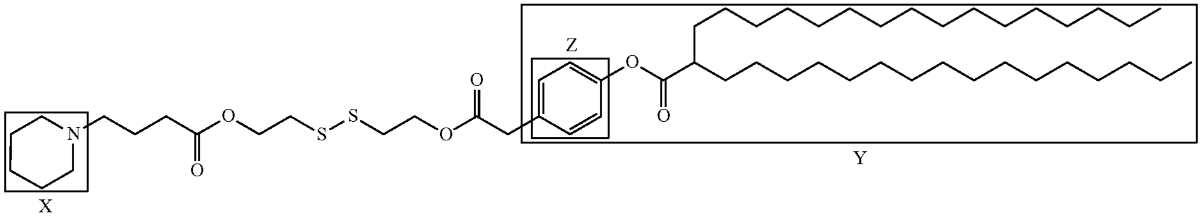<br>compound 11 | $R^1$: trimethylene<br>$R^2$: methylene<br>$R^x$: ethylene<br>$R^y$: ethylene<br>$R^7$: 1-hexadecyl-heptadecyl<br>$L^1$: ester<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 12 | 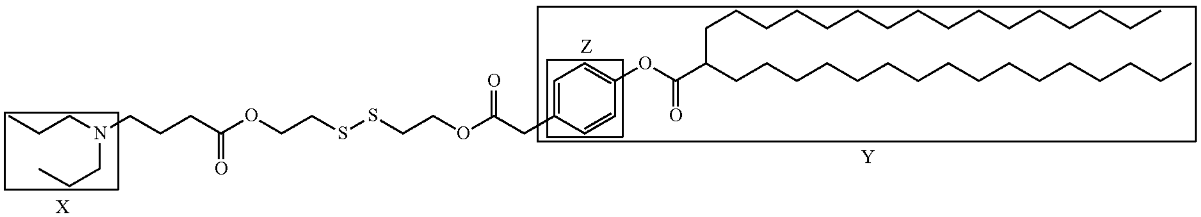<br>compound 12 | $R^1$: trimethylene<br>$R^2$: methylene<br>$R^x$: ethylene<br>$R^y$: ethylene<br>$R^7$: 1-hexadecyl-heptadecyl<br>$L^1$: ester<br>$L^2$: ester<br>$L^x$: ester | k = 1<br>l = 0<br>m = 0<br>n = 0<br>t = 0<br>u = 0<br>v = 0 |
| 13 | 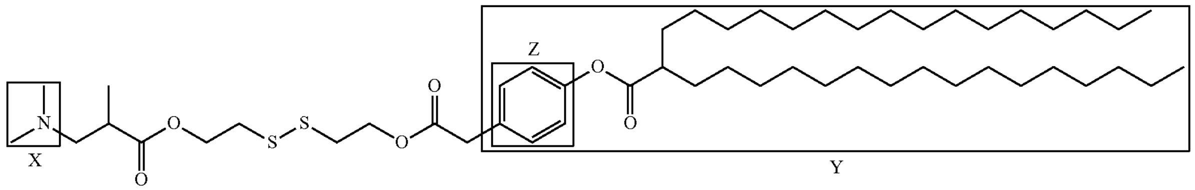<br>compound 13 | $R^1$: isopropylene<br>$R^2$: methylene<br>$R^x$: ethylene<br>$R^y$: ethylene<br>$R^7$: 1-hexadecyl-heptadecyl<br>$L^1$: ester<br>$L^2$: ester<br>$L^x$: ester | k = 1<br>l = 0<br>m = 0<br>n = 0<br>t = 0<br>u = 0<br>v = 0 |
| 14 | 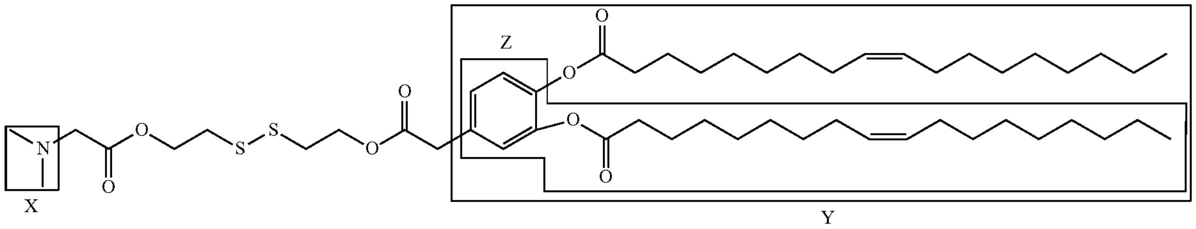<br>compound 14 | $R^1$: methylene<br>$R^2$: methylene<br>$R^x$: ethylene<br>$R^y$: ethylene<br>$R^7$: heptadecenyl<br>$R^8$: octa-decenoyloxy<br>$L^1$: ester<br>$L^2$: ester<br>$L^x$: ester | k = 1<br>l = 0<br>m = 0<br>n = 0<br>t = 0<br>u = 0<br>v = 1 |
| 15 | 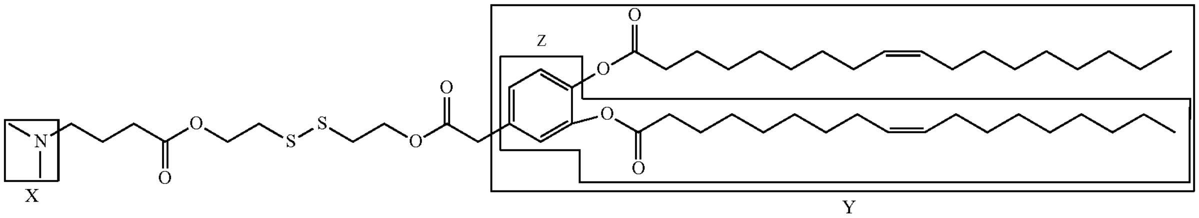 | $R^1$: trimethylene<br>$R^2$: methylene<br>$R^x$: ethylene<br>$R^y$: ethylene<br>$R^7$: heptadecenyl<br>$R^8$: octa-decenoyloxy<br>$L^1$: ester<br>$L^2$: ester<br>$L^x$: ester | k = 1<br>l = 0<br>m = 0<br>n = 0<br>t = 0<br>u = 0<br>v = 1 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| | compound 15 | | |
| 16 | 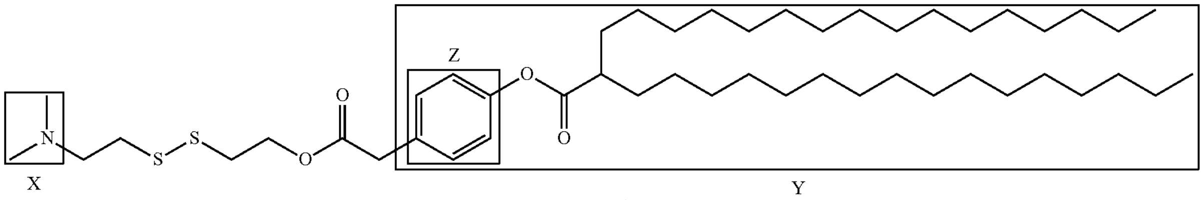 compound 16 | $R^2$: methylene<br>$R^x$: ethylene<br>$R^y$: ethylene<br>$R^7$: 1-hexadecyl-heptadecyl<br>$L^2$: ester<br>$L^x$: ester | k = 0<br>l = 0<br>m = 0<br>n = 0<br>t = 0<br>u = 0<br>v = 0 |
| 17 | 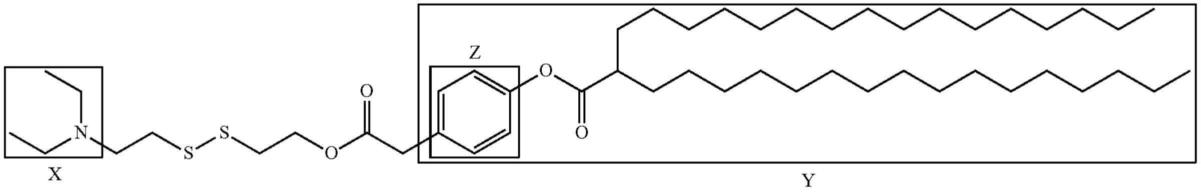 compound 17 | $R^2$: methylene<br>$R^x$: ethylene<br>$R^y$: ethylene<br>$R^7$: 1-hexadecyl-heptadecyl<br>$L^2$: ester<br>$L^x$: ester | k = 0<br>l = 0<br>m = 0<br>n = 0<br>t = 0<br>u = 0<br>v = 0 |
| 18 | 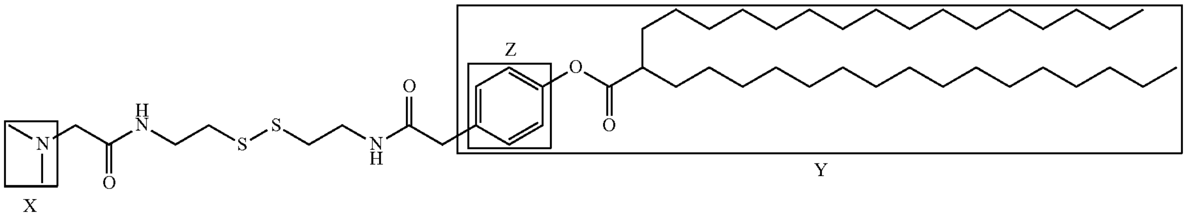 compound 18 | $R^1$: methylene<br>$R^2$: methylene<br>$R^x$: ethylene<br>$R^y$: ethylene<br>$R^7$: 1-hexadecyl-heptadecyl<br>$L^1$: amide<br>$L^2$: amide<br>$L^x$: ester | k = 1<br>l = 0<br>m = 0<br>n = 0<br>t = 0<br>u = 0<br>v = 0 |
| 19 | 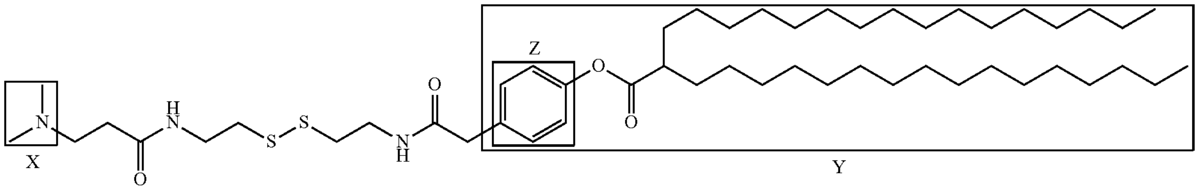 compound 19 | $R^1$: ethylene<br>$R^2$: methylene<br>$R^x$: ethylene<br>$R^y$: ethylene<br>$R^7$: 1-hexadecyl-heptadecyl<br>$L^1$: amide<br>$L^2$: amide<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 20 | 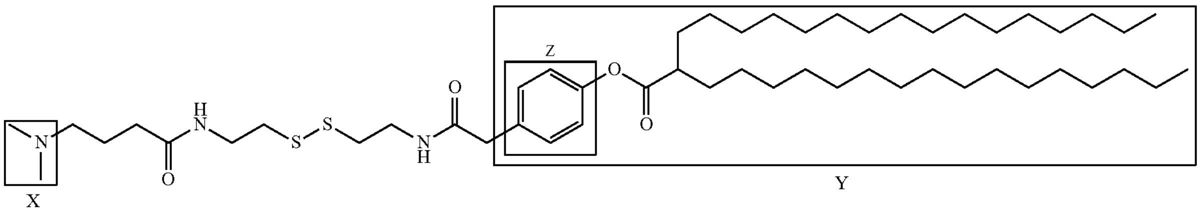<br>compound 20 | $R^1$: trimethylene<br>$R^2$: methylene<br>$R^x$: ethylene<br>$R^y$: ethylene<br>$R^7$: 1-hexadecyl-heptadecyl<br>$L^1$: amide<br>$L^2$: amide<br>$L^x$: ester | k = 1<br>l = 0<br>m = 0<br>n = 0<br>t = 0<br>u = 0<br>v = 0 |
| 21 | 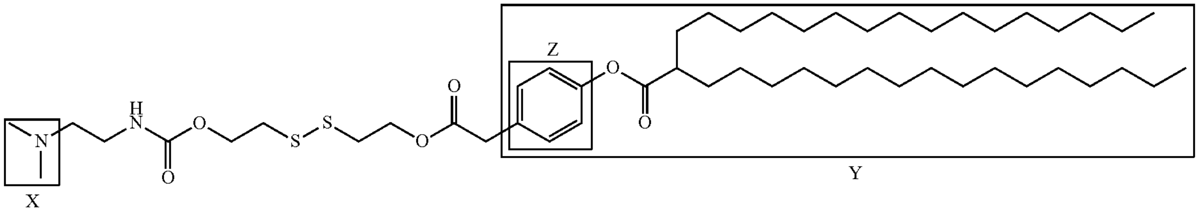<br>compound 21 | $R^1$: ethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |
| 22 | 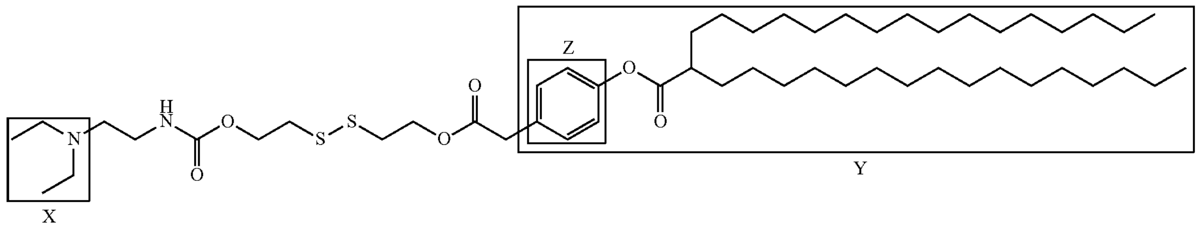<br>compound 22 | $R^1$: ethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |
| 23 | 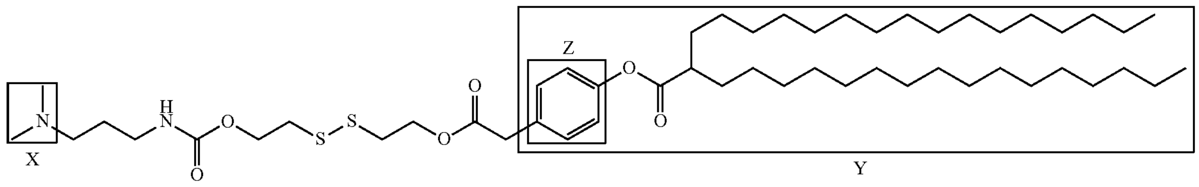<br>compound 23 | $R^1$: trimethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 24 | 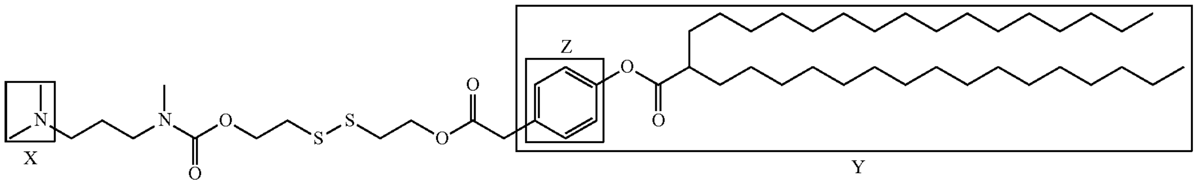 compound 24 | $R^1$: trimethylene<br>$R^2$: methylene<br>$R^x$: ethylene<br>$R^y$: ethylene<br>$R^7$: 1-hexadecyl-heptadecyl<br>$L^1$: N-methylcarbamate<br>$L^2$: ester<br>$L^x$: ester | k = 1<br>l = 0<br>m = 0<br>n = 0<br>t = 0<br>u = 0<br>v = 0 |
| 25 | 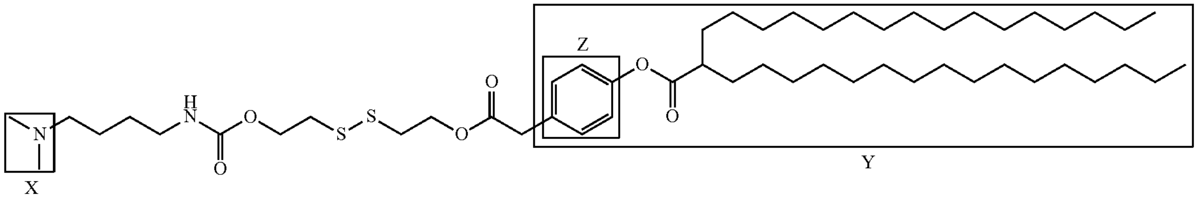 compound 25 | $R^1$: tetra-methylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |
| 26 | 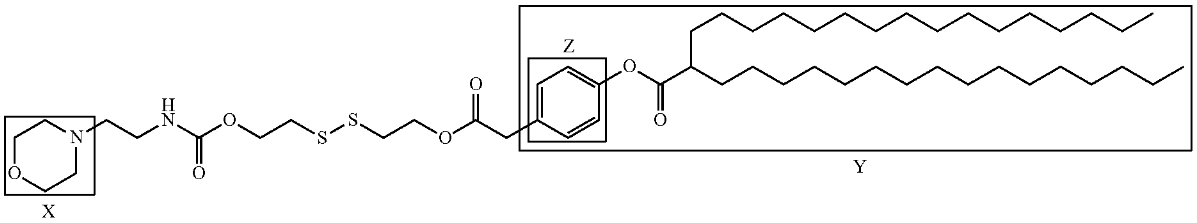 compound 26 | $R^1$: ethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |
| 27 | 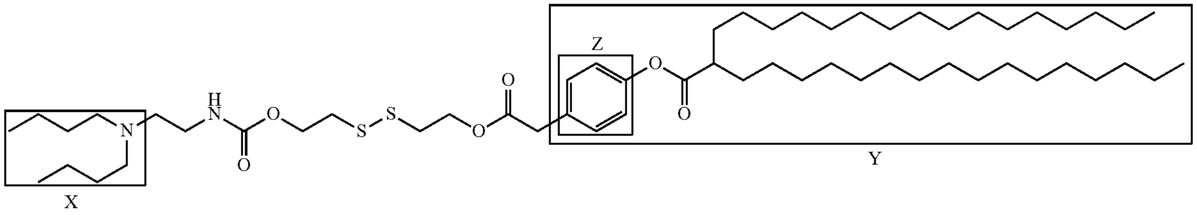 compound 27 | $R^1$: ethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 28 | 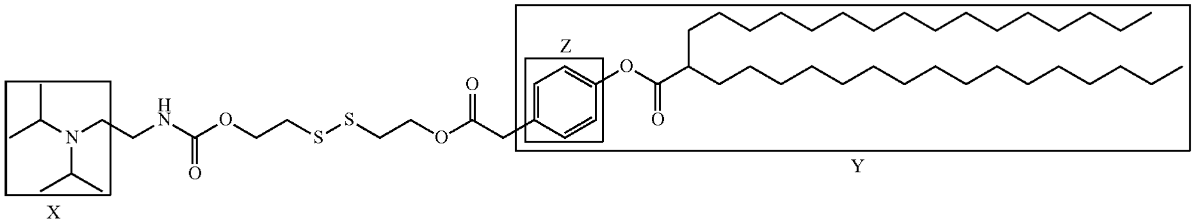 compound 28 | $R^1$: ethylene<br>$R^2$: methylene<br>$R^x$: ethylene<br>$R^y$: ethylene<br>$R^7$: 1-hexadecyl-heptadecyl<br>$L^1$: carbamate<br>$L^2$: ester<br>$L^x$: ester | k = 1<br>l = 0<br>m = 0<br>n = 0<br>t = 0<br>u = 0<br>v = 0 |
| 29 | 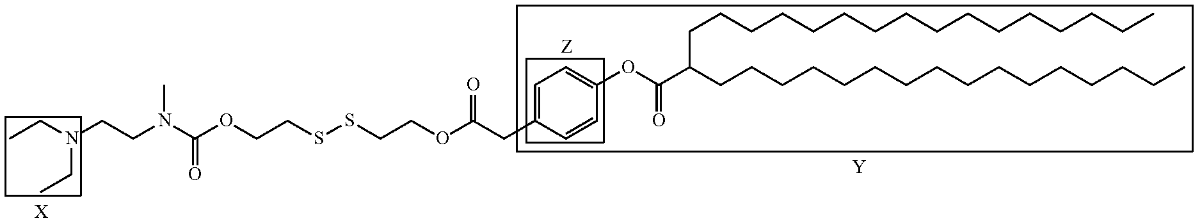 compound 29 | $R^1$: ethylene<br>$R^2$: methylene<br>$R^x$: ethylene<br>$R^y$: ethylene<br>$R^7$: 1-hexadecyl-heptadecyl<br>$L^1$: N-methyl-carbamate<br>$L^2$: ester<br>$L^x$: ester | k = 1<br>l = 0<br>m = 0<br>n = 0<br>t = 0<br>u = 0<br>v = 0 |
| 30 | 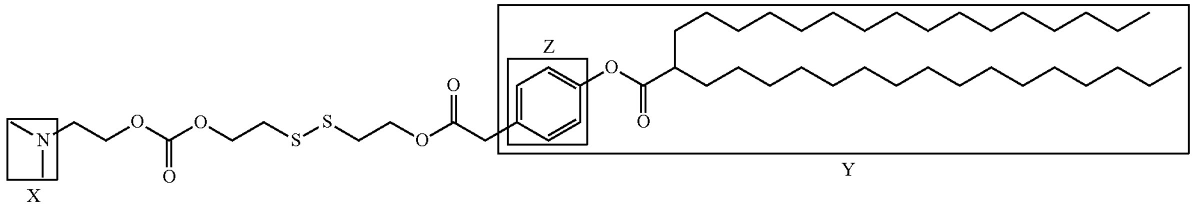 compound 30 | $R^1$: ethylene<br>$R^2$: methylene<br>$R^x$: ethylene<br>$R^y$: ethylene<br>$R^7$: 1-hexadecyl-heptadecyl<br>$L^1$: carbonate<br>$L^2$: ester<br>$L^x$: ester | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
| --- | --- | --- | --- |
| 31 | 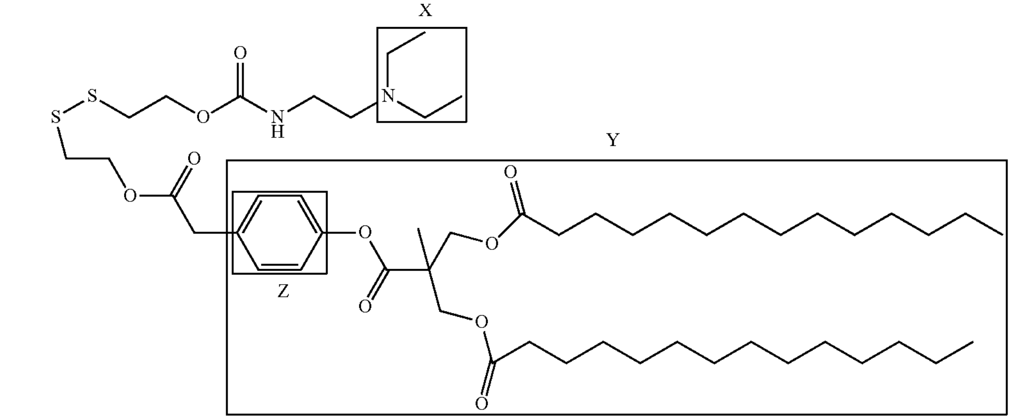 compound 31 | $R^1$: ethylene<br>$R^2$: methylene<br>$R^4$: absent<br>$R^5$: methyl<br>$R^6$: methylene<br>$R^{6'}$: methylene<br>$R^7$: tridecyl<br>$R^{7'''}$: tridecyl<br>$R^x$: ethylene<br>$R^y$: ethylene<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0 |
| 32 | 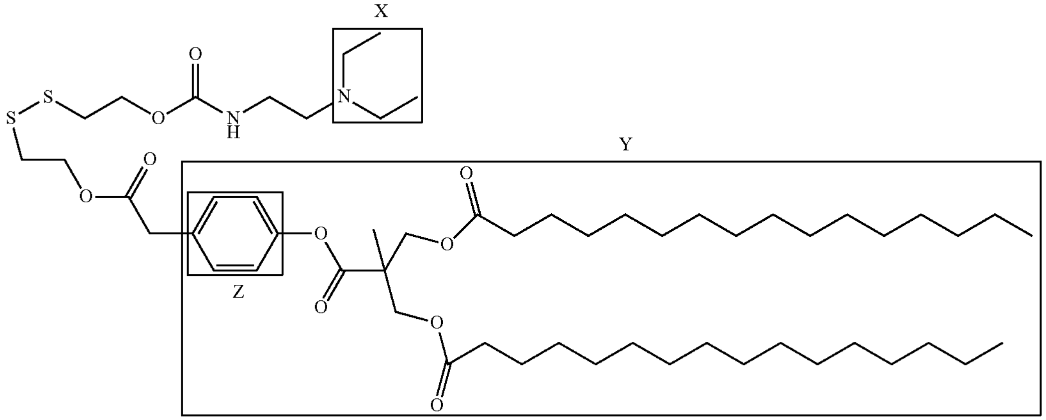 compound 32 | $R^1$: ethylene<br>$R^2$: methylene<br>$R^4$: absent<br>$R^5$: methyl<br>$R^6$: methylene<br>$R^{6'}$: methylene<br>$R^7$: pentadecyl<br>$R^{7'''}$: pentadecyl<br>$R^x$: ethylene<br>$R^y$: ethylene<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
| --- | --- | --- | --- |
| 33 | 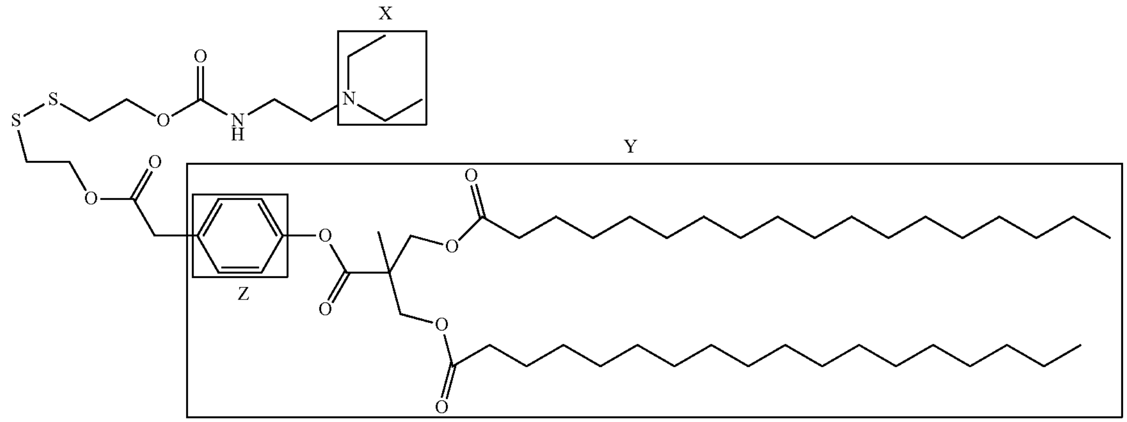<br>compound 33 | $R^1$: ethylene<br>$R^2$: methylene<br>$R^4$: absent<br>$R^5$: methyl<br>$R^6$: methylene<br>$R^{6'}$: methylene<br>$R^7$: heptadecyl<br>$R^{7'''}$: heptadecyl<br>$R^x$: ethylene<br>$R^y$: ethylene<br>$L^1$: carbamate<br>$L^2$: ester<br>$L^4$: ester<br>$L^{4'}$:ester<br>$L^x$: ester | k = 1<br>l = 0<br>m = 1<br>n = 1<br>t = 0<br>u = 0<br>v = 0 |
| 34 | 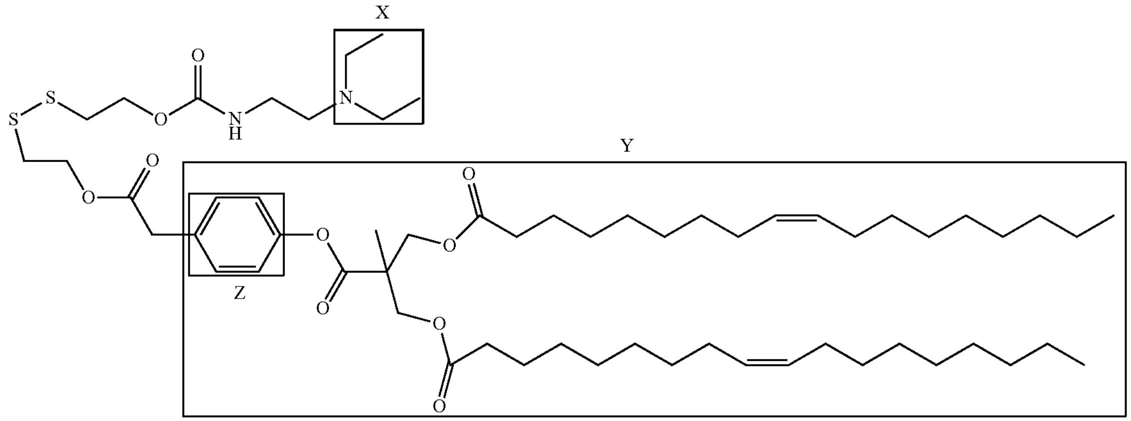<br>compound 34 | $R^1$: ethylene<br>$R^2$: methylene<br>$R^4$: absent<br>$R^5$: methyl<br>$R^6$: methylene<br>$R^{6'}$: methylene<br>$R^7$: heptadecenyl<br>$R^{7'''}$: hepta-decenyl<br>$R^x$: ethylene<br>$R^y$: ethylene<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 35 | 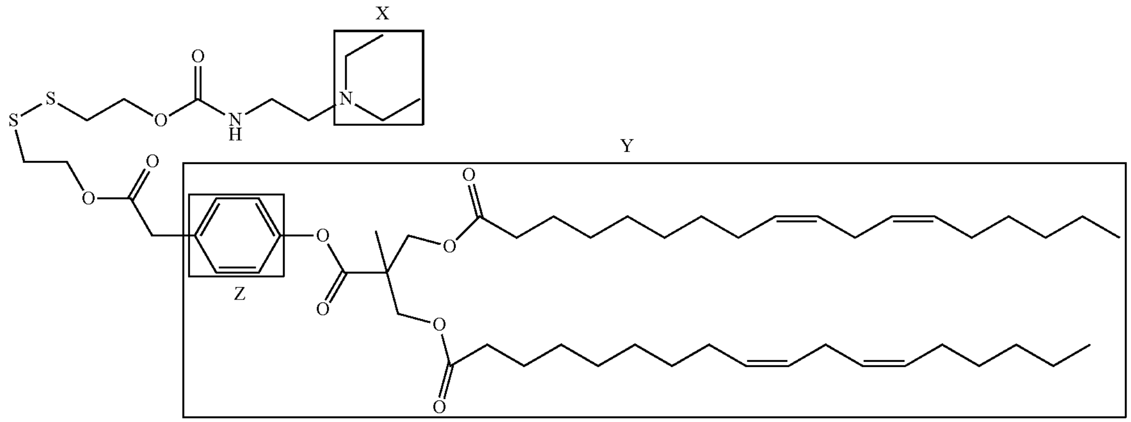<br>compound 35 | $R^1$: ethylene<br>$R^2$: methylene<br>$R^4$: absent<br>$R^5$: methyl<br>$R^6$: methylene<br>$R^{6'}$: methylene<br>$R^7$: hepta-decadienyl<br>$R^{7'''}$: hepta-decadienyl<br>$R^x$: ethylene<br>$R^y$: ethylene<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0 |
| 36 | 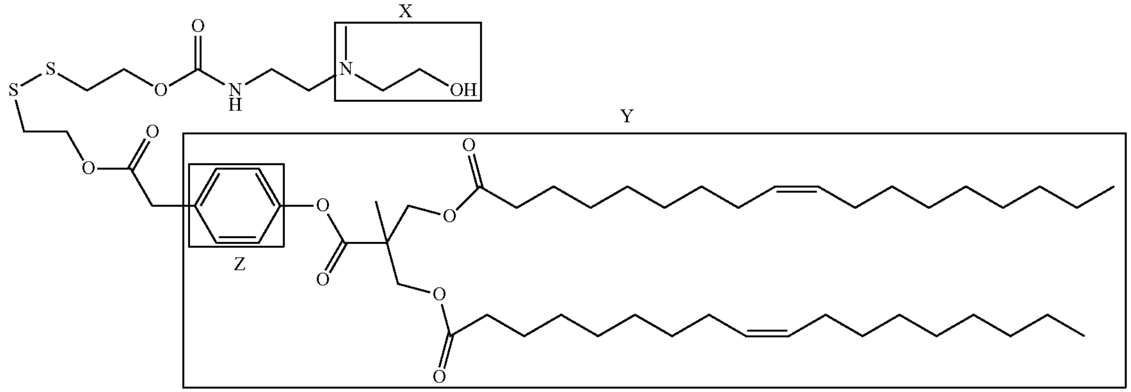<br>compound 36 | $R^1$: ethylene<br>$R^2$: methylene<br>$R^4$: absent<br>$R^5$: methyl<br>$R^6$: methylene<br>$R^{6'}$: methylene<br>$R^7$: heptadecenyl<br>$R^{7'''}$: hepta-decenyl<br>$R^x$: ethylene<br>$R^y$: ethylene<br>$R^a$: methyl<br>$R^b$: $-(CH_2)_2-OH$<br>$R^c$: hydrogen<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0<br>q = 2 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 37 | 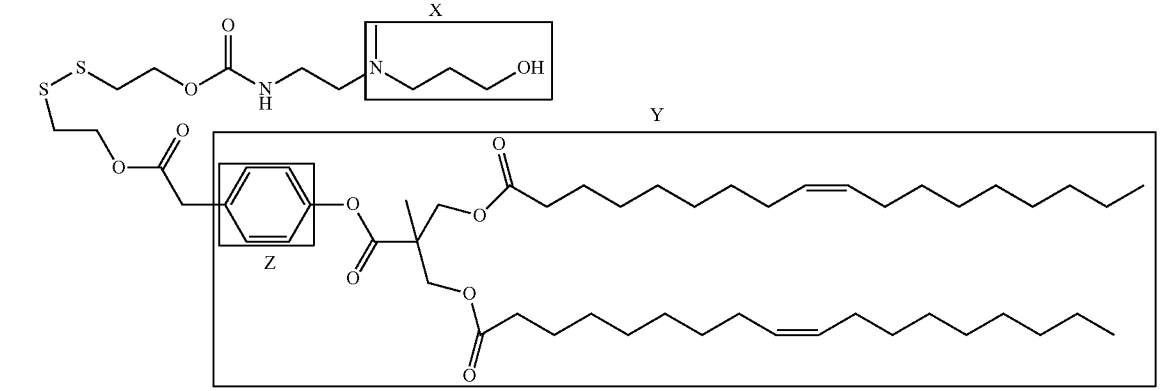<br>compound 37 | $R^1$: ethylene<br>$R^2$: methylene<br>$R^4$: absent<br>$R^5$: methyl<br>$R^6$: methylene<br>$R^{6'}$: methylene<br>$R^7$: heptadecenyl<br>$R^{7'''}$: hepta-decenyl<br>$R^x$: ethylene<br>$R^y$: ethylene<br>$R^a$: methyl<br>$R^b$: $-(CH_2)_3-OH$<br>$R^c$: hydrogen<br>$L^1$: carbamate<br>$L^2$: ester<br>$L^4$: ester<br>$L^{4'}$: ester<br>$L^x$: ester | k = 1<br>l = 0<br>m = 1<br>n = 1<br>t = 0<br>u = 0<br>v = 0<br>q = 3 |
| 38 | 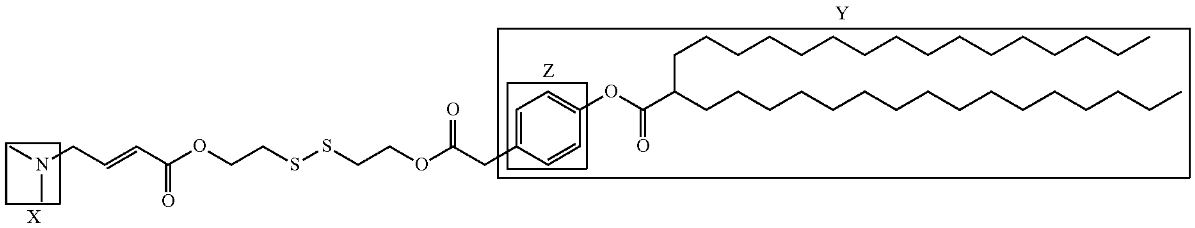<br>compound 38 | $R^1$: propenylene<br>$R^2$: methylene<br>$R^x$: ethylene<br>$R^y$: ethylene<br>$L^1$: ester<br>$L^2$: ester<br>$L^x$: ester<br>$R^7$: 1-hexadecyl-heptadecyl | k = 1<br>l = 0<br>m = 0<br>n = 0<br>t = 0<br>u = 0<br>v = 0 |
| 39 | 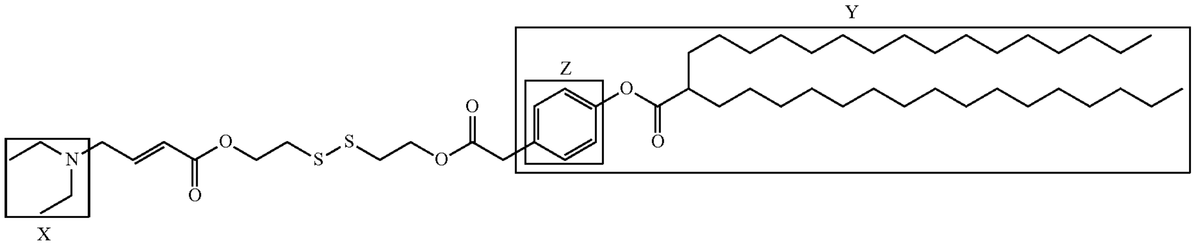<br>compound 39 | $R^1$: propenylene<br>$R^2$: methylene<br>$R^x$: ethylene<br>$R^y$: ethylene<br>$L^1$: ester<br>$L^2$: ester<br>$L^x$: ester<br>$R^7$: 1-hexadecyl-heptadecyl | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 40 | 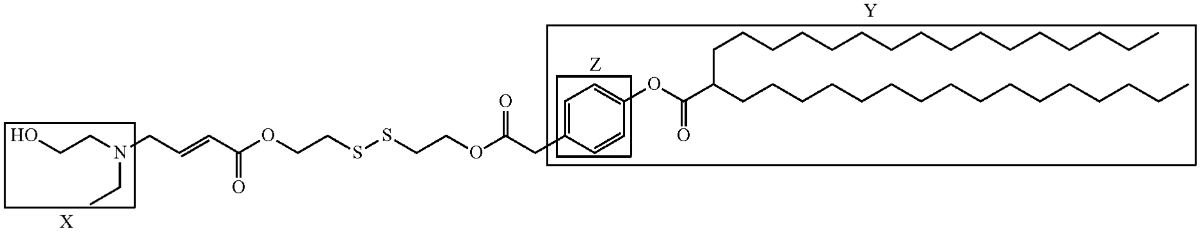 compound 40 | $R^1$: propenylene<br>$R^2$: methylene<br>$R^x$: ethylene<br>$R^y$: ethylene<br>$R^a$: ethyl<br>$R^b$: $-(CH_2)_2-OH$<br>$R^c$: hydrogen<br>$L^1$: ester<br>$L^2$: ester<br>$L^x$: ester<br>$R^7$: 1-hexadecyl-heptadecyl | k = 1<br>l = 0<br>m = 0<br>n = 0<br>t = 0<br>u = 0<br>v = 0<br>q = 2 |
| 41 | 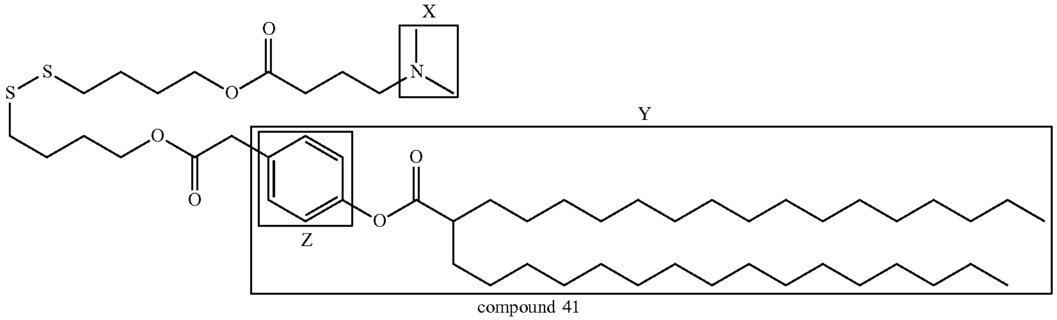 compound 41 | $R^1$: trimethylene<br>$R^2$: methylene<br>$R^x$: tetra-methylene<br>$R^y$: tetra-methylene<br>$L^1$: ester<br>$L^2$: ester<br>$L^x$: ester<br>$R^7$: 1-hexadecyl-heptadecyl | k = 1<br>l = 0<br>m = 0<br>n = 0<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 42 | 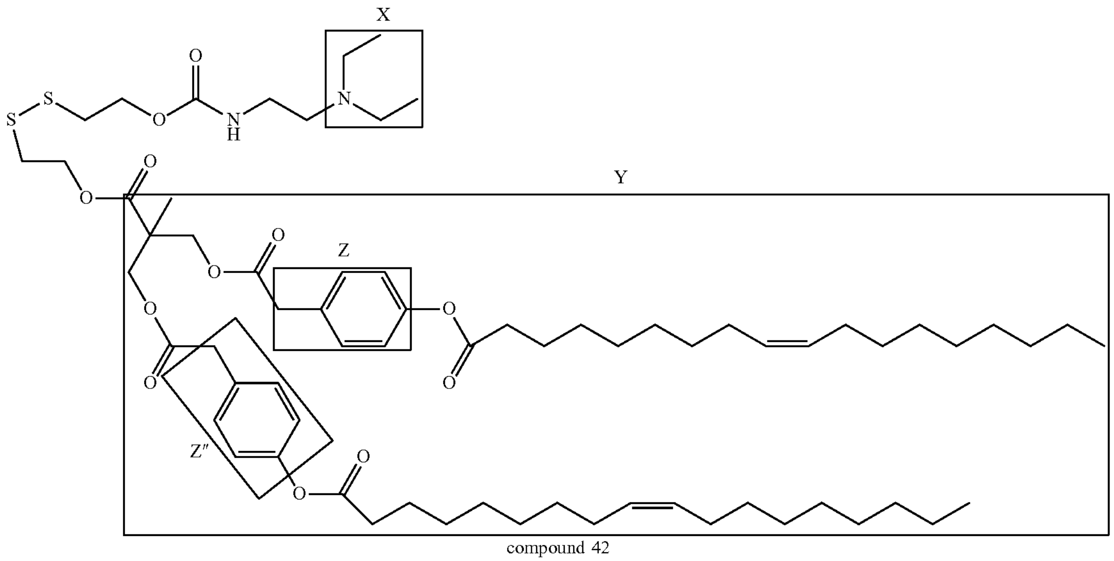<br>compound 42 | $R^1$: ethylene<br>$R^2$: absent<br>$R^3$: methylene<br>$R^7$: heptadecenyl<br>$R^{7''}$: hepta-decenyl<br>$R^x$: ethylene<br>$R^y$: ethylene<br>$R^{e'}$: methylene<br>$S^1$: methyl<br>$L^1$: carbamate<br>$L^2$: ester<br>$L^3$: ester<br>$L^a$: ester<br>$L^b$: ester<br>$L^x$: ester | k = 1<br>l = 1<br>m = 0<br>n = 0<br>t = 1<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 43 | 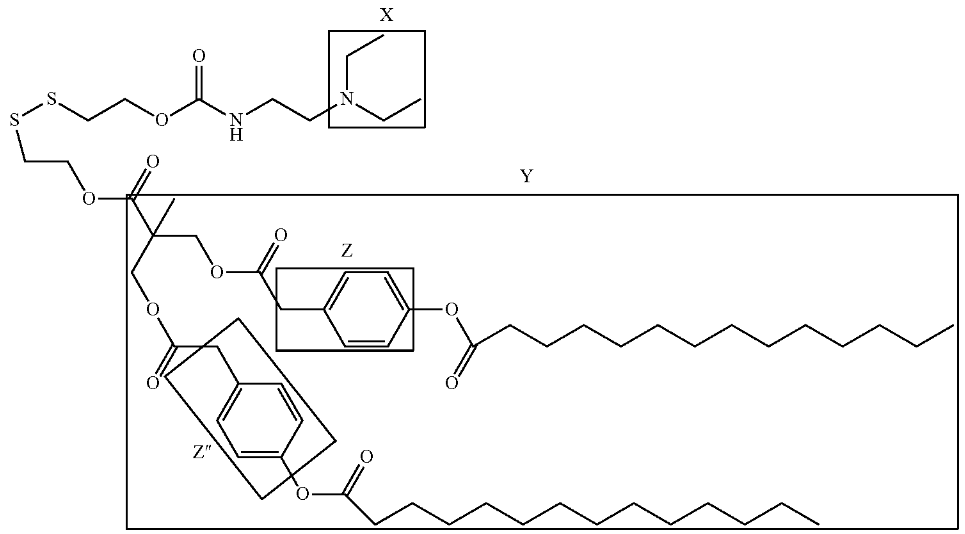 compound 43 | $R^1$: ethylene<br>$R^2$: absent<br>$R^3$: methylene<br>$R^7$: tridecanyl<br>$R^{7''}$: tridecanyl<br>$R^x$: ethylene<br>$R^y$: ethylene<br>$R^{e'}$: methylene<br>$S^1$: methyl<br>$L^1$: carbamate<br>$L^2$: ester<br>$L^3$: ester<br>$L^a$: ester<br>$L^b$: ester<br>$L^x$: ester | k = 1<br>l = 1<br>m = 0<br>n = 0<br>t = 1<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
|---|---|---|---|
| 44 | 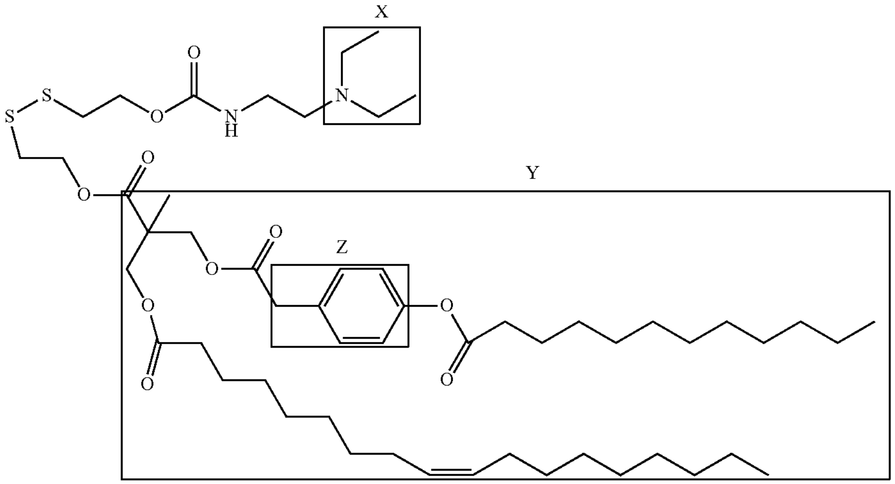<br>compound 44 | $R^1$: ethylene<br>$R^2$: absent<br>$R^3$: methylene<br>$R^7$: undecyl<br>$R^{7''}$: hepta-decenyl<br>$R^x$: ethylene<br>$R^y$: ethylene<br>$R^{e'}$: methylene<br>$S^1$: methyl<br>$L^1$: carbamate<br>$L^2$: ester<br>$L^3$: ester<br>$L^a$: ester<br>$L^x$: ester | k = 1<br>l = 1<br>m = 0<br>n = 0<br>t = 1<br>u = 0<br>v = 0 |
| 45 | 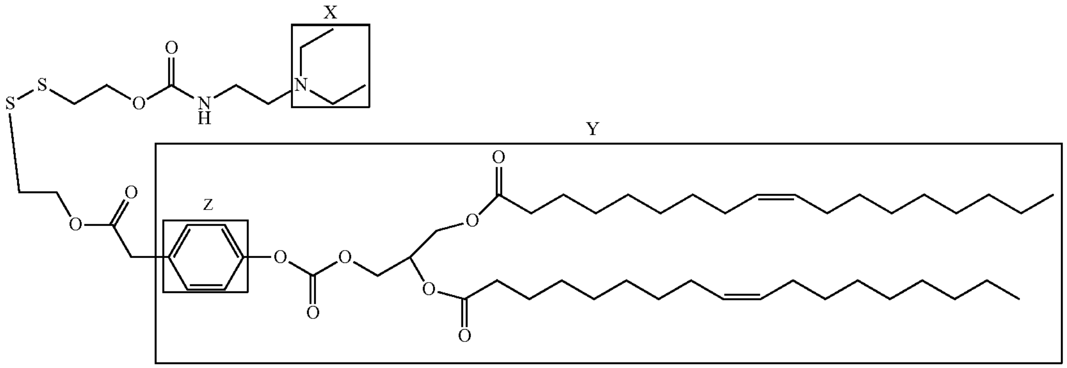<br>compound 45 | $R^1$: ethylene<br>$R^2$: methylene<br>$R^4$: methylene<br>$R^5$: hydrogen<br>$R^6$: methylene<br>$R^{6'}$: absent<br>$R^7$: heptadecenyl<br>$R^{7'''}$: hepta-decenyl<br>$R^x$: ethylene<br>$R^y$: ethylene<br>$L^1$: carbamate<br>$L^2$: ester<br>$L^4$: ester<br>$L^{4'}$: ester<br>$L^x$: carbonate | k = 1<br>l = 0<br>m = 1<br>n = 1<br>t = 0<br>u = 0<br>v = 0 |

TABLE 2-continued

| Ex. No. | name and structure (X, Y, Z correspond to formula (1)) | correspondence 1 with parameters in formulas (1) to (4) | correspondence 2 with parameters in formulas (1) to (4) |
| --- | --- | --- | --- |
| 46 | 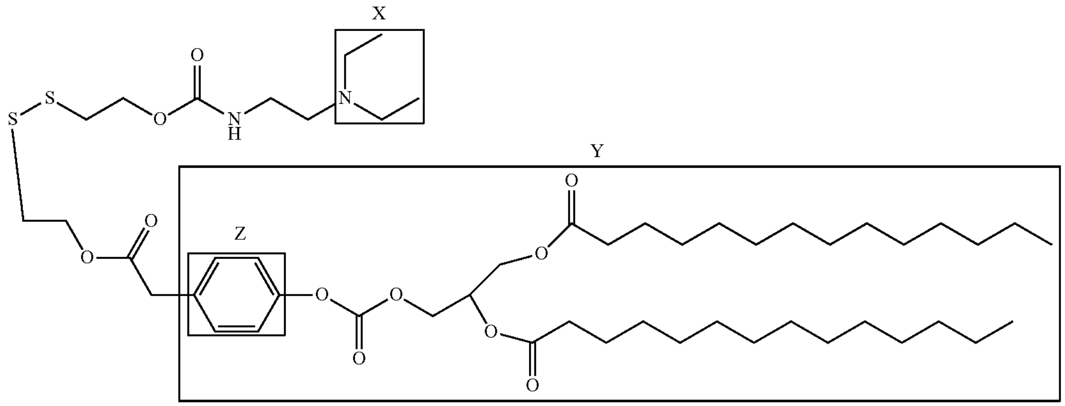 compound 46 | $R^1$: ethylene<br>$R^2$: methylene<br>$R^4$: methylene<br>$R^5$: hydrogen<br>$R^6$: methylene<br>$R^{6'}$: absent<br>$R^7$: tridecyl<br>$R^{7'''}$: tridecyl<br>$R^x$: ethylene<br>$R^y$: ethylene<br>$L^1$: carbamate<br>$L^2$: ester<br>$L^4$: ester<br>$L^{4'}$: ester<br>$L^x$: carbonate | k = 1<br>l = 0<br>m = 1<br>n = 1<br>t = 0<br>u = 0<br>v = 0 |

TABLE 3

| | name and structure |
|---|---|
| Comparative Example | 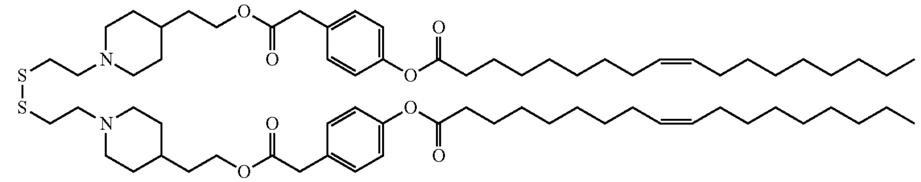 [SMILES: CCCCCCCC/C=C\CCCCCCCC(=O)Oc1ccc(CC(=O)OCCC2CCN(CCSSCCN3CCC(CCOC(=O)Cc4ccc(OC(=O)CCCCCCC/C=C\CCCCCCCC)cc4)CC3)CC2)cc1] O—Ph—P4C2 |

[Example 1] Synthesis of Compound 1

Compound 1 was prepared by the following synthetic route, but the present invention is not limited to such synthetic route.

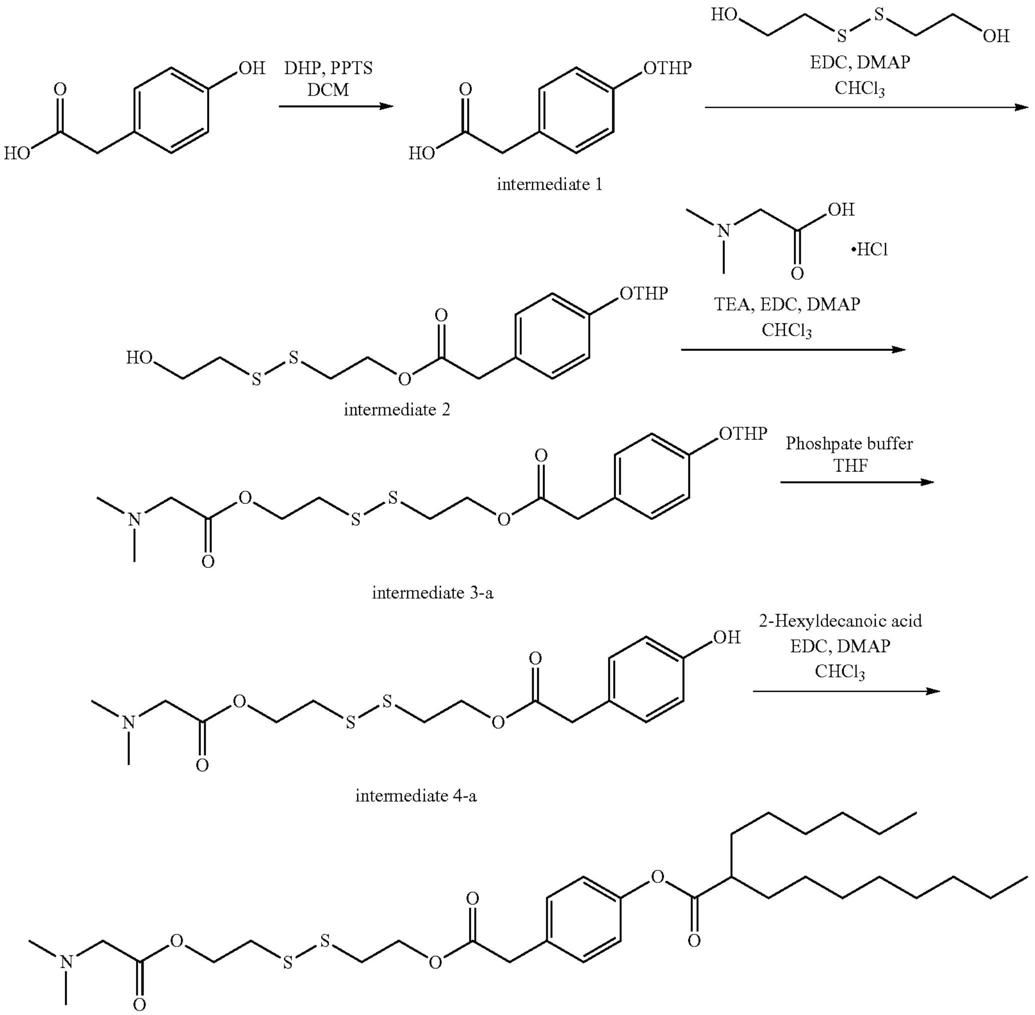

compound 1

Synthesis of Intermediate 1

4-Hydroxyphenylacetic acid (75.0 g) and PPTS (12.4 g) were dissolved in 400 g of dichloromethane at room temperature, and the obtained solution was cooled to 10-20° C. A solution obtained by dissolving DHP (207 g) in 100 g of dichloromethane was added dropwise to the solution, and the reaction was performed at 25° C. for 2 hr. The reaction solution was cooled to 10-20° C., and DMAP (30.1 g) was added to the solution to quench the reaction. 590 g of 2-propanol was added to the solution after the quenching, and the solution was cooled to 10-20° C. A solution of 98.8 g of 400 g/L aqueous sodium hydroxide solution and 307 g of ion-exchanged water were added dropwise to the solution after the cooling, and the reaction was performed at 25° C.

for 2 hr. The reaction solution was concentrated using an evaporator, and dichloromethane and 2-propanol were distilled off. The obtained concentrate was washed twice with 750 g of chloroform, and then 6N hydrochloric acid was added to obtain a solution with a pH of 5.0. The obtained solution was extracted twice with 750 g of chloroform, and the organic layer was dehydrated by adding 75.0 g of sodium sulfate. The sodium sulfate was removed by filtration, and the filtrate was concentrated in an evaporator to obtain 98.2 g of intermediate 1.

Synthesis of Intermediate 2

Intermediate 1 (10.2 g), bis(2-hydroxyethyl) disulfide (9.99 g), and DMAP (1.06 g) were dissolved in 153 g of chloroform at room temperature. EDC (12.4 g) was added to the obtained solution, and the mixture was allowed to react at 25° C. for 2 hr. The reaction solution was washed with 102 g of 20 wt % brine, and then dehydrated by adding 5.1 g of sodium sulfate. After removing the sodium sulfate by filtration, the filtrate was concentrated in an evaporator, and the obtained crude product was purified with a column to obtain 9.01 g of intermediate 2.

Synthesis of Intermediate 3-a

Intermediate 2 (350 mg), dimethylglycine hydrochloride (144 mg), triethylamine (143 mg), and DMAP (23.0 mg) were dissolved in 5.25 mL of chloroform at room temperature. EDC (270 mg) was added to the obtained solution and the mixture was reacted at room temperature for 2 hr. The reaction solution was washed with 3.5 g of 0.5 M phosphate buffer (pH 4.0), 3.5 g of 7 wt % sodium bicarbonate water, and 3.5 g of 20 wt % brine in that order, and then 175 mg of sodium sulfate was added for dehydration. After removing the sodium sulfate by filtration, the filtrate was concentrated in an evaporator to obtain 378 mg of intermediate 3-a.

Synthesis of Intermediate 4-a

Intermediate 3-a (363 mg) was dissolved in 3.27 g of THF, and then 13.1 g of 0.5 M phosphate buffer (pH 2.0) was added and the reaction was performed at room temperature for 2 hr. 5.45 g of chloroform was added to the reaction solution for washing. 1N aqueous sodium hydroxide solution was added to the washed aqueous layer to adjust the pH to 6.0, and the aqueous layer after pH adjustment was extracted with 5.45 g of chloroform. The organic layer was dehydrated by adding 180 mg of sodium sulfate, and the sodium sulfate was removed by filtration. The filtrate was concentrated using an evaporator to obtain 187 mg of intermediate 4-a.

Synthesis of Compound 1

Intermediate 4-a (187 mg), 2-hexyldecanoic acid (128 mg), and DMAP (12.0 mg) were dissolved in 2.81 g of chloroform at room temperature. EDC (144 mg) was added to the obtained solution, and the reaction was performed at 25° C. for 2 hr. The reaction solution was washed with 1.87 g of 20 wt % brine, and then 93.0 mg of sodium sulfate was added for dehydration. After removing the sodium sulfate by filtration, the filtrate was concentrated using an evaporator, and the obtained crude product was purified with a column to obtain 159 mg of compound 1.

$^1$H-NMR (600 MHz, $CDCl_3$) of Compound 1

δ:0.86-0.90 (m, 6H), 1.20-1.45 (m, 22H), 1.69-1.75 (m, 2H), 2.36 (s, 6H), 2.52-2.59 (m, 1H), 2.88-2.97 (m, 4H), 3.19 (s, 2H), 3.63 (s, 2H), 4.34-4.42 (m, 4H), 7.02-7.05 (m, 2H), 7.27-7.30 (m, 2H)

[Example 2] Synthesis of Compound 2

Synthesis of Compound 2

Using intermediate 4-a and 2-decyldodecanoic acid, compound 2 was synthesized by the same synthetic route as in Example 1.

$^1$H-NMR (600 MHz, $CDCl_3$) of Compound 2

δ: 0.88 (t, 6H), 1.20-1.45 (m, 34H), 1.69-1.75 (m, 2H), 2.36 (s, 6H), 2.52-2.59 (m, 1H), 2.88-2.97 (m, 4H), 3.19 (s, 2H), 3.63 (s, 2H), 4.34-4.42 (m, 4H), 7.02-7.05 (m, 2H), 7.27-7.30 (m, 2H)

[Example 3] Synthesis of Compound 3

Synthesis of Compound 3

Using intermediate 4-a and 2-tetradecylhexadecanoic acid, compound 3 was synthesized by the same synthetic route as in Example 1.

$^1$H-NMR (600 MHz, $CDCl_3$) of Compound 3

δ:0.88 (t, 6H), 1.20-1.45 (m, 50H), 1.69-1.75 (m, 2H), 2.36 (s, 6H), 2.52-2.59 (m, 1H), 2.88-2.97 (m, 4H), 3.19 (s, 2H), 3.63 (s, 2H), 4.34-4.42 (m, 4H), 7.02-7.05 (m, 2H), 7.27-7.30 (m, 2H)

[Example 4] Synthesis of Compound 4

Synthesis of Intermediate 3-b

In the same manner as in Example 1 except that 4-(dimethylamino)butanoic acid hydrochloride was used, intermediate 3-b represented by the following formula was synthesized.

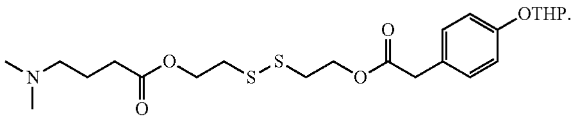

Synthesis of Intermediate 4-b

In the same manner as in Example 1 except that-intermediate 3-b was used, intermediate 4-b represented by the following formula was synthesized.

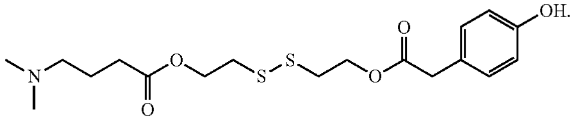 [SMILES: CN(C)CCCC(=O)OCCSSCCOC(=O)Cc1ccc(O)cc1]

Synthesis of Compound 4

In the same manner as in Example 1 except that intermediate 4-b was used, compound 4 was synthesized.

$^1H$-NMR (600 MHz, $CDCl_3$) of Compound 4

δ:0.86-0.90 (m, 6H), 1.20-1.45 (m, 22H), 1.69-1.82 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 5] Synthesis of Compound 5

Synthesis of Compound 5

Using intermediate 4-b and 2-decyldodecanoic acid, compound 5 was synthesized by the same synthetic route as in Example 1.

$^1H$-NMR (600 MHz, $CDCl_3$) of Compound 5

δ:0.88 (t, 6H), 1.20-1.45 (m, 34H), 1.69-1.84 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 6] Synthesis of Compound 6

Synthesis of Compound 6

Using intermediate 4-b and 2-dodecyltetradecanoic acid, compound 6 was synthesized by the same synthetic route as in Example 1.

$^1H$-NMR (600 MHz, $CDCl_3$) of Compound 6

δ:0.88 (t, 6H), 1.20-1.45 (m, 42H), 1.69-1.84 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 7] Synthesis of Compound 7

Synthesis of Compound 7

Using intermediate 4-b and 2-tetradecylhexadecanoic acid, compound 7 was synthesized by the same synthetic route as in Example 1.

$^1H$-NMR (600 MHz, $CDCl_3$) of Compound 7

δ:0.88 (t, 6H), 1.20-1.45 (m, 50H), 1.69-1.84 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 8] Synthesis of Compound 8

Synthesis of Compound 8

Using intermediate 4-b and 2-hexadecyloctadecanoic acid, compound 8 was synthesized by the same synthetic route as in Example 1.

$^1H$-NMR (600 MHz, $CDCl_3$) of Compound 8

δ:0.88 (t, 6H), 1.20-1.45 (m, 58H), 1.69-1.84 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 9] Synthesis of Compound 9

Synthesis of Compound 9

Using intermediate 4-b and 2-octadecyleicosanoic acid, compound 9 was synthesized by the same synthetic route as in Example 1.

$^1H$-NMR (600 MHz, $CDCl_3$) of Compound 9

δ:0.88 (t, 6H), 1.20-1.45 (m, 66H), 1.69-1.84 (m, 4H), 2.21 (s, 6H), 2.28 (t, 2H), 2.35 (t, 2H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

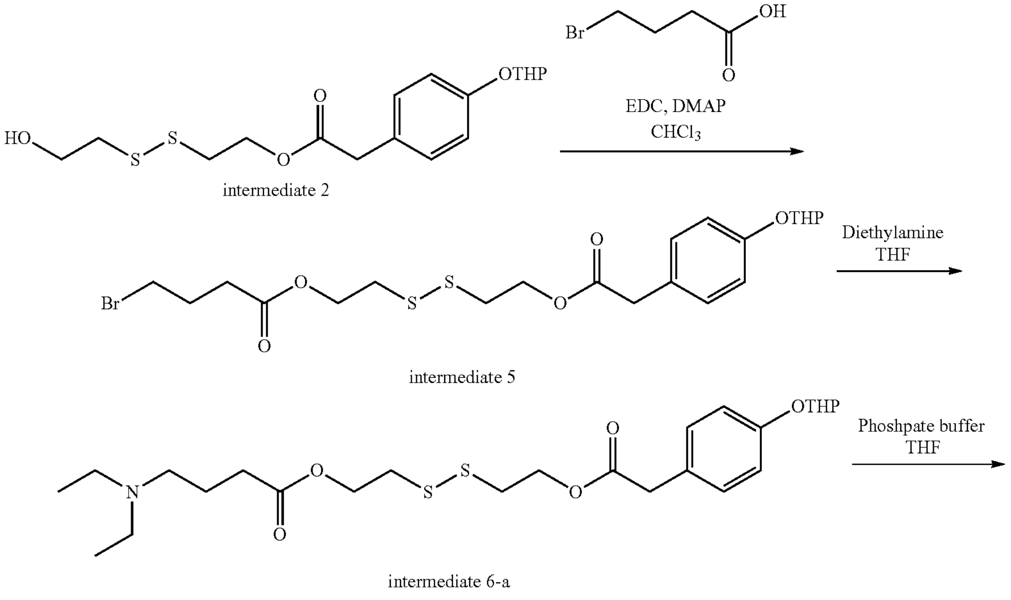

-continued

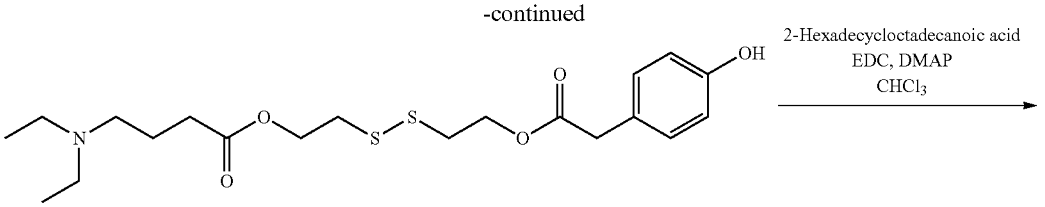

intermediate 7-a

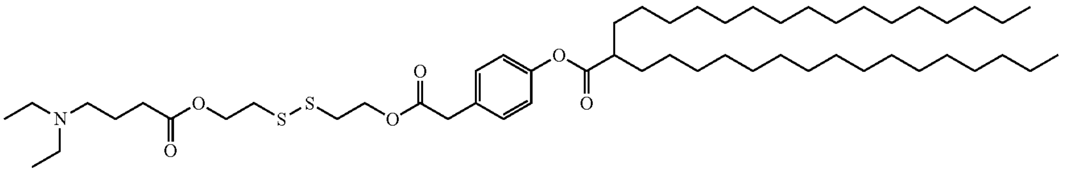

compound 10

[Example 10] Synthesis of Compound 10

Synthesis of Intermediate 5

Intermediate 2 (5.10 g), 4-bromobutyric acid (2.52 g), and DMAP (335 mg) were dissolved in 76.5 g of chloroform at room temperature. EDC (3.94 g) was added to the obtained solution and the mixture was reacted at 25° C. for 2 hr. The reaction solution was washed with 51.0 g of 20 wt % brine, and then 2.55 g of sodium sulfate was added for dehydration. After removing the sodium sulfate by filtration, the filtrate was concentrated in an evaporator to obtain 6.07 g of Intermediate 5.

Synthesis of Intermediate 6-a

Diethylamine (258 mg) was dissolved in 1.04 g of THF at room temperature. A solution obtained by dissolving intermediate 5 (230 mg) in 780 mg of THF was added dropwise to the solution, and the mixture was reacted at 50° C. for 15 hr. After adding 3.45 g of chloroform to the reaction solution, the mixture was washed with 2.30 g of 0.5 M acetate buffer (pH 4.0), 2.30 g of 7 wt % sodium bicarbonate water, and 2.30 g of 20 wt % brine in that order. After adding 130 mg of sodium sulfate to dehydrate, the sodium sulfate was removed by filtration, and the filtrate was concentrated in an evaporator to obtain 130 mg of intermediate 6-a.

Synthesis of Intermediate 7-a

Using intermediate 6-a, intermediate 7-a was synthesized by a method similar to that for intermediate 4-a in Example 1.

Synthesis of Compound 10

Using intermediate 7-a and 2-hexadecyloctadecanoic acid, compound 10 was synthesized by a method similar to that for compound 1 in Example 1.

$^1$H-NMR (600 MHz, $CDCl_3$) of Compound 10

δ:0.88 (t, 6H), 1.00 (t, 6H), 1.20-1.45 (m, 58H), 1.69-1.84 (m, 4H), 2.28-2.60 (m, 9H), 2.88-2.97 (m, 4H), 3.63 (s, 2H), 4.28-4.38 (m, 4H), 7.02-7.05 (m, 2H), 7.27-7.30 (m, 2H)

[Example 11] Synthesis of Compound 11

Synthesis of Intermediate 6-b

In the same manner as in Example 10 except that piperidine was used, intermediate 6-b represented by the following formula was synthesized.

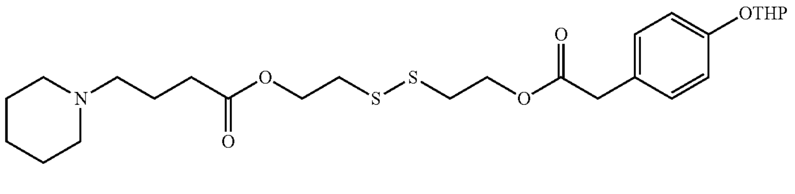

Synthesis of Intermediate 7-b

In the same manner as in Example 10 except that intermediate 6-b was used, intermediate 7-b represented by the following formula was synthesized.

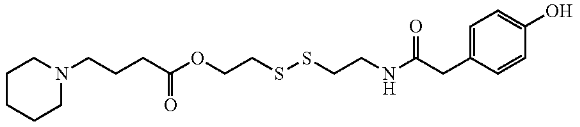 [SMILES: O=C(Cc1ccc(O)cc1)NCCSSCCOC(=O)CCCN1CCCCC1]

Synthesis of Compound 11

Using intermediate 7-b and 2-hexadecyloctadecanoic acid, compound 11 was synthesized by the same synthetic route as in Example 10.

$^1$H-NMR (600 MHz, $CDCl_3$) of Compound 11

δ:0.88 (t, 6H), 1.20-1.45 (m, 60H), 1.45-1.60 (m, 4H), 1.69-1.84 (m, 4H), 2.20-2.50 (m, 8H), 2.52-2.59 (m, 1H), 2.88-2.97 (m, 4H), 3.63 (s, 2H), 4.28-4.38 (m, 4H), 7.02-7.05 (m, 2H), 7.27-7.30 (m, 2H)

[Example 12] Synthesis of Compound 12

Synthesis of Intermediate 6-c

In the same manner as in Example 10 except that dipropylamine was used, intermediate 6-c represented by the following formula was synthesized.

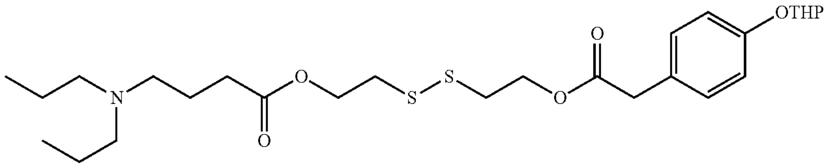

Synthesis of Intermediate 7-c

In the same manner as in Example 10 except that intermediate 6-c was used, intermediate 7-c represented by the following formula was synthesized.

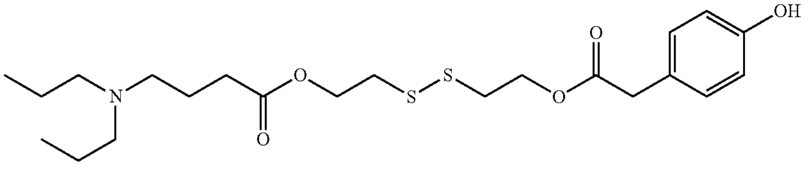 [SMILES: CCCN(CCC)CCCC(=O)OCCSSCCOC(=O)Cc1ccc(O)cc1]

Synthesis of Compound 12

Using intermediate 7-c and 2-hexadecyloctadecanoic acid, compound 12 was synthesized by the same synthetic route as in Example 10.

$^1$H-NMR (600 MHz, $CDCl_3$) of Compound 12

δ:0.86-0.92 (m, 12H), 1.20-1.45 (m, 62H), 1.69-1.84 (m, 4H), 2.28-2.60 (m, 9H), 2.88-2.97 (m, 4H), 3.63 (s, 2H), 4.28-4.38 (m, 4H), 7.02-7.05 (m, 2H), 7.27-7.30 (m, 2H)

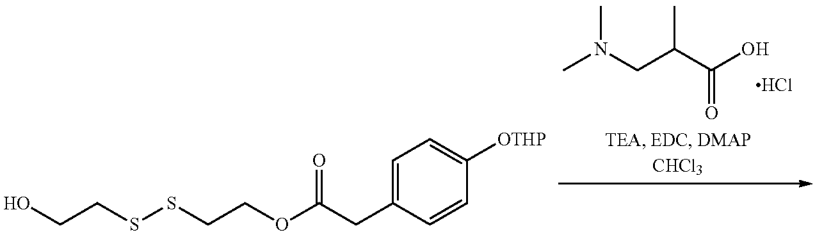

intermediate 2

-continued

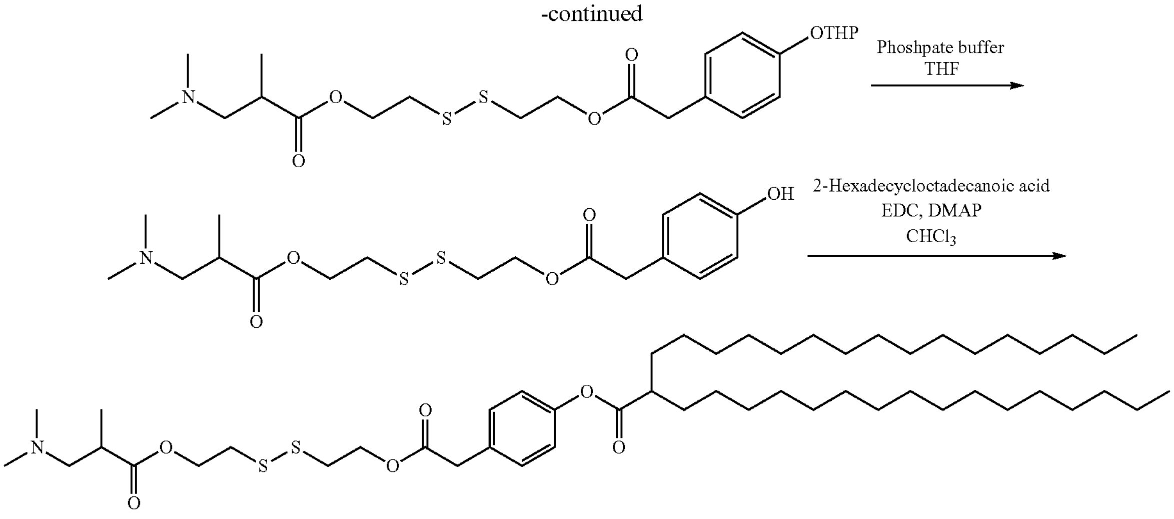

compound 13

[Example 13] Synthesis of Compound 13

Synthesis of Compound 13

By a synthesis route similar to that in Example 8 except that intermediate 2 and 3-(dimethylamino)-2-methylpropionic acid hydrochloride were used as starting materials, compound 13 was synthesized.

$^1$H-NMR (600 MHz, $CDCl_3$) of Compound 13

δ:0.88 (t, 6H), 1.13 (d, 3H), 1.20-1.45 (m, 58H), 1.68-1.78 (m, 2H), 2.18-2.22 (m, 7H), 2.52-2.70 (m, 3H), 2.88-2.97 (m, 4H), 3.63 (s, 2H), 4.28-4.38 (m, 4H), 7.02-7.05 (m, 2H), 7.27-7.30 (m, 2H)

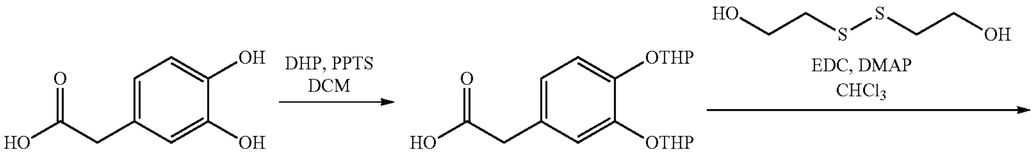

intermediate 8

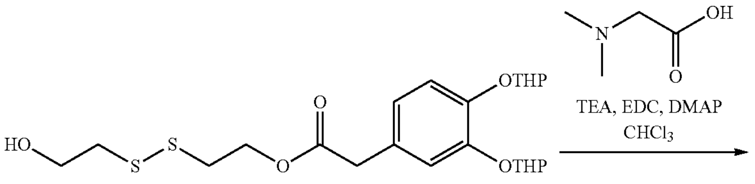

intermediate 9

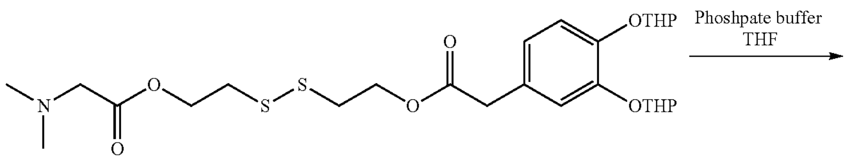

intermediate 10-a

-continued

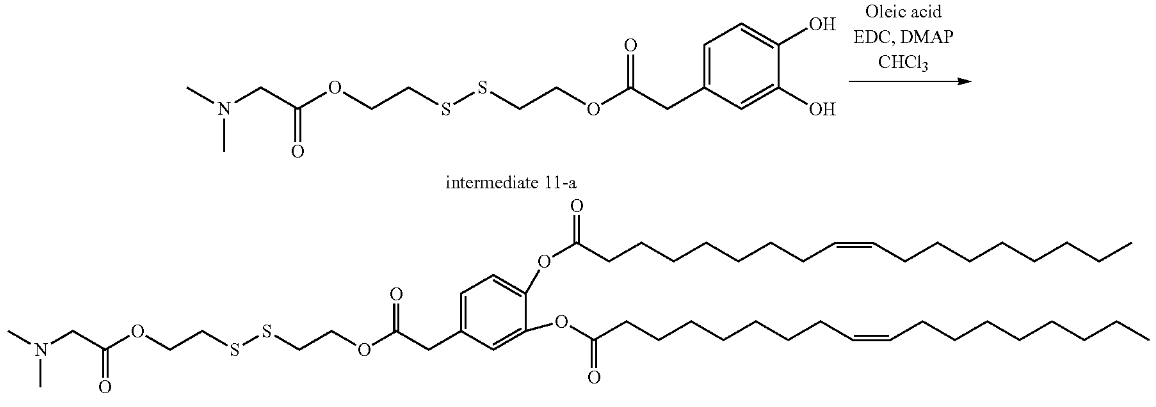

intermediate 11-a compound 14

[Example 14] Synthesis of Compound 14

Synthesis of Intermediate 8

3,4-Dihydroxyphenylacetic acid (3.00 g) and PPTS (448 mg) were dissolved in 40.0 g of dichloromethane at room temperature, and the obtained solution was cooled to 20° C. DHP (7.50 g) was added dropwise to the solution, and the reaction was performed at room temperature for 2 hr. The reaction solution was cooled 10 to 20° C., and DMAP (1.09 g) was added to the solution to quench the reaction. 47.0 g of 2-propanol was added to the solution after the quenching, and the solution was cooled to 10-20° C. 30.0 g of 1N aqueous sodium hydroxide solution was added dropwise to the solution after the cooling, and the reaction was performed at 25° C. for 2 hr. The reaction solution was concentrated using an evaporator, and dichloromethane and 2-propanol were distilled off. The concentrate was washed with 30.0 g of chloroform, and then 6N hydrochloric acid was added to obtain a solution with a pH of 5.0. The solution was extracted with 30.0 g of chloroform, and the organic layer was dehydrated by adding 1.50 g of sodium sulfate. After removing the sodium sulfate by filtration, the filtrate was concentrated in an evaporator to obtain 4.98 g of intermediate 8.

Synthesis of Intermediate 9

Intermediate 8 (800 mg), bis(2-hydroxyethyl) disulfide (550 mg), and DMAP (58.0 mg) were dissolved in 12.0 g of chloroform at room temperature. EDC (684 mg) was added to the obtained solution, and the reaction was performed at 25° C. for 2 hr. The reaction solution was washed with 8.00 g of 20 wt % brine, and then dehydrated by adding 400 mg of sodium sulfate. After removing sodium sulfate by filtration, the filtrate was concentrated using an evaporator, and the obtained crude product was purified with a column to obtain 530 mg of intermediate 9.

Synthesis of Intermediate 10-a

Intermediate 9 (525 mg), dimethylglycine hydrochloride (171 mg), triethylamine (169 mg), and DMAP (27.0 mg) were dissolved in 7.90 g of chloroform at room temperature. EDC (319 mg) was added to the obtained solution and the mixture was reacted at room temperature for 2 hr. The reaction solution was washed with 5.25 g of 0.5 M phosphate buffer (pH 4.0), 5.25 g of 7 wt % sodium bicarbonate water, and 5.25 g of 20 wt % brine, in that order, and then 250 mg of sodium sulfate was added for dehydration. After removing sodium sulfate by filtration, the filtrate was concentrated using an evaporator to obtain 558 mg of intermediate 10-a.

Synthesis of Intermediate 11-a

Intermediate 10-a (550 mg) was dissolved in 4.95 g of THF, and then 19.8 g of 0.5 M phosphate buffer (pH 2.0) was added and the mixture was reacted at room temperature for 2 hr. 8.25 g of chloroform was added to the reaction solution for washing. 1N aqueous sodium hydroxide solution was added to the washed aqueous layer to adjust the pH to 6.5, and the aqueous layer after pH adjustment was extracted with 8.25 g of chloroform. 300 mg of sodium sulfate was added to the organic layer for dehydration, and sodium sulfate was removed by filtration. The filtrate was concentrated in an evaporator to obtain 503 mg of intermediate 11-a.

Synthesis of Compound 14

Intermediate 11-a (190 mg), oleic acid (289 mg), and DMAP (24.0 mg) were dissolved in 2.85 g of chloroform at room temperature. EDC (234 mg) was added to the obtained solution and the mixture was reacted at 25° C. for 2 hr. The reaction solution was washed with 1.90 g of 20 wt % brine, and then dehydrated by adding 100 mg of sodium sulfate. After removing sodium sulfate by filtration, the filtrate was concentrated in an evaporator and purified with a column to obtain 291 mg of compound 14.

$^1$H-NMR (600 MHz, $CDCl_3$) of Compound 14

δ:0.88 (t, 6H), 1.22-1.42 (m, 40H), 1.69-1.83 (m, 6H), 1.99-2.05 (m, 8H), 2.36 (s, 6H), 2.50-2.53 (m, 4H), 2.88-2.97 (m, 4H), 3.63 (s, 2H), 4.34-4.42 (m, 4H), 5.32-5.38 (m, 4H), 7.10-7.17 (m, 3H)

[Example 15] Synthesis of Compound 15

Synthesis of Intermediate 10-b

In the same manner as in Example 14 except that 4-(dimethylamino)butanoic acid hydrochloride was used, intermediate 10-b represented by the following formula was synthesized.

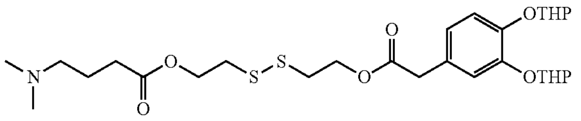

Synthesis of Intermediate 11-b

In the same manner as in Example 14 except that intermediate 10-b was used, intermediate 11-b represented by the following formula was synthesized.

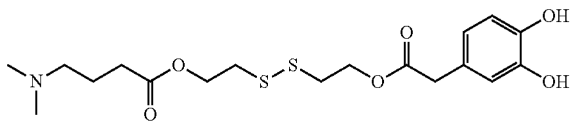 [SMILES: CN(C)CCCC(=O)OCCSSCCOC(=O)Cc1ccc(O)c(O)c1]

Synthesis of Compound 15

Using intermediate 11-b and oleic acid, compound 15 was synthesized by the same synthetic route as in Example 14.

$^1$H-NMR (600 MHz, $CDCl_3$) of Compound 15

δ:0.88 (t, 6H), 1.22-1.42 (m, 40H), 1.69-1.83 (m, 6H), 1.99-2.05 (m, 8H), 2.26 (s, 6H), 2.33-2.54 (m, 4H), 2.50-2.53 (m, 4H), 2.88-2.97 (m, 4H), 3.63 (s, 2H), 4.34-4.42 (m, 4H), 5.32-5.38 (m, 4H), 7.10-7.17 (m, 3H)

[Example 16] Synthesis of Compound 16

Synthesis of Intermediate 12

Intermediate 2 (5.00 g) and triethylamine (2.72 g) were dissolved in 125 g of chloroform at room temperature. Methanesulfonyl chloride (2.31 g) was added to the obtained solution and the mixture was reacted at 25° C. for 3 hr. The 0.20 reaction solution was washed with 75.0 g of 7 wt % sodium bicarbonate water, and 5.00 g of sodium sulfate was added for dehydration. After removing the sodium sulfate by filtration, the filtrate was concentrated in an evaporator and purified with a column to obtain 4.42 g of intermediate 12.

Synthesis of Intermediate 13-a

Intermediate 12 (600 mg) was dissolved in 5.40 g of dimethylamine (2.0 mol/L in THF), and TBAI (49.0 mg) was added and the mixture was reacted at 25° C. for 20 hr. The reaction solution was added with 9.00 g of chloroform, washed with 6.00 g of 0.5 M acetate buffer (pH 4.0), and dehydrated by adding 300 mg of sodium sulfate. After removing the sodium sulfate by filtration, the filtrate was concentrated using an evaporator to obtain 470 mg of intermediate 13-a.

Synthesis of Intermediate 14-a

In the same manner as in intermediate 4-a of Example 1 except that intermediate 13-a was used, intermediate 14-a was synthesized.

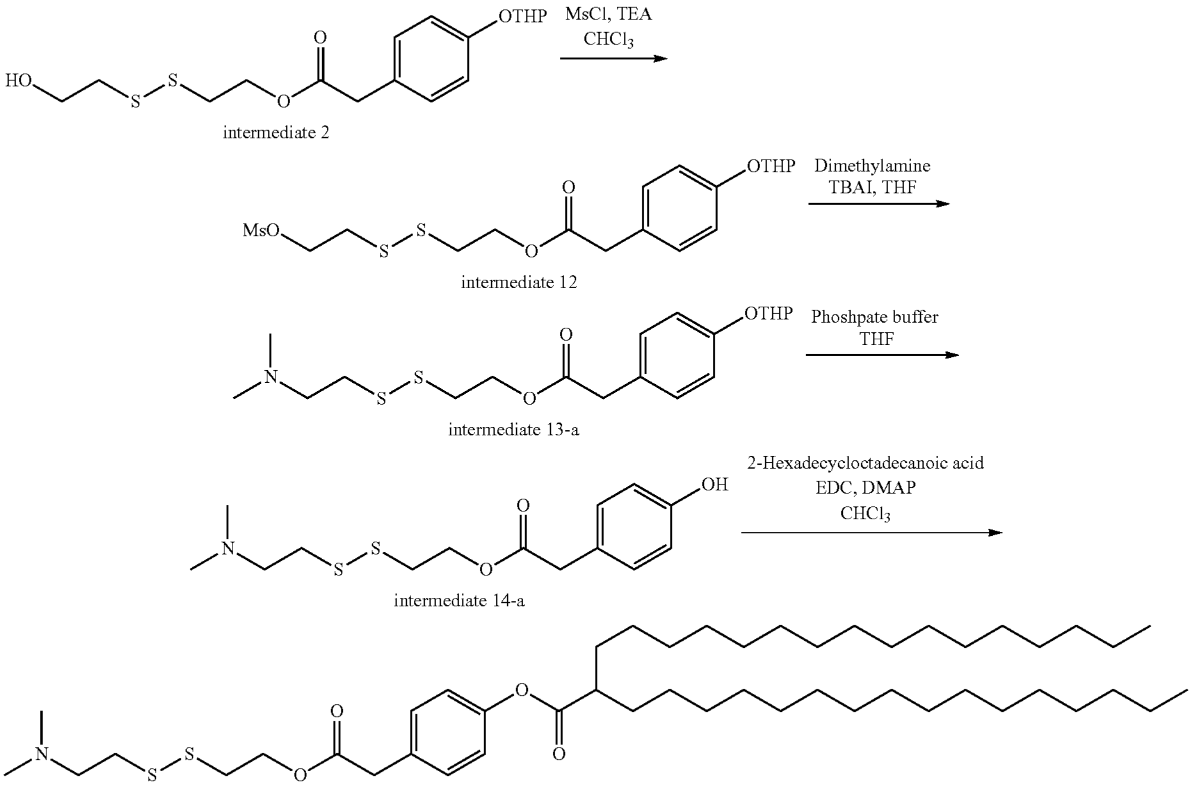

intermediate 2 intermediate 12 intermediate 13-a intermediate 14-a compound 16

Synthesis of Compound 16

Using intermediate 14-a and 2-hexadecyloctadecanoic acid, compound 16 was synthesized by a method similar to that for compound 1 in Example 1.

$^1$H-NMR (600 MHz, $CDCl_3$) of Compound 16

δ:0.88 (t, 6H), 1.20-1.45 (m, 58H), 1.69-1.84 (m, 2H), 2.25 (s, 6H), 2.52-2.60 (m, 3H), 2.80 (t, 2H), 2.90 (t, 2H), 3.63 (s, 2H), 4.35 (t, 2H), 7.02-7.05 (m, 2H), 7.27-7.30 (m, 2H)

[Example 17] Synthesis of Compound 17

Synthesis of Intermediate 13-b 4.20 g of THF was added to intermediate 12 (600 mg) and diethylamine (779 mg) and dissolved at room temperature. TBAI (49.0 mg) was added to the obtained solution and the mixture was reacted at 25° C. for 3 hr. 9.00 g of chloroform was added to the reaction solution, which was washed with 6.00 g of 0.5 M acetate buffer (pH 4.0), and 300 mg of sodium sulfate was added for dehydration. After removing sodium sulfate by filtration, the filtrate was concentrated using an evaporator to obtain 473 mg of intermediate 13-b represented by the following formula.

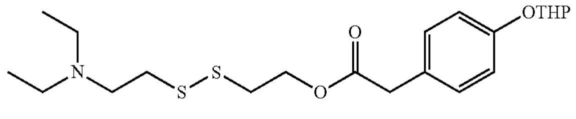

Synthesis of Intermediate 14-b

In the same manner as in Example 16 except that intermediate 13-b was used, intermediate 14-b represented by the following formula was synthesized.

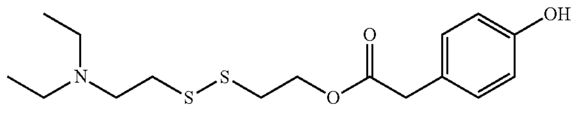 [SMILES: CCN(CC)CCSSCCOC(=O)Cc1ccc(O)cc1]

Synthesis of Compound 17

Using intermediate 14-b and 2-hexadecyloctadecanoic acid, compound 17 was synthesized by the same synthetic route as in Example 16.

$^1$H-NMR (600 MHz, $CDCl_3$) of Compound 17

δ:0.88 (t, 6H), 1.03 (t, 6H), 1.20-1.45 (m, 58H), 1.69-1.84 (m, 2H), 2.53-2.57 (m, 5H), 2.75-2.80 (m, 4H), 2.91 (t, 2H), 3.63 (s, 2H), 4.35 (t, 2H), 7.02-7.05 (m, 2H), 7.27-7.30 (m, 2H)

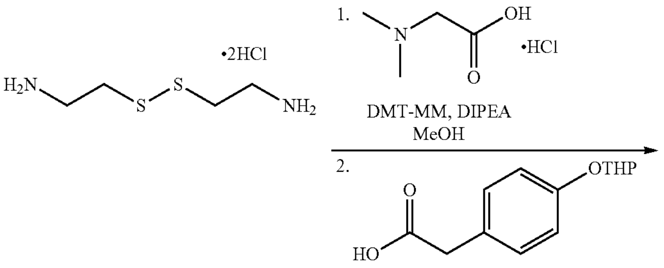

intermediate 1

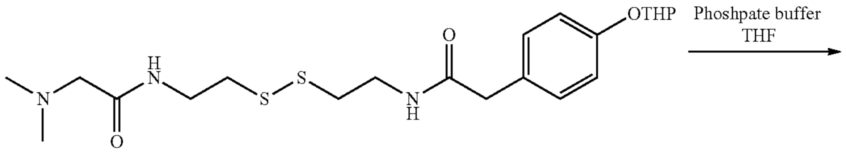

intermediate 15-a

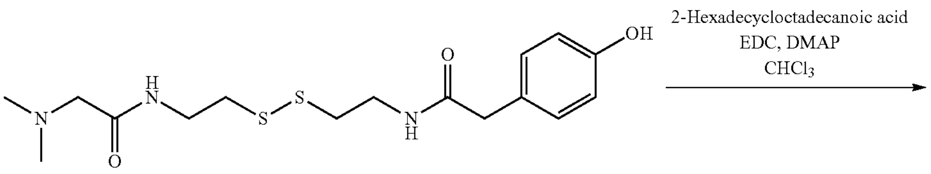

intermediate 16-a

-continued

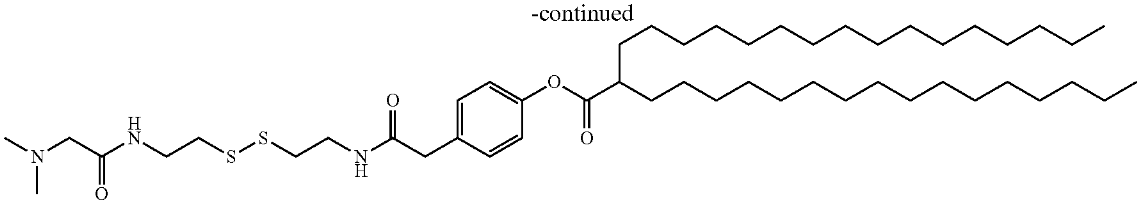

compound 18

[Example 18] Synthesis of Compound 18

Synthesis of Intermediate 15-a

Cystamine dihydrochloride (227 mg), DIPEA (391 mg) and dimethylglycine hydrochloride (141 mg) were dissolved in 4.54 g of methanol at room temperature. DMT-MM (837 mg) was added to the obtained solution and the mixture was reacted at 25° C. for 2 hr. Intermediate 1 (239 mg) was then added to the reaction solution and the mixture was reacted at 25° C. for 2 hr. After concentrating the reaction solution, 3.40 g of chloroform was added, and the solution was washed with 2.27 g of 0.5 M phosphate buffer (pH 6.0), 2.27 g of 7 wt % sodium bicarbonate water, and 2.27 g of 20 wt % brine in that order. 100 mg of sodium sulfate was added to the obtained solution to dehydrate it, and sodium sulfate was removed by filtration. The filtrate was concentrated in an evaporator to obtain 748 mg of intermediate 15-a as a crude product.

Synthesis of Intermediate 16-a

In the same manner as in intermediate 4-a of Example 1 except that a crude product of intermediate 15-a was used, intermediate 16-a was synthesized.

Synthesis of Compound 18

Using intermediate 16-a and 2-hexadecyloctadecanoic acid, compound 18 was synthesized by the same synthetic route as in Example 1.

$^1$H-NMR (600 MHz, $CDCl_3$) of Compound 18

δ:0.88 (t, 6H), 1.20-1.45 (m, 58H), 1.69-1.84 (m, 2H), 2.30 (s, 6H), 2.52-2.59 (m, 1H), 2.76-2.82 (m, 4H), 2.95 (s, 2H), 3.50-3.60 (m, 6H), 6.34 (s, 1H), 7.02-7.05 (m, 2H), 7.27-7.30 (m, 2H), 7.50 (s, 1H)

[Example 19] Synthesis of Compound 19

Synthesis of Intermediate 15-b

In the same manner as in Example 18 except that 3-(dimethylamino)propionic acid hydrochloride was used, intermediate 15-b represented by the following formula was synthesized.

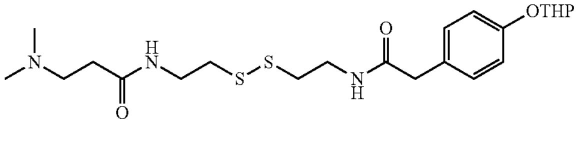

Synthesis of Intermediate 16-b

In the same manner as in Example 18 except that intermediate 15-b was used, intermediate 16-b represented by the following formula was synthesized.

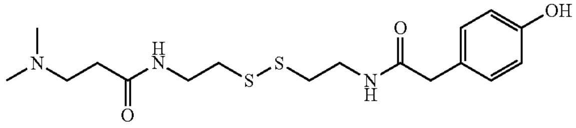 [SMILES: CN(C)CCC(=O)NCCSSCCNC(=O)Cc1ccc(O)cc1]

Synthesis of Compound 19

Using intermediate 16-b and 2-hexadecyloctadecanoic acid, compound 19 was synthesized by the same synthetic route as in Example 18.

$^1$H-NMR (600 MHz, $CDCl_3$) of Compound 19

δ:0.88 (t, 6H), 1.20-1.45 (m, 58H), 1.69-1.84 (m, 2H), 2.28 (s, 6H), 2.33-2.38 (m, 2H), 2.52-2.59 (m, 3H), 2.76-2.82 (m, 4H), 3.50-3.60 (m, 6H), 6.34 (s, 1H), 7.02-7.05 (m, 2H), 7.27-7.30 (m, 2H), 7.50 (s, 1H)

[Example 20] Synthesis of Compound 20

Synthesis of Intermediate 15-c

In the same manner as in Example 18 except that 4-(dimethylamino)butanoic acid hydrochloride was used, intermediate 15-c represented by the following formula was synthesized.

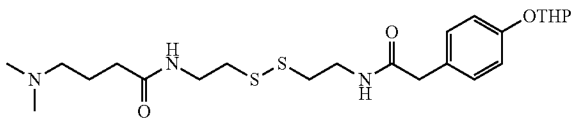

Synthesis of Intermediate 16-c

In the same manner as in Example 18 except that intermediate 15-c was used, intermediate 16-c represented by the following formula was synthesized.

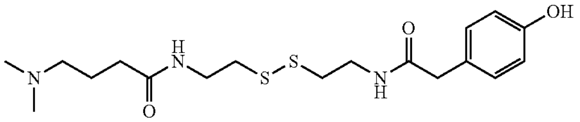 [SMILES: CN(C)CCCC(=O)NCCSSCCNC(=O)Cc1ccc(O)cc1]

Synthesis of Compound 20

Using intermediate 16-c and 2-hexadecyloctadecanoic acid, compound 20 was synthesized by the same synthetic route as in Example 18.

$^{1}$H-NMR (600 MHz, $CDCl_3$) of Compound 20

δ:0.88 (t, 6H), 1.20-1.45 (m, 58H), 1.69-1.80 (m, 4H), 2.25-2.38 (m, 8H), 2.52-2.59 (m, 1H), 2.76-2.82 (m, 4H), 3.50-3.60 (m, 6H), 6.34 (s, 1H), 7.02-7.05 (m, 2H), 7.27-7.30 (m, 2H), 7.50 (s, 1H)

Synthesis of Intermediate 18-a

In the same manner as in intermediate 4-a of Example 1 except that intermediate 17-a was used, intermediate 18-a was synthesized.

Synthesis of Compound 21

Using intermediate 18-a and 2-hexadecyloctadecanoic acid, compound 21 was synthesized by a method similar to that for compound 1 in Example 1.

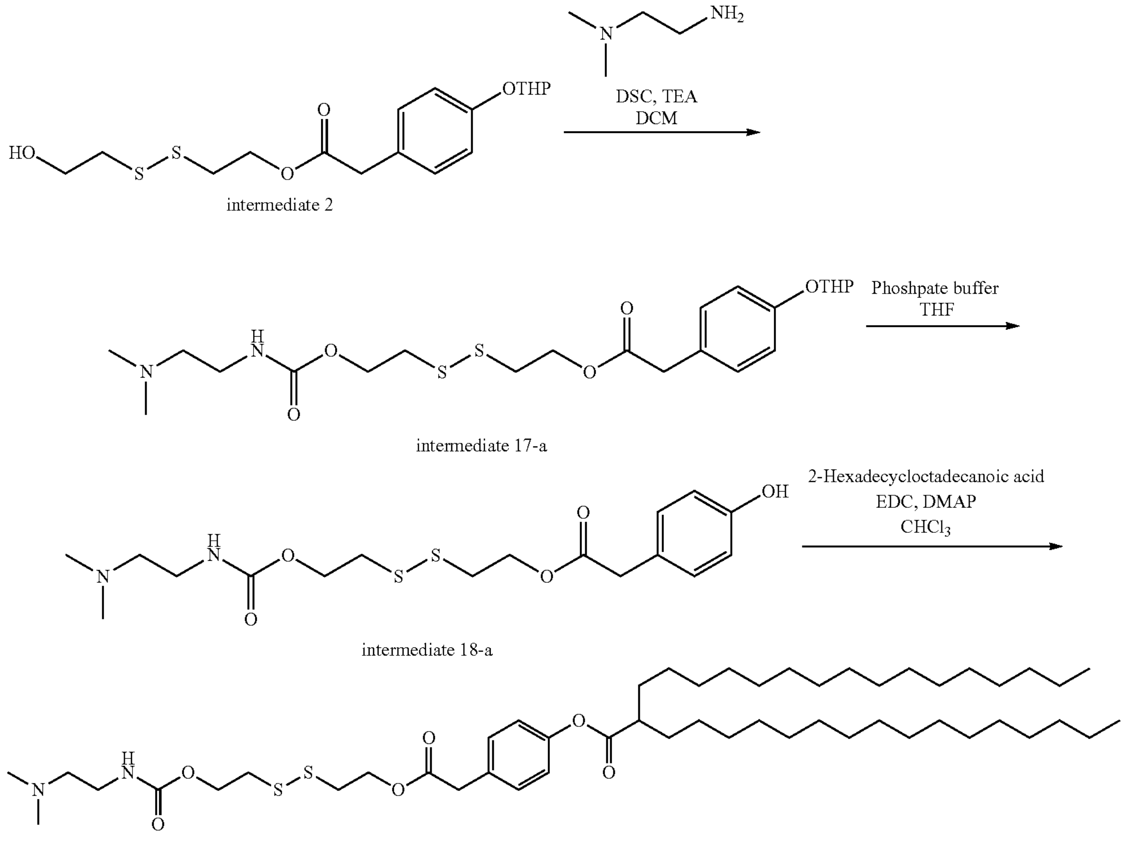

intermediate 2 intermediate 17-a intermediate 18-a compound 21

[Example 21] Synthesis of Compound 21

Synthesis of Intermediate 17-a 7.10 g of dichloromethane was added to intermediate 2 (393 mg) and triethylamine (235 mg) and dissolved at room temperature. DSC (541 mg) was added to the obtained solution and the mixture was reacted at 25° C. for 2 hr. After removing the DSC remaining in the reaction solution by filtration, N,N-dimethylethylenediamine (112 mg) was added to the filtrate and the mixture was reacted at 25° C. for 1 hr. After the reaction solution was washed with 5.90 g of 0.5 M acetate buffer (pH 4.0), 5.90 g of 7 wt % sodium bicarbonate water, and 5.90 g of 20 wt % brine in that order, 200 mg of sodium sulfate was added for dehydration. After removing the sodium sulfate by filtration, the filtrate was concentrated in an evaporator to obtain 472 mg of intermediate 17-a.

$^{1}$H-NMR (600 MHz, $CDCl_3$) of Compound 21

δ:0.88 (t, 6H), 1.20-1.45 (m, 58H), 1.69-1.84 (m, 2H), 2.22 (s, 6H), 2.38-2.42 (m, 2H), 2.52-2.59 (m, 1H), 2.88-2.97 (m, 4H), 3.22-3.26 (m, 2H), 3.63 (s, 2H), 4.28-4.38 (m, 4H), 5.26 (s, 1H), 7.02-7.05 (m, 2H), 7.27-7.30 (m, 2H)

[Example 22] Synthesis of Compound 22

Synthesis of Intermediate 17-b

In the same manner as in Example 21 except that N,N-diethylethylenediamine was used, intermediate 17-b represented by the following formula was synthesized.

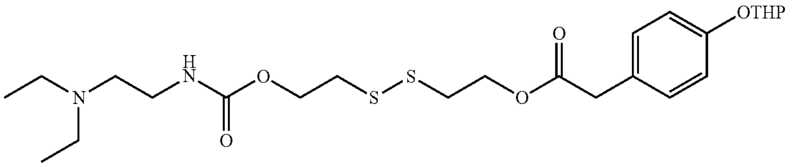

Synthesis of Intermediate 18-b

In the same manner as in Example 21 except that intermediate 17-b was used, intermediate 18-b represented by the following formula was synthesized.

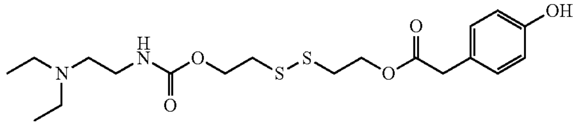 [SMILES: CCN(CC)CCNC(=O)OCCSSCCOC(=O)Cc1ccc(O)cc1]

Synthesis of Compound 22

Using intermediate 18-b and 2-hexadecyloctadecanoic acid, compound 22 was synthesized by the same synthetic route as in Example 21.

$^1$H-NMR (600 MHz, $CDCl_3$) of Compound 22

δ:0.88 (t, 6H), 1.00 (t, 6H), 1.20-1.45 (m, 58H), 1.69-1.84 (m, 2H), 2.47-2.57 (m, 7H), 2.88-2.97 (m, 4H), 3.22-3.26 (m, 2H), 3.63 (s, 2H), 4.28-4.38 (m, 4H), 5.28 (s, 1H), 7.02-7.05 (m, 2H), 7.27-7.30 (m, 2H)

[Example 23] Synthesis of Compound 23

Synthesis of Intermediate 17-c

In the same manner as in Example 21 except that N,N-dimethyl-1,3-propanediamine was used, intermediate 17-c represented by the following formula was synthesized.

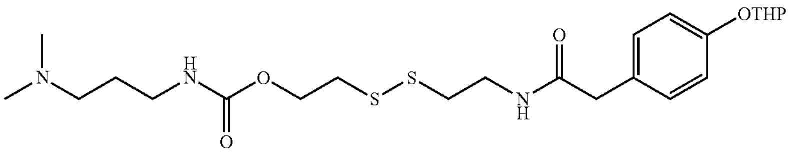

Synthesis of Intermediate 18-c

In the same manner as in Example 21 except that intermediate 17-c was used, intermediate 18-c represented by the following formula was synthesized.

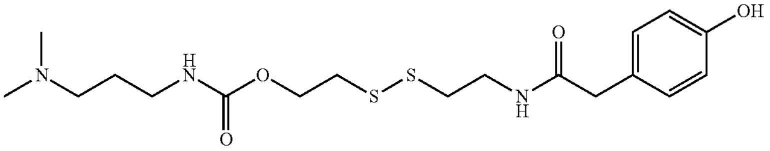 [SMILES: CN(C)CCCNC(=O)OCCSSCCNC(=O)Cc1ccc(O)cc1]

Synthesis of Compound 23

Using intermediate 18-c and 2-hexadecyloctadecanoic acid, compound 23 was synthesized by the same synthetic route as in Example 21.

$^1$H-NMR (600 MHz, $CDCl_3$) of Compound 23

δ:0.88 (t, 6H), 1.20-1.45 (m, 58H), 1.69-1.84 (m, 4H), 2.24 (s, 6H), 2.38-2.42 (m, 2H), 2.52-2.59 (m, 1H), 2.88-2.97 (m, 4H), 3.22-3.26 (m, 2H), 3.63 (s, 2H), 4.28-4.38 (m, 4H), 5.70 (s, 1H), 7.02-7.05 (m, 2H), 7.27-7.30 (m, 2H)

[Example 24] Synthesis of Compound 24

Synthesis of Intermediate 17-d

In the same manner as in Example 21 except that N,N,N'-trimethyl-1,3-propanediamine was used, intermediate 17-d represented by the following formula was synthesized.

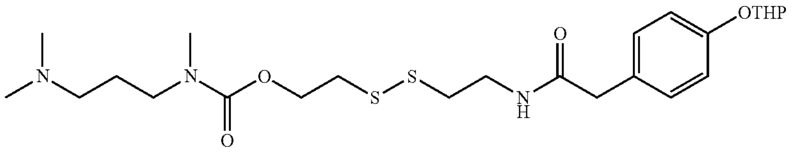

Synthesis of Intermediate 18-d

In the same manner as in Example 21 except that intermediate 17-d was used, intermediate 18-d represented by the following formula was synthesized.

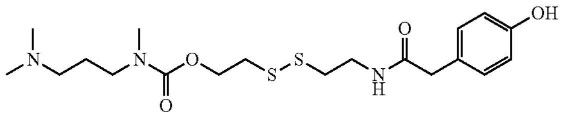

Synthesis of Compound 24

Using intermediate 18-d and 2-hexadecyloctadecanoic acid, compound 24 was synthesized by the same synthetic route as in Example 21.

$^1$H-NMR (600 MHz, $CDCl_3$) of Compound 24

δ:0.88 (t, 6H), 1.20-1.45 (m, 58H), 1.69-1.84 (m, 4H), 2.24 (s, 6H), 2.38-2.42 (m, 2H), 2.52-2.59 (m, 1H), 2.88-2.97 (m, 7H), 3.22-3.26 (m, 2H), 3.63 (s, 2H), 4.28-4.38 (m, 4H), 7.02-7.05 (m, 2H), 7.27-7.30 (m, 2H)

[Example 25] Synthesis of Compound 25

Synthesis of Intermediate 17-e

In the same manner as in Example 21 except that N,N-dimethyl-1,4-butanediamine was used, intermediate 17-e represented by the following formula was synthesized.

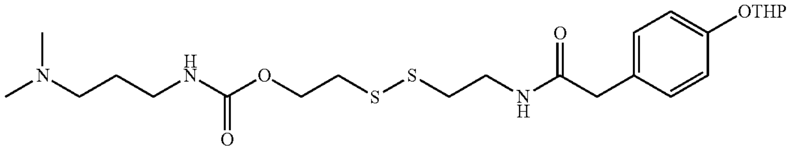

Synthesis of Intermediate 18-e

In the same manner as in Example 21 except that intermediate 17-e was used, intermediate 18-e represented by the following formula was synthesized.

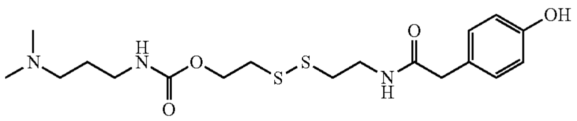 [SMILES: CN(C)CCCNC(=O)OCCSSCCNC(=O)Cc1ccc(O)cc1]

Synthesis of Compound 25

Using intermediate 18-e and 2-hexadecyloctadecanoic acid, compound 25 was synthesized by the same synthetic route as in Example 21.

$^1$H-NMR (600 MHz, $CDCl_3$) of Compound 25

δ:0.88 (t, 6H), 1.20-1.45 (m, 58H), 1.50-1.62 (m, 4H), 1.69-1.84 (m, 2H), 2.20-2.42 (m, 8H), 2.52-2.59 (m, 1H), 2.88-2.97 (m, 4H), 3.22-3.26 (m, 2H), 3.63 (s, 2H), 4.28-4.38 (m, 4H), 5.70 (s, 1H), 7.02-7.05 (m, 2H), 7.27-7.30 (m, 2H)

[Example 26] Synthesis of Compound 26

Synthesis of Intermediate 17-f

In the same manner as in Example 21 except that 4-(2-aminoethyl)morpholine was used, intermediate 17-f represented by the following formula was synthesized.

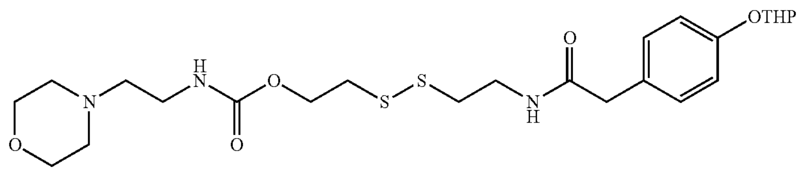

Synthesis of Intermediate 18-f

In the same manner as in Example 21 except that intermediate 17-f was used, intermediate 18-f represented by the following formula was synthesized.

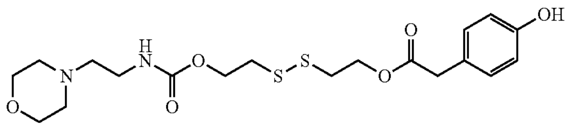 [SMILES: O=C(Cc1ccc(O)cc1)OCCSSCCOC(=O)NCCN1CCOCC1]

Synthesis of Compound 26

Using intermediate 18-f and 2-hexadecyloctadecanoic acid, compound 26 was synthesized by the same synthetic route as in Example 21.

$^1$H-NMR (600 MHz, $CDCl_3$) of Compound 26

δ:0.88 (t, 6H), 1.20-1.45 (m, 58H), 1.69-1.84 (m, 2H), 2.40-2.46 (m, 6H), 2.52-2.59 (m, 1H), 2.88-2.97 (m, 4H), 3.22-3.26 (m, 2H), 3.63 (s, 2H), 4.28-4.38 (m, 4H), 5.26 (s, 1H), 7.02-7.05 (m, 2H), 7.27-7.30 (m, 2H)

[Example 27] Synthesis of Compound 27

Synthesis of Intermediate 17-g

In the same manner as in Example 21 except that N,N-dibutylethylenediamine was used, intermediate 17-g represented by the following formula was synthesized.

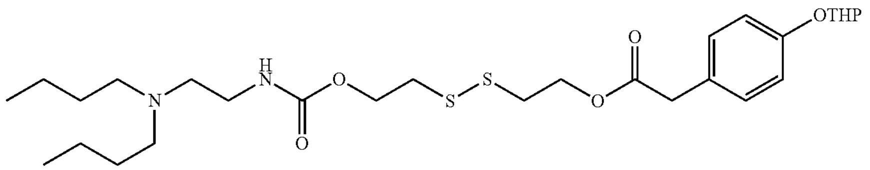

Synthesis of Intermediate 18-g

In the same manner as in Example 21 except that intermediate 17-g was used, intermediate 18-g represented by the following formula was synthesized.

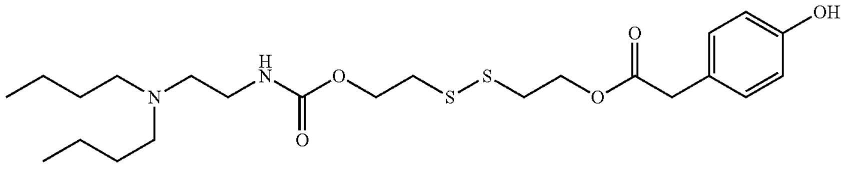 [SMILES: CCCCN(CCCC)CCNC(=O)OCCSSCCOC(=O)Cc1ccc(O)cc1]

Synthesis of Compound 27

Using intermediate 18-g and 2-hexadecyloctadecanoic acid, compound 27 was synthesized by the same synthetic route as in Example 21.

$^1$H-NMR (600 MHz, $CDCl_3$) of Compound 27

δ:0.87-0.93 (m, 12H), 1.20-1.45 (m, 66H), 1.69-1.84 (m, 2H), 2.39-2.57 (m, 7H), 2.88-2.97 (m, 4H), 3.22-3.26 (m, 2H), 3.63 (s, 2H), 4.28-4.38 (m, 4H), 5.28 (s, 1H), 7.02-7.05 (m, 2H), 7.27-7.30 (m, 2H)

[Example 28] Synthesis of Compound 28

Synthesis of Intermediate 17-h

In the same manner as in Example 21 except that N,N-diisopropylethylenediamine was used, intermediate 17-h represented by the following formula was synthesized.

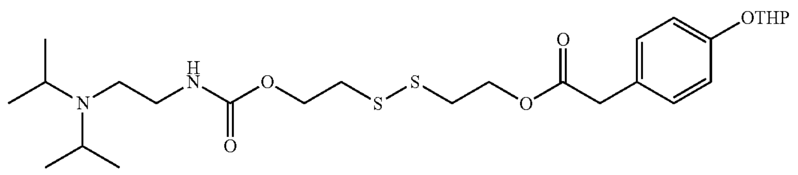

Synthesis of Intermediate 18-h

In the same manner as in Example 21 except that intermediate 17-h was used, intermediate 18-h represented by the following formula was synthesized.

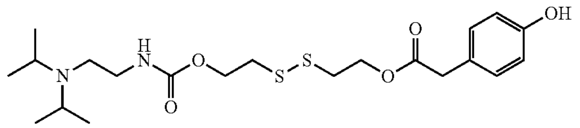 [SMILES: CC(C)N(CCNC(=O)OCCSSCCOC(=O)Cc1ccc(O)cc1)C(C)C]

Synthesis of Compound 28

Using intermediate 18-h and 2-hexadecyloctadecanoic acid, compound 28 was synthesized by the same synthetic route as in Example 21.

$^1$H-NMR (600 MHz, $CDCl_3$) of Compound 28

δ:0.88 (t, 6H), 0.95-1.03 (d, 12H), 1.20-1.45 (m, 58H), 1.60-1.84 (m, 6H), 2.52-2.59 (m, 1H), 2.88-3.00 (m, 6H), 3.22-3.26 (m, 2H), 3.63 (s, 2H), 4.28-4.38 (m, 4H), 5.28 (s, 1H), 7.02-7.05 (m, 2H), 7.27-7.30 (m, 2H)

[Example 29] Synthesis of Compound 29

Synthesis of Intermediate 17-i

In the same manner as in Example 21 except that N,N-diethyl-N'-methylethylenediamine was used, intermediate 17-i represented by the following formula was synthesized.

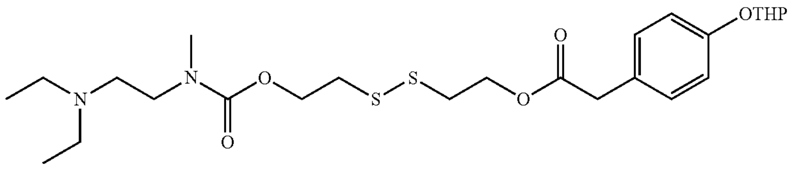

Synthesis of Intermediate 18-i

In the same manner as in Example 21 except that intermediate 17-i was used, intermediate 18-i represented by the following formula was synthesized.

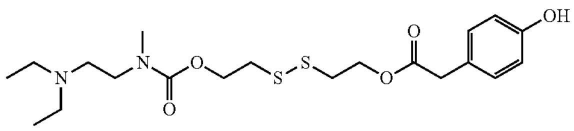 [SMILES: CCN(CC)CCN(C)C(=O)OCCSSCCOC(=O)Cc1ccc(O)cc1]

Synthesis of Compound 29

Using intermediate 18-i and 2-hexadecyloctadecanoic acid, compound 29 was synthesized by the same synthetic route as in Example 21.

$^1$H-NMR (600 MHz, $CDCl_3$) of Compound 29

δ:0.88 (t, 6H), 1.00 (t, 6H), 1.20-1.45 (m, 58H), 1.69-1.84 (m, 2H), 2.47-2.57 (m, 7H), 2.88-2.97 (m, 7H), 3.22-3.26 (m, 2H), 3.63 (s, 2H), 4.28-4.38 (m, 4H), 5.28 (s, 1H), 7.02-7.05 (m, 2H), 7.27-7.30 (m, 2H)

tion and the mixture was reacted at 25° C. for 2 hr. DMAP (33.0 mg) and 2-(dimethylamino)ethanol (976 mg) were added to this reaction solution and the mixture was reacted at 25° C. for 6 hr. After the reaction, the solution was washed with 5.10 g of 0.5 M acetate buffer (pH 4.0), 5.10 g of 7 wt % sodium bicarbonate water, and 5.10 g of 20 wt % brine, in that order, and then dehydrated by adding 250 mg of sodium sulfate. After removing the sodium sulfate by filtration, the filtrate was concentrated in an evaporator to obtain 287 mg of intermediate 19.

Synthesis of Intermediate 20

In the same manner as in intermediate 4-a of Example 1 except that intermediate 19 was used, intermediate 20 was synthesized.

Synthesis of Compound 30

Using intermediate 20 and 2-hexadecyloctadecanoic acid, compound 30 was synthesized by a method similar to that for compound 1 in Example 1.

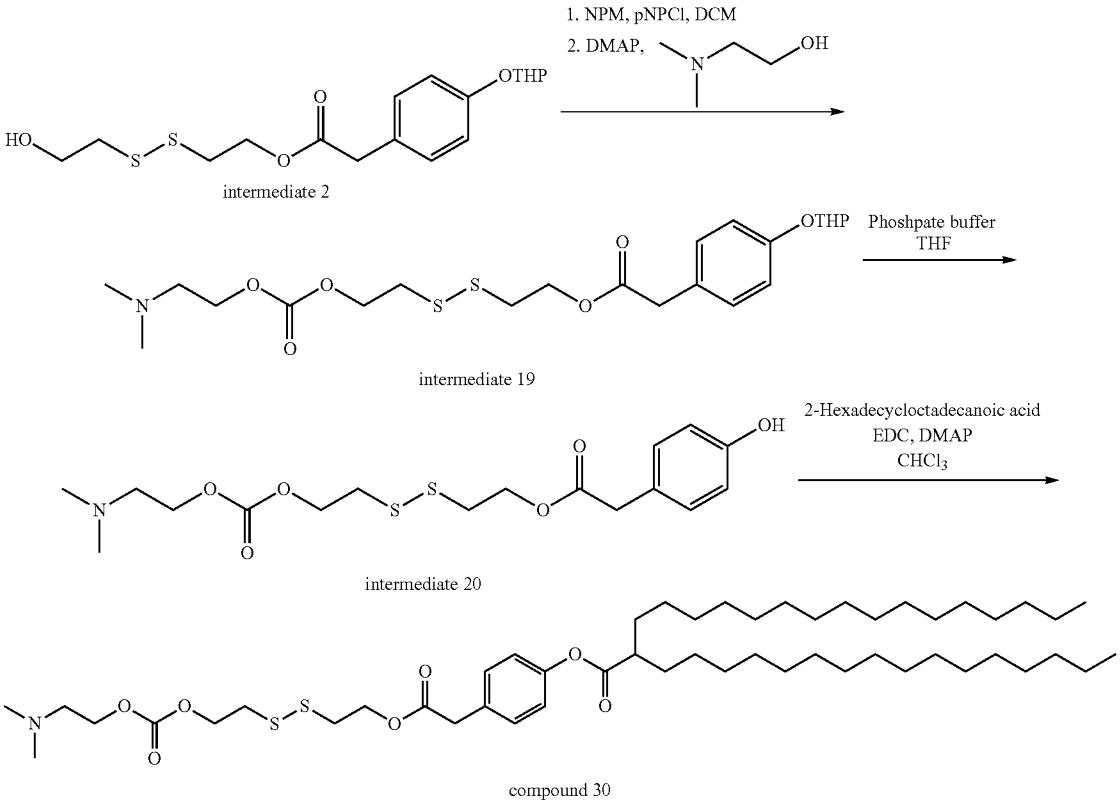

[Example 30] Synthesis of Compound 30

Synthesis of Intermediate 19

5.10 g of dichloromethane was added to intermediate 2 (510 mg) and NPM (670 mg) and dissolved at room temperature. pNPCl (690 mg) was added to the obtained solu- $^1$H-NMR (600 MHz, $CDCl_3$) of Compound 30

δ:0.88 (t, 6H), 1.20-1.45 (m, 58H), 1.69-1.84 (m, 2H), 2.28 (s, 6H), 2.58-2.61 (m, 3H), 2.91-2.94 (m, 4H), 3.63 (s, 2H), 4.23 (t, 2H), 4.32-4.38 (m, 4H), 7.02-7.05 (m, 2H), 7.27-7.30 (m, 2H)

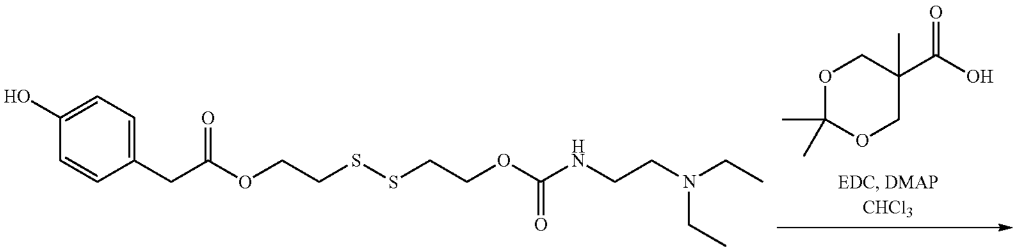

intermediate 18-b

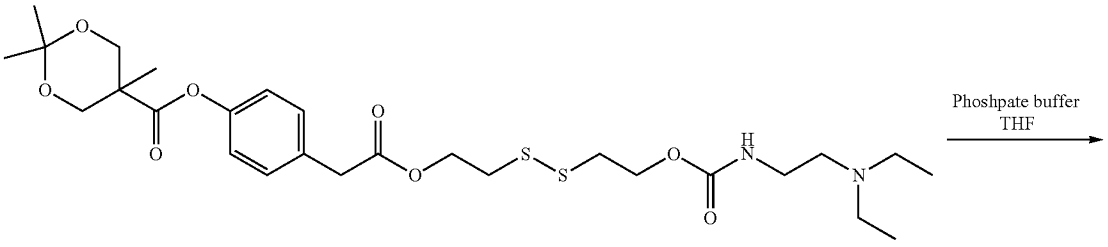

intermediate 21

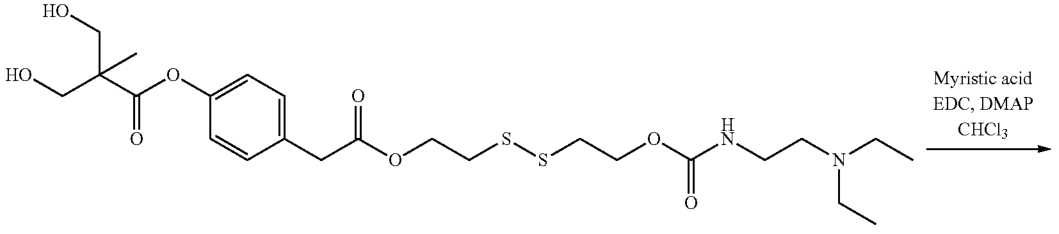

intermediate 22

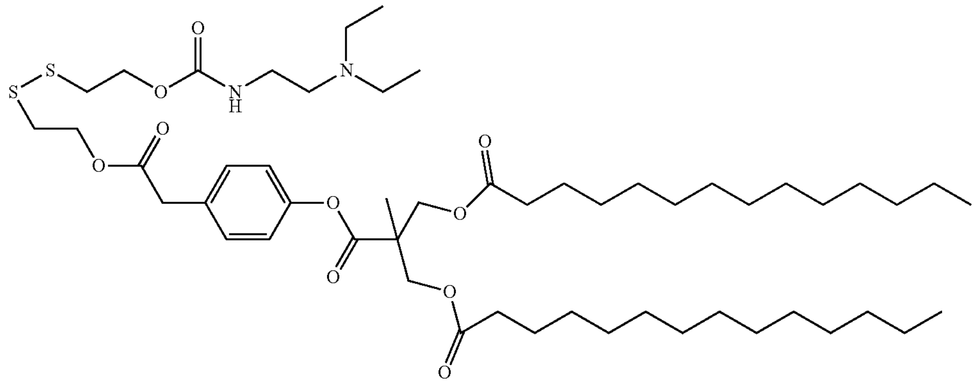

compound 31

[Example 31] Synthesis of Compound 31

Synthesis of Intermediate 21

Intermediate 18-b (1.00 g), 2,2,5-trimethyl-1,3-dioxane-5-carboxylic acid (445 mg) and DMAP (57.0 mg) were dissolved in 15.0 g of chloroform at room temperature. EDC (668 mg) was added to the obtained solution and the mixture was reacted at 25° C. for 2 hr. The reaction solution was washed with 10.0 g of 20 wt % brine, and then dehydrated by adding 500 mg of sodium sulfate. After removing the sodium sulfate by filtration, the filtrate was concentrated in an evaporator and purified with a column to obtain 1.25 g of intermediate 21.

Synthesis of Intermediate 22

Intermediate 21 (1.25 g) was dissolved in 11.3 g of THF, and then 45.0 g of 0.5 M phosphate buffer (pH 2.0) was added and the mixture was reacted at 40° C. for 22 hr. 18.8 g of chloroform was added to the reaction solution for washing. After washing, 400 g/L aqueous sodium hydroxide solution was added to the aqueous layer, and the pH was adjusted to 6.0, and the aqueous layer was extracted with 18.8 g of chloroform. 600 mg of sodium sulfate was added to the extracted organic layer for dehydration, and sodium sulfate was removed by filtration. The filtrate was concentrated in an evaporator to obtain 908 mg of intermediate 22.

Synthesis of Compound 31

Intermediate 22 (200 mg), myristic acid (175 mg), and DMAP (18.0 mg) were dissolved in 3.00 g of chloroform at room temperature. EDC (175 mg) was added to the obtained solution and the mixture was reacted at 25° C. for 2 hr. The reaction solution was concentrated using an evaporator and purified with a column to obtain 106 mg of compound 31.

$^1$H-NMR (600 MHz, $CDCl_3$) of Compound 31

δ:0.89 (t, 6H), 1.04 (t, 6H), 1.25-1.35 (m, 40H), 1.42 (s, 3H), 1.55-1.65 (m, 4H), 2.36 (t, 4H), 2.52-2.58 (m, 6H), 2.92-2.96 (m, 4H), 3.22-3.26 (m, 2H), 3.66 (s, 2H), 4.30-4.40 (m, 8H), 5.28 (s, 1H), 7.02-7.05 (m, 2H), 7.27-7.30 (m, 2H)

[Example 32] Synthesis of Compound 32

Synthesis of Compound 32

Using intermediate 22 and palmitic acid, compound 32 was synthesized by the same synthetic route as in Example 31.

$^1$H-NMR (600 MHz, $CDCl_3$) of Compound 32

δ:0.89 (t, 6H), 1.04 (t, 6H), 1.25-1.35 (m, 48H), 1.42 (s, 3H), 1.55-1.65 (m, 4H), 2.36 (t, 4H), 2.52-2.58 (m, 6H), 2.92-2.96 (m, 4H), 3.22-3.26 (m, 2H), 3.66 (s, 2H), 4.30-4.40 (m, 8H), 5.28 (s, 1H), 7.02-7.05 (m, 2H), 7.27-7.30 (m, 2H)

[Example 33] Synthesis of Compound 33

Synthesis of Compound 33

Using intermediate 22 and stearic acid, compound 33 was synthesized by the same synthetic route as in Example 31.

$^1$H-NMR (600 MHz, $CDCl_3$) of Compound 33

δ:0.89 (t, 6H), 1.04 (t, 6H), 1.25-1.35 (m, 56H), 1.42 (s, 3H), 1.55-1.65 (m, 4H), 2.36 (t, 4H), 2.52-2.58 (m, 6H), 2.92-2.96 (m, 4H), 3.22-3.26 (m, 2H), 3.66 (s, 2H), 4.30-4.40 (m, 8H), 5.28 (s, 1H), 7.02-7.05 (m, 2H), 7.27-7.30 (m, 2H)

[Example 34] Synthesis of Compound 34

Synthesis of Compound 34

Using intermediate 22 and oleic acid, compound 34 was synthesized by the same synthetic route as in Example 31.

$^1$H-NMR (600 MHz, $CDCl_3$) of Compound 34

δ:0.89 (t, 6H), 1.04 (t, 6H), 1.25-1.38 (m, 40H), 1.42 (s, 3H), 1.55-1.65 (m, 4H), 1.99-2.05 (m, 8H), 2.36 (t, 4H), 2.52-2.58 (m, 6H), 2.92-2.96 (m, 4H), 3.22-3.26 (m, 2H), 3.66 (s, 2H), 4.30-4.40 (m, 8H), 5.32-5.38 (m, 5H), 7.02-7.05 (m, 2H), 7.27-7.30 (m, 2H)

[Example 35] Synthesis of Compound 35

Synthesis of Compound 35

Using intermediate 22 and linoleic acid, compound 35 was synthesized by the same synthetic route as in Example 31.

$^1$H-NMR (600 MHz, $CDCl_3$) of Compound 35

δ:0.89 (t, 6H), 1.04 (t, 6H), 1.25-1.38 (m, 28H), 1.42 (s, 3H), 1.55-1.65 (m, 4H), 1.99-2.05 (m, 8H), 2.36 (t, 4H), 2.52-2.58 (m, 6H), 2.75-2.78 (m, 4H), 2.92-2.96 (m, 4H), 3.22-3.26 (m, 2H), 3.66 (s, 2H), 4.30-4.40 (m, 8H), 5.32-5.38 (m, 9H), 7.02-7.05 (m, 2H), 7.27-7.30 (m, 2H)

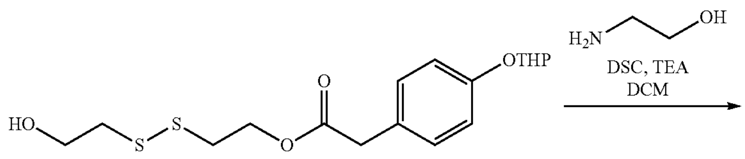

intermediate 2

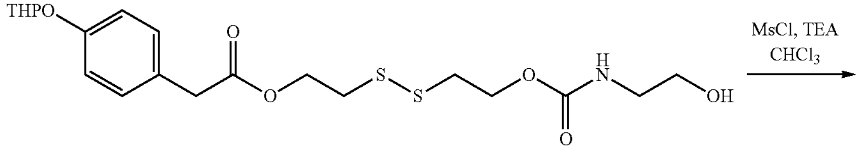

intermediate 23

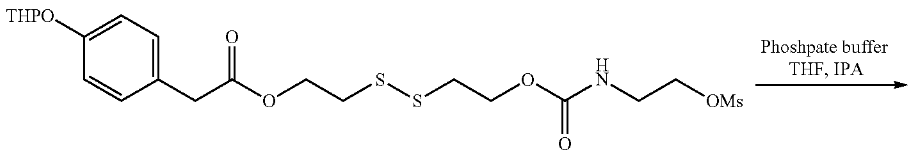

intermediate 24

-continued
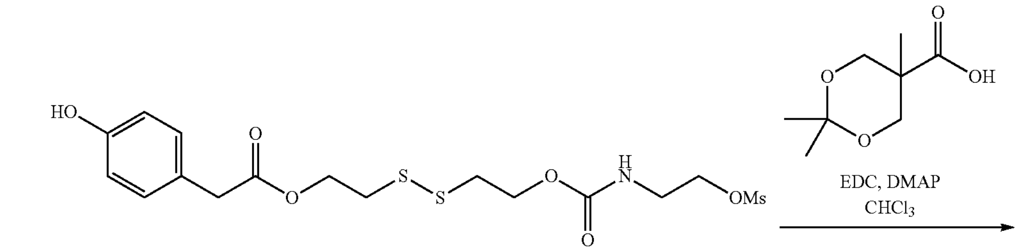
intermediate 25
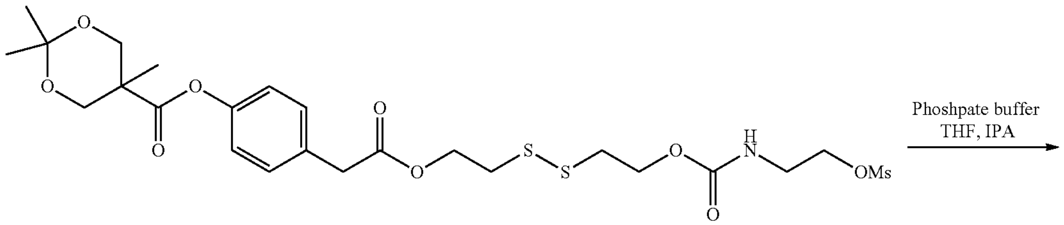
intermediate 26
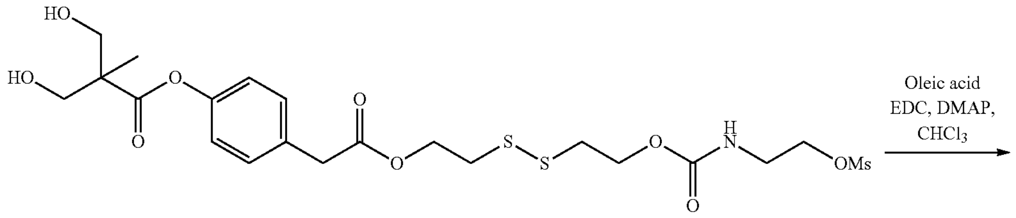
intermediate 27
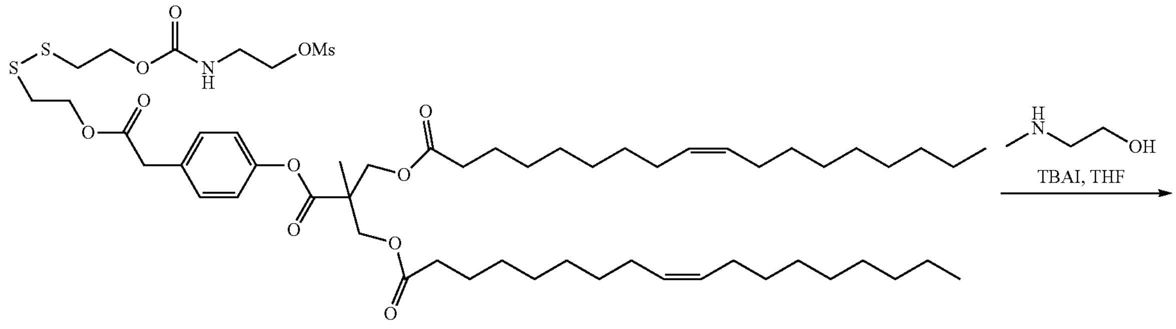
intermediate 28
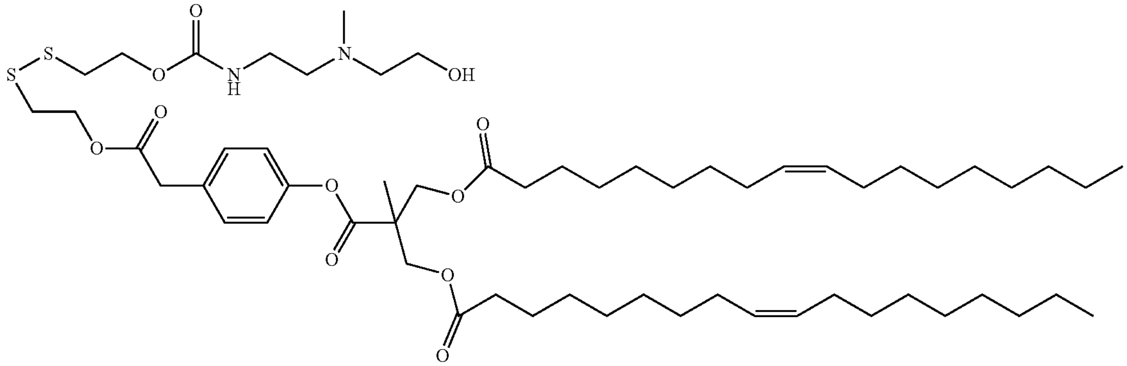
compound 36

[Example 36] Synthesis of Compound 36

Synthesis of Intermediate 23

Intermediate 2 (2.0 g) and triethylamine (1.20 g) were added with 36.0 g of dichloromethane and dissolved at room temperature. DSC (2.75 g) was added to the obtained solution and the mixture was reacted at 25° C. for 2 hr. After removing the DSC remaining in the reaction solution by filtration, ethanolamine (394 mg) was added to the filtrate and the mixture was reacted at 25° C. for 1 hr. The solution after the reaction was washed with 30.0 g of 0.5 M acetate buffer (pH 4.0), and then 1.00 g of sodium sulfate was added to dehydrate it. After removing the sodium sulfate by filtration, the filtrate was concentrated using an evaporator to obtain 1.41 g of intermediate 23.

Synthesis of Intermediate 24

Intermediate 23 (1.35 g) and triethylamine (594 mg) were dissolved in 20.0 g of chloroform at room temperature. Methanesulfonyl chloride (505 mg) was added to the obtained solution and the mixture was reacted at room temperature for 3 hr. The reaction solution was washed with 15.0 g of 7 wt % sodium bicarbonate water, and 500 mg of sodium sulfate was added for dehydration. After removing the sodium sulfate by filtration, the filtrate was concentrated in an evaporator to obtain 1.34 g of intermediate 24.

Synthesis of Intermediate 25

Intermediate 2 (1.31 g) was dissolved in a mixed solvent of 11.8 g of THF and 13.1 g of IPA, and then 47.2 g of 0.5 M phosphate buffer (pH 2.0) was added and the mixture was reacted at 40° C. for 2 hr. The reaction solution was washed with 19.7 g of chloroform. After washing, 400 g/L aqueous sodium hydroxide solution was added to the aqueous layer to neutralize it, and then 19.7 g of chloroform was added to the aqueous layer for extraction. 3.0 g of sodium sulfate was added to the extracted organic layer to dehydrate it, and sodium sulfate was removed by filtration. The filtrate was concentrated in an evaporator to obtain 939 mg of intermediate 25.

Synthesis of Intermediate 26

Intermediate 25 (930 mg), 2,2,5-trimethyl-1,3-dioxane-5-carboxylic acid (393 mg) and DMAP (50.0 mg) were dissolved in g of chloroform at room temperature. EDC (590 mg) was added to the obtained solution and the mixture was reacted at 25° C. for 2 hr. The reaction solution was washed with 9.30 g of 20 wt % brine, and then 500 mg of sodium sulfate was added to dehydrate it. After sodium sulfate was removed by filtration, the filtrate was concentrated in an evaporator and purified with a column to obtain 1.06 g of intermediate 26.

Synthesis of Intermediate 27

Intermediate 26 (1.00 g) was dissolved in a mixed solvent of 9.00 g THF and 9.00 g IPA, and then 40.0 g of 0.5 M phosphate buffer (pH 2.0) was added and the mixture was reacted at 40° C. for 2 hr. 15.0 g of chloroform was added to the reaction solution for washing. After washing, 400 g/L aqueous sodium hydroxide solution was added to the aqueous layer to neutralize it, and 15.0 g of chloroform was added to the aqueous layer for extraction. 500 mg of sodium sulfate was added to the organic layer for dehydration, and sodium sulfate was removed by filtration. The filtrate was concentrated in an evaporator to obtain 785 mg of intermediate 27.

Synthesis of Intermediate 28

Intermediate 27 (770 mg), oleic acid (802 mg), and DMAP (66.0 mg) were dissolved in 11.6 g of chloroform at room temperature. EDC (648 mg) was added to the obtained solution and the mixture was reacted at 25° C. for 2 hr. The reaction solution was washed with 8.00 g of 20 wt % brine, and then 2.0 g of sodium sulfate was added for dehydration. After removing the sodium sulfate by filtration, the filtrate was concentrated in an evaporator and purified with a column to obtain 1.15 g of intermediate 28.

Synthesis of Compound 36

Intermediate 28 (250 mg) was dissolved in 2.50 g of THF, and 2-(methylamino)ethanol (137 mg) and TBAI (17.0 mg) were added and the mixture was reacted at 40° C. for 8 hr. 3.75 g of chloroform was added to the reaction solution, which was washed in the order of 2.50 g of 0.5 M acetate buffer (pH 4.0), 2.50 g of 7 wt % sodium bicarbonate water, and 2.50 g of 20 wt % brine. The filtrate was concentrated in an evaporator and purified with a column to obtain 79 mg of compound 36.

$^{1}$H-NMR (600 MHz, $CDCl_3$) of Compound 36

δ:0.89 (t, 6H), 1.25-1.38 (m, 40H), 1.42 (s, 3H), 1.55-1.65 (m, 4H), 1.99-2.05 (m, 8H), 2.30-2.40 (m, 7H), 2.52-2.58 (m, 4H), 2.92-2.96 (m, 4H), 3.22-3.26 (m, 2H), 3.58-3.63 (m, 4H), 4.30-4.40 (m, 8H), 5.32-5.38 (m, 5H), 7.02-7.05 (m, 2H), 7.27-7.30 (m, 2H)

[Example 37] Synthesis of Compound 37

Synthesis of Compound 37

Using intermediate 28 and 3-(methylamino)-1-propanol, compound 37 was synthesized by the same synthetic route as in Example 36.

$^{1}$H-NMR (600 MHz, $CDCl_3$) of Compound 37

δ:0.89 (t, 6H), 1.25-1.38 (m, 40H), 1.42 (s, 3H), 1.55-1.72 (m, 6H), 1.99-2.05 (m, 8H), 2.30-2.40 (m, 7H), 2.52-2.58 (m, 4H), 2.92-2.96 (m, 4H), 3.22-3.26 (m, 2H), 3.58-3.63 (m, 4H), 4.30-4.40 (m, 8H), 5.32-5.38 (m, 5H), 7.02-7.05 (m, 2H), 7.27-7.30 (m, 2H)

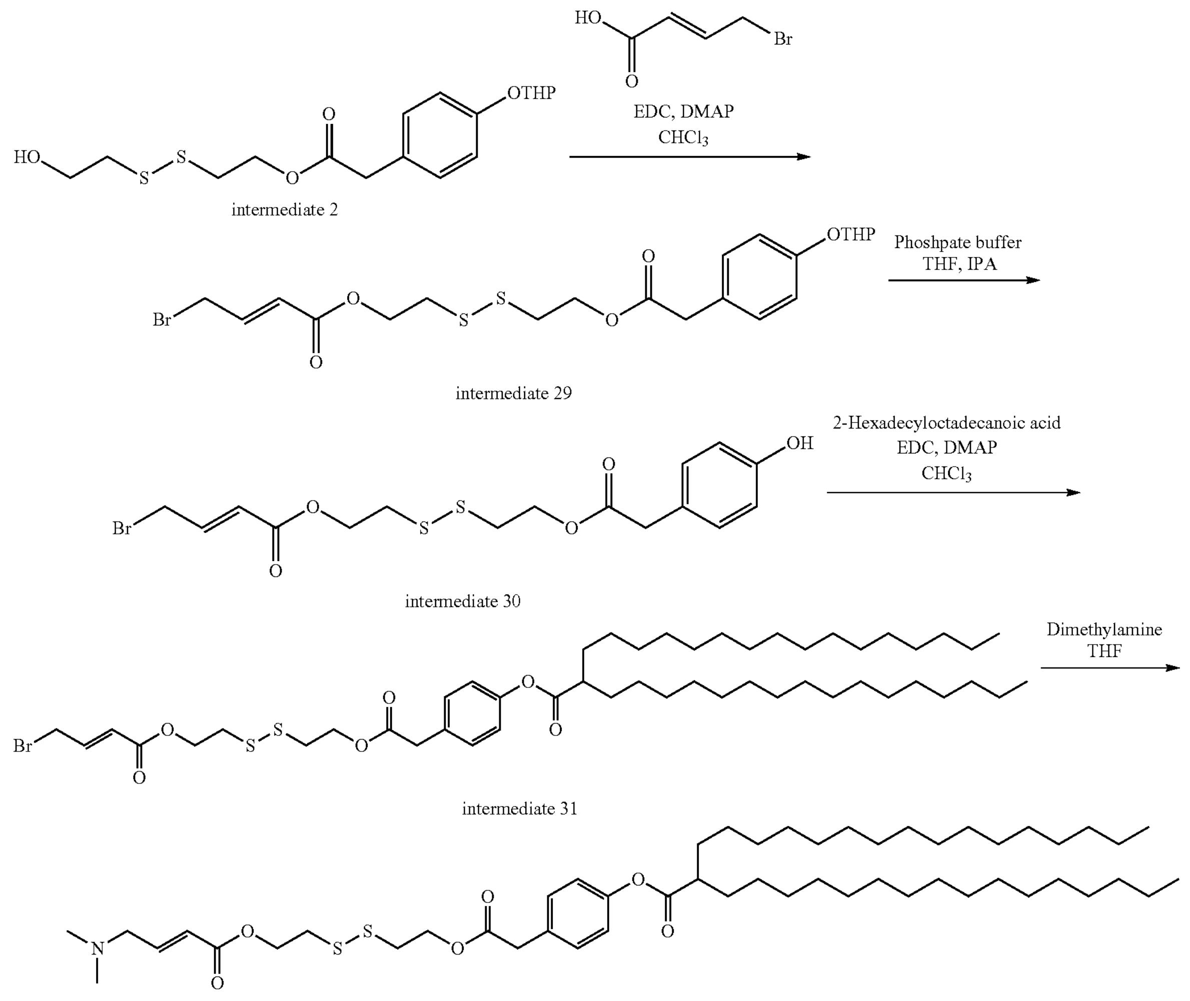

intermediate 2 intermediate 29 intermediate 30 intermediate 31 compound 38

[Example 38] Synthesis of Compound 38

Synthesis of Intermediate 29

Intermediate 2 (2.00 g), (E)-4-bromocrotonic acid (974 mg), and DMAP (131 mg) were dissolved in 30.0 g of chloroform at room temperature. EDC (1.54 g) was added to the obtained solution and the mixture was reacted at 25° C. for 2 hr. The reaction solution was washed with 9.0 mL of 20 wt % brine, and then 2.0 g of sodium sulfate was added for dehydration. After removing the sodium sulfate by filtration, the filtrate was concentrated in an evaporator to obtain 2.26 g of intermediate 29.

Synthesis of Intermediate 30

Intermediate 29 (2.25 g) was dissolved in a mixed solvent of 20.23 g of THF and 22.5 g of IPA, and then 81.0 g of 0.5 M phosphate buffer (pH 2.0) was added and the mixture was reacted at 40° C. for 2 hr. The reaction solution was washed with 34.0 g of chloroform. After washing, 400 g/L aqueous sodium hydroxide solution was added to the aqueous layer to neutralize it, and then 34.0 g of chloroform was added to the aqueous layer for extraction. 1.00 g of sodium sulfate was added to the extracted organic layer to dehydrate it, and the sodium sulfate was removed by filtration. The filtrate was concentrated using an evaporator to obtain 1.51 g of intermediate 30.

Synthesis of Intermediate 31

Intermediate 30 (1.40 g), 2-hexadecyloctadecanoic acid (1.80 g), and DMAP (79.0 mg) were dissolved in 21.0 g of chloroform at room temperature. EDC (925 mg) was added to the obtained solution and the mixture was reacted at 25° C. for 2 hr. The reaction solution was concentrated using an evaporator to obtain 2.98 g of a crude product of intermediate 31.

Synthesis of Compound 38

500 mg of the crude product of intermediate 31 and 2.30 g of dimethylamine (2.0 mol/L in THF) were dissolved in 5.00 g of THF, and potassium iodide (0.12 mmol) was added and the mixture was reacted at 25° C. for 10 hr. After removing insoluble matter by filtration, 7.50 g of chloroform was added to the filtrate, the mixture was then washed with 5.00 g of 0.5 M acetate buffer (pH 4.0), 5.00 g of 7 wt % sodium bicarbonate water, and 5.00 g of 20 wt % brine, in that order. After adding 250 mg of sodium sulfate for dehydration, the sodium sulfate was removed by filtration. The filtrate was concentrated using an evaporator and purified with a column to obtain 270 mg of compound 38.

$^1$H-NMR (600 MHz, $CDCl_3$) of Compound 38

δ:0.88 (t, 6H), 1.20-1.45 (m, 58H), 1.69-1.84 (m, 2H), 2.25 (s, 6H), 2.52-2.59 (m, 1H), 2.88-2.97 (m, 4H), 3.07 (t, 2H), 3.63 (s, 2H), 4.28-4.38 (m, 4H), 5.97-6.00 (m, 1H), 6.95-7.05 (m, 3H), 7.27-7.30 (m, 2H)

[Example 39] Synthesis of Compound 39

Synthesis of Compound 39

In the same manner as in Example 38 except that diethylamine was used, compound 39 was synthesized.

$^1$H-NMR (600 MHz, $CDCl_3$) of Compound 39

δ:0.88 (t, 6H), 1.03 (t, 6H), 1.20-1.45 (m, 58H), 1.69-1.84 (m, 2H), 2.50-2.59 (m, 5H), 2.88-2.97 (m, 4H), 3.23 (t, 2H), 3.63 (s, 2H), 4.28-4.38 (m, 4H), 5.97-6.00 (m, 1H), 6.95-7.05 (m, 3H), 7.27-7.30 (m, 2H)

[Example 40] Synthesis of Compound 40

Synthesis of Compound 40

In the same manner as in Example 38 except that 2-(ethylamino)ethanol was used, compound 40 was synthesized.

$^1$H-NMR (600 MHz, $CDCl_3$) of Compound 40

δ:0.88 (t, 6H), 1.03 (t, 3H), 1.20-1.45 (m, 58H), 1.69-1.84 (m, 2H), 2.50-2.59 (m, 5H), 2.88-2.97 (m, 4H), 3.23 (t, 2H), 3.55-3.58 (m, 2H), 3.63 (s, 2H), 4.28-4.38 (m, 4H), 5.97-6.00 (m, 1H), 6.95-7.05 (m, 3H), 7.27-7.30 (m, 2H)

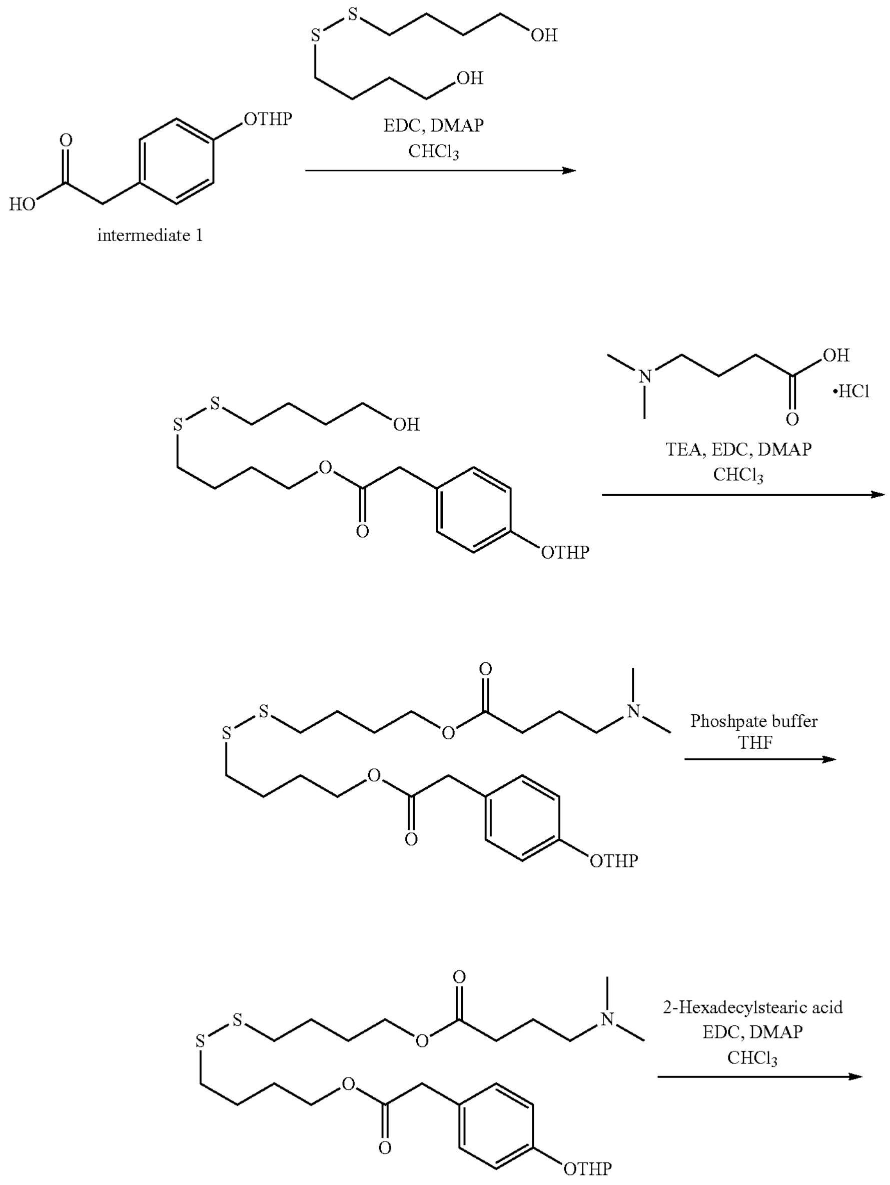

-continued

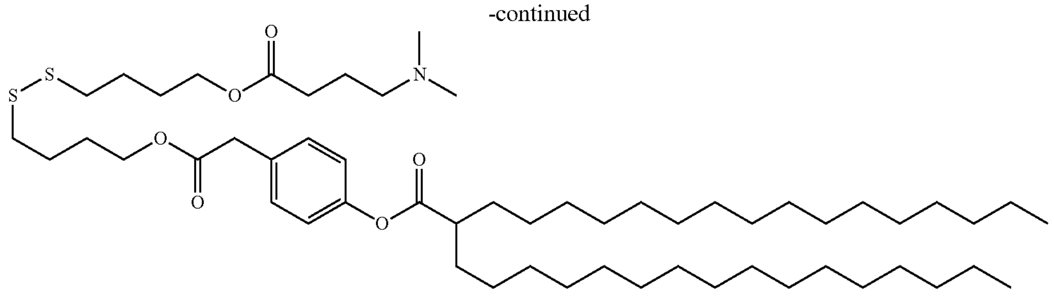

compound 41

[Example 41] Synthesis of Compound 41

Synthesis of Compound 41

By a synthesis route similar to that in Example 1 except that intermediate 1, 4,4'-dithiobisbutan-1-ol and 4-(dimethylamino)butanoic acid hydrochloride were used as starting materials, compound 41 was synthesized.

$^1$H-NMR (600 MHz, $CDCl_3$) of Compound 41

δ:0.88 (t, 6H), 1.20-1.50 (m, 64H), 1.69-1.84 (m, 4H), 2.21 (s, 6H), 2.28 (t, 2H), 2.35 (t, 2H), 2.52-2.59 (m, 1H), 2.59-2.70 (m, 4H), 3.63 (s, 2H), 4.22-4.33 (m, 4H), 7.02-7.05 (m, 2H), 7.27-7.30 (m, 2H)

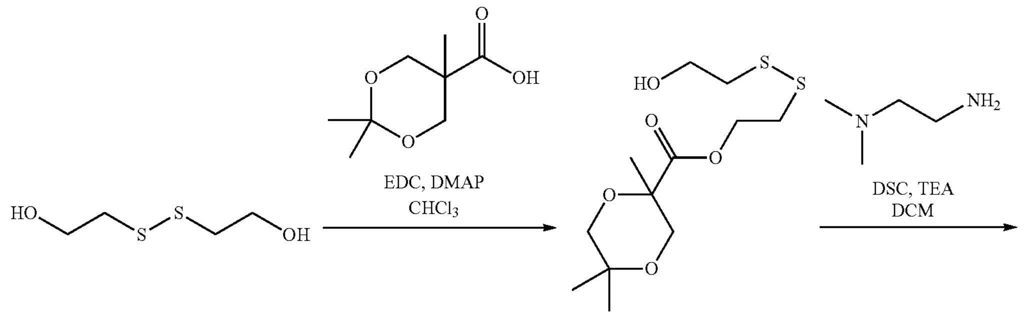

intermediate 32

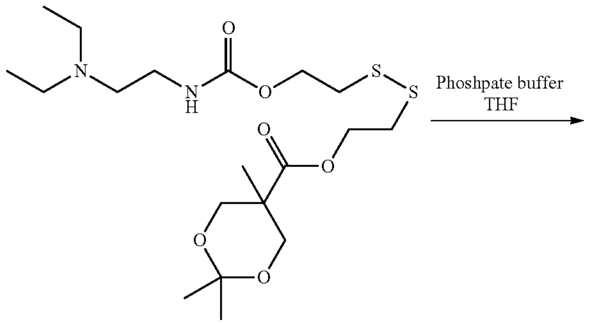

intermediate 33

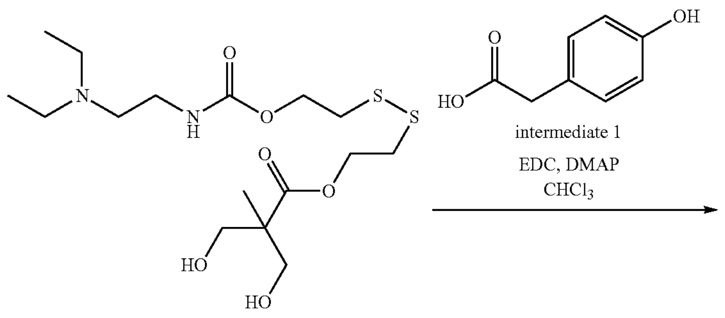

intermediate 34

-continued
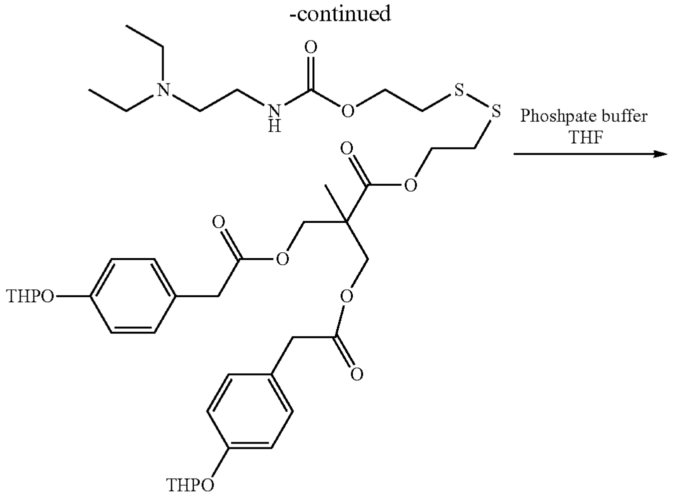
intermediate 35
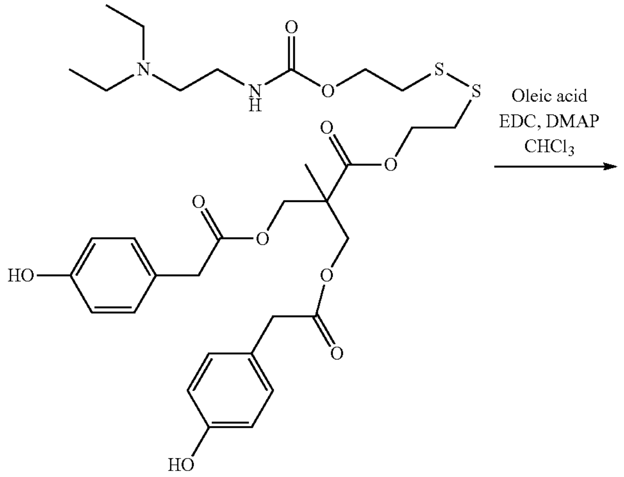
intermediate 36
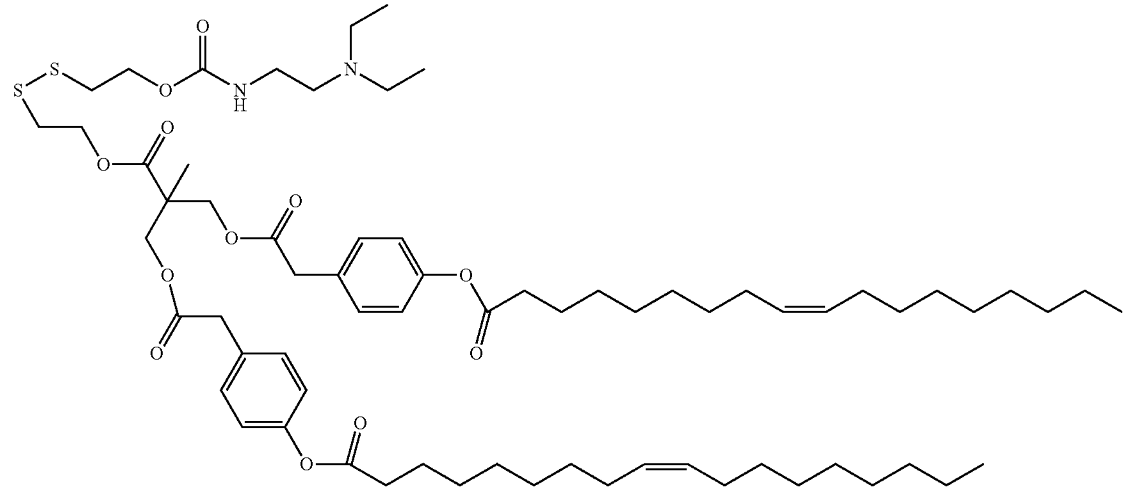
compound 42

[Example 42] Synthesis of Compound 42

Synthesis of Intermediate 32

Bis(2-hydroxyethyl) disulfide (33.2 g), 2,2,5-trimethyl-1,3-dioxane-5-carboxylic acid (25.0 g) and DMAP (3.50 g) were dissolved in 250 g of chloroform at room temperature. EDC (41.0 g) was added to the obtained solution and the mixture was reacted at 25° C. for 2 hr. The reaction solution was washed with 9.0 mL of 20 wt % brine, and then dehydrated by adding 25.0 g of sodium sulfate. After removing the sodium sulfate by filtration, the filtrate was concentrated in an evaporator and purified with a column to obtain 21.8 g of Intermediate 32.

Synthesis of Intermediate 33

180 g of dichloromethane was added to intermediate 32 (10.0 g) and triethylamine (7.17 g) and dissolved at room temperature. DSC (16.5 g) was added to the obtained solution and the mixture was reacted at 25° C. for 2 hr. After removing the DSC remaining in the reaction solution by filtration, N,N-diethylethylenediamine (5.00 g) was added to the filtrate and the mixture was reacted at 25° C. for 1 hr. After the reaction, the solution was washed with 150 g of 0.5 M acetate buffer (pH 4.0), 150 g of 7 wt % sodium bicarbonate water, and 150 g of 20 wt % brine, in that order, and then 5.00 g of sodium sulfate was added for dehydration. After removing the sodium sulfate by filtration, the filtrate was concentrated in an evaporator to obtain 13.1 g of intermediate 33.

Synthesis of Intermediate 34

Intermediate 33 (13.0 g) was dissolved in 49.0 g of THF, and then 195 g of 0.5 M phosphate buffer (pH 2.0) was added and the mixture was reacted at 40° C. for 3 hr. 120 g of chloroform was added to the reaction solution for washing. After washing, 400 g/L aqueous sodium hydroxide solution was added to the aqueous layer, and the pH was adjusted to 7.0, and the aqueous layer was extracted with 195 g of chloroform. 6.50 g of sodium sulfate was added to the extracted organic layer for dehydration, and sodium sulfate was removed by filtration. The filtrate was concentrated in an evaporator to obtain 5.01 g of intermediate 34.

Synthesis of Intermediate 35

Intermediate 34 (5.00 g), intermediate 1 (6.01 g) and DMAP (592 mg) were dissolved in 75.0 g of chloroform at room temperature. EDC (5.81 g) was added to the obtained solution and the mixture was reacted at 25° C. for 2 hr. The reaction solution was washed with 50.0 g of 20 wt % brine, and then 2.50 g of sodium sulfate was added for dehydration. After removing the sodium sulfate by filtration, the filtrate was concentrated in an evaporator to obtain 6.25 g of a crude product of intermediate 35.

Synthesis of Intermediate 36

6.25 g of the crude product of intermediate 35 was dissolved in 56.3 g of THF, and then 225 g of 0.5 M phosphate buffer (pH 2.0) was added and the mixture was reacted at 25° C. for 2 hr. 94.0 g of chloroform was added to the reaction solution for washing. After washing, 400 g/L aqueous sodium hydroxide solution was added to the aqueous layer, and the pH was adjusted to 6.0, and the aqueous layer was extracted with 94.0 g of chloroform. 3.00 g of sodium sulfate was added to the extracted organic layer to dehydrate it, and sodium sulfate was removed by filtration. The filtrate was concentrated in an evaporator to obtain 3.7 g of intermediate 36.

Synthesis of Compound 42

Intermediate 36 (500 mg), oleic acid (436 mg) and DMAP (36.0 mg) were dissolved in 7.50 g of chloroform at room temperature. EDC (352 mg) was added to the obtained solution and the mixture was reacted at 25° C. for 2 hr. The reaction solution was washed with 5.00 g of 20 wt % brine, and then dehydrated by adding 250 mg of sodium sulfate. After removing the sodium sulfate by filtration, the filtrate was concentrated in an evaporator and purified with a column to obtain 453 mg of compound 42.

$^1$H-NMR (600 MHz, $CDCl_3$) of Compound 42

δ:0.88 (t, 6H), 1.04 (t, 6H), 1.25-1.38 (m, 40H), 1.42 (s, 3H), 1.55-1.65 (m, 4H), 1.99-2.05 (m, 8H), 2.36 (t, 4H), 2.52-2.58 (m, 6H), 2.92-2.96 (m, 4H), 3.22-3.26 (m, 2H), 3.66 (s, 4H), 4.30-4.40 (m, 8H), 5.32-5.38 (m, 5H), 7.02-7.05 (m, 4H), 7.27-7.30 (m, 4H)

[Example 43] Synthesis of Compound 43

Synthesis of Compound 43

Using intermediate 36 and myristic acid, compound 43 was synthesized by the same synthetic route as in Example 42.

$^1$H-NMR (600 MHz, $CDCl_3$) of Compound 43

δ:0.89 (t, 6H), 1.04 (t, 6H), 1.25-1.35 (m, 40H), 1.42 (s, 3H), 1.55-1.65 (m, 4H), 2.36 (t, 4H), 2.52-2.58 (m, 6H), 2.92-2.96 (m, 4H), 3.22-3.26 (m, 2H), 3.66 (s, 4H), 4.30-4.40 (m, 8H), 5.32 (s, 1H), 7.02-7.05 (m, 4H), 7.27-7.30 (m, 4H)

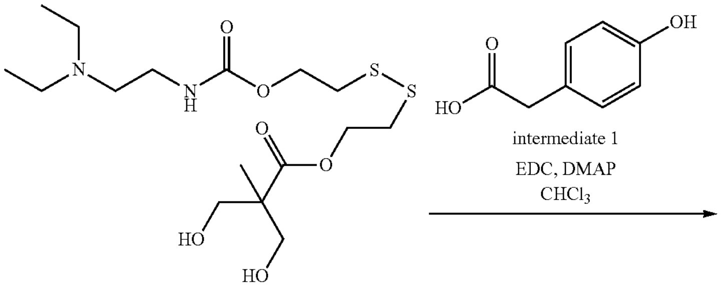

intermediate 34

-continued
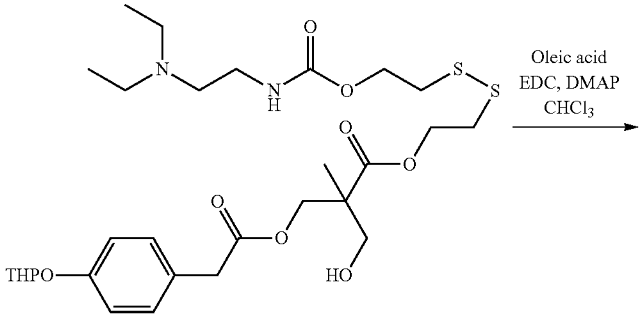
intermediate 37
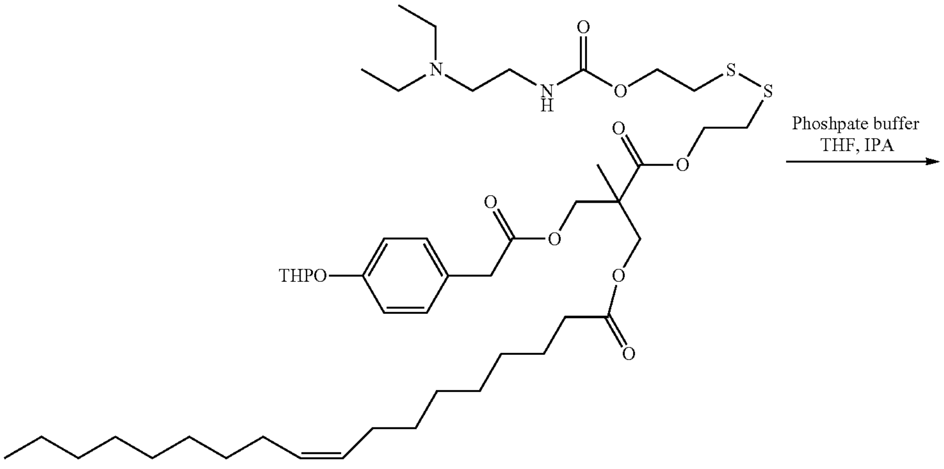
intermediate 38
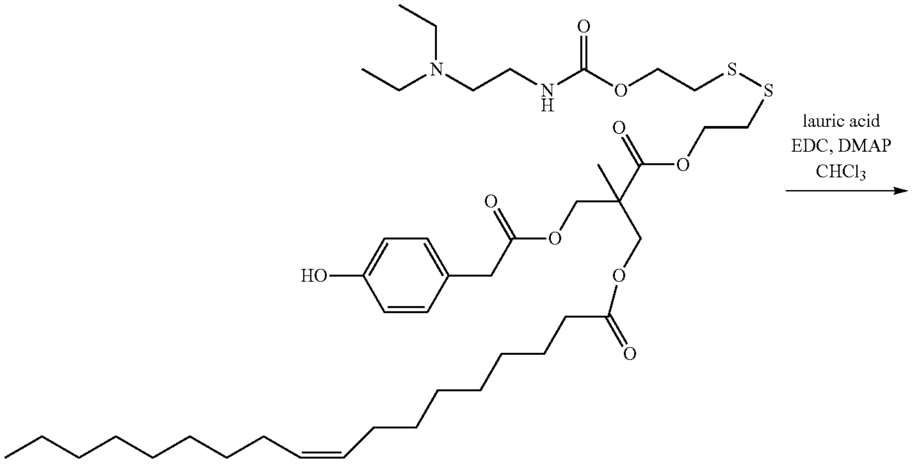
intermediate 39

-continued

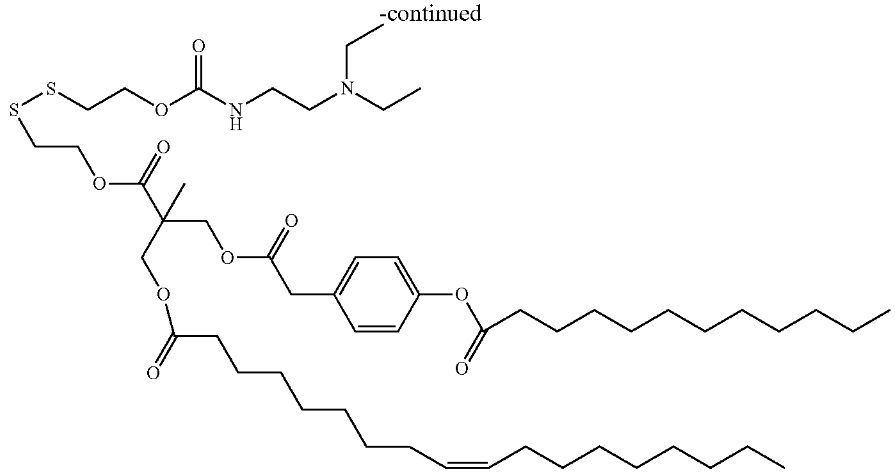

compound 44

[Example 44] Synthesis of Compound 44

Synthesis of Intermediate 37

Intermediate 34 (1.60 g), intermediate 1 (4.19 g) and DMAP (165 mg) were dissolved in 24.0 g of chloroform at room temperature. EDC (1.95 g) was added to the obtained solution and the mixture was reacted at 25° C. for 2 hr. The reaction solution was washed with 16.0 g of 20 wt % brine, and then 500 mg of sodium sulfate was added for dehydration. After removing the sodium sulfate by filtration, the filtrate was concentrated in an evaporator and purified with a column to obtain 1.85 g of intermediate 37.

Synthesis of Intermediate 38

Intermediate 37 (450 mg), oleic acid (241 mg) and DMAP (19.0 mg) were dissolved in 6.75 g of chloroform at room temperature. EDC (223 mg) was added to the obtained solution and the mixture was reacted at 25° C. for 2 hr. The reaction solution was washed with 4.5 g of 20 wt % brine, and then 2.0 g of sodium sulfate was added for dehydration. After removing the sodium sulfate by filtration, the filtrate was concentrated in an evaporator to obtain 670 mg of a crude product of intermediate 38.

Synthesis of Intermediate 39

The crude product of intermediate 38 (670 mg) was dissolved in a mixed solvent of 4.00 g THF and 4.00 g IPA, and then 16.2 g of 0.5 M phosphate buffer (pH 2.0) was added and the mixture was reacted at 40° C. for 3 hr. After adding 13.5 g of chloroform to the reaction solution for extraction, the organic layer was washed with 9.00 g of 0.5 M phosphate buffer (pH 6.5). After washing, 300 mg of sodium sulfate was added to the organic layer for dehydration, and sodium sulfate was removed by filtration. The filtrate was concentrated in an evaporator and purified with a column to obtain 240 mg of intermediate 39.

Synthesis of Compound 44

Intermediate 39 (150 mg), lauric acid (41.0 mg) and DMAP (5.0 mg) were dissolved in 2.25 g of chloroform at room temperature. EDC (53.0 mg) was added to the obtained solution and the mixture was reacted at 25° C. for 2 hr. The reaction solution was washed with 1.50 g of 20 wt % brine, and then 50.0 mg of sodium sulfate was added for dehydration. After removing the sodium sulfate by filtration, the filtrate was concentrated in an evaporator and purified with a column to obtain 116 mg of compound 44.

$^1$H-NMR (600 MHz, $CDCl_3$) of Compound 44

δ:0.80-0.92 (m, 6H), 1.04 (t, 6H), 1.25-1.38 (m, 36H), 1.42 (s, 3H), 1.55-1.65 (m, 4H), 1.99-2.05 (m, 4H), 2.36 (t, 2H), 2.52-2.58 (m, 6H), 2.92-2.96 (m, 4H), 3.22-3.26 (m, 2H), 3.66 (s, 4H), 4.30-4.40 (m, 8H), 5.32-5.36 (m, 3H), 7.02-7.05 (m, 2H), 7.27-7.30 (m, 2H)

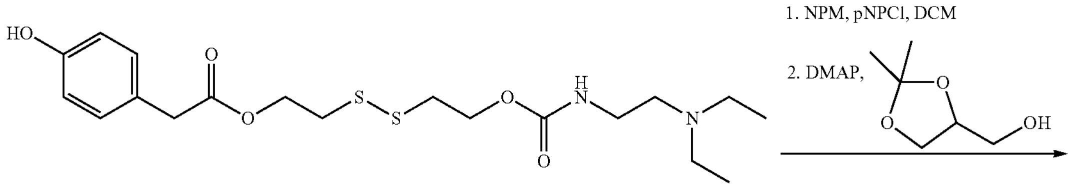

intermediate 18-b

-continued

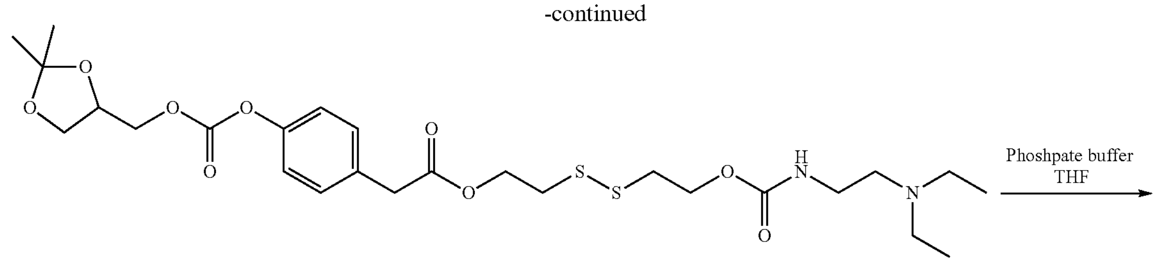

intermediate 40

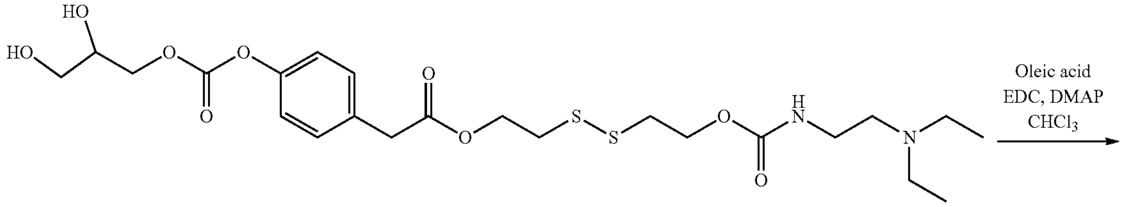

intermediate 41

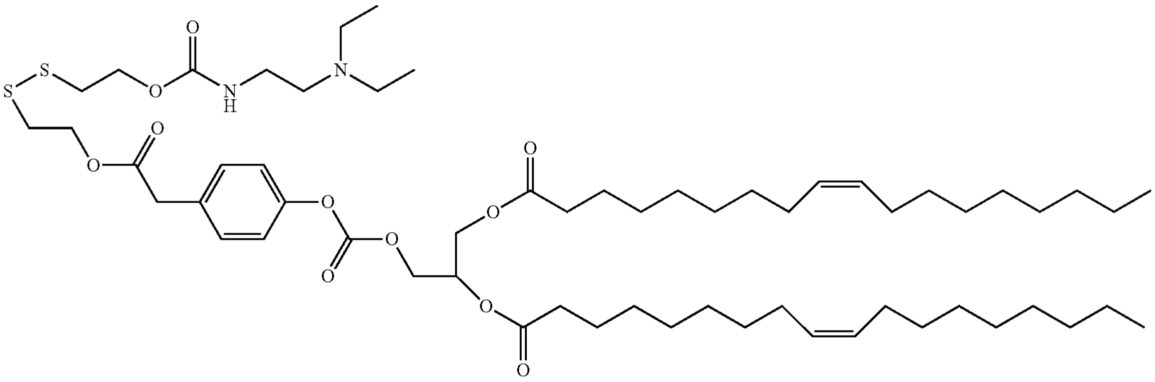

compound 45

[Example 45] Synthesis of Compound 45

Synthesis of Intermediate 40

Intermediate 18-b (3.00 g) and NPM (3.41 g) were added with 30.0 g of dichloromethane and dissolved at room temperature. pNPCl (3.51 g) was added to the obtained solution and the mixture was reacted at 25° C. for 10 hr. DMAP (170 mg) and 1,2-isopropylidene glycol (7.37 g) were added to this reaction solution and reacted at 25° C. for 8 hr. The reaction solution was washed with 30.0 g of 7 wt % sodium bicarbonate water and 30.0 g of 20 wt % brine in that order, and then 9.00 g of sodium sulfate was added for dehydration. After removing the sodium sulfate by filtration, the filtrate was concentrated in an evaporator and purified with a column to obtain 2.16 g of intermediate 40.

Synthesis of Intermediate 41

Intermediate 40 (2.16 g) was dissolved in 11.3 g of THF, and then 45.0 g of 0.5 M phosphate buffer (pH 2.0) was added and the mixture was reacted at 40° C. for 2 hr. 19.0 g of chloroform was added to the reaction solution for washing. After washing, 400 g/L aqueous sodium hydroxide solution was added to the aqueous layer, and the pH was adjusted to 6.0, and the aqueous layer was extracted with 19.0 g of chloroform. 1.20 g of sodium sulfate was added to the extracted organic layer to dehydrate it, and sodium sulfate was removed by filtration. The filtrate was concentrated using an evaporator to obtain 850 mg of intermediate 41.

Synthesis of Compound 45

By a synthesis route similar to that in Example 42 except that intermediate 41 and oleic acid were used, compound 45 was synthesized.

$^1$H-NMR (600 MHz, $CDCl_3$) of Compound 45

δ:0.89 (t, 6H), 1.04 (t, 6H), 1.25-1.38 (m, 40H), 1.42 (s, 3H), 1.55-1.65 (m, 4H), 1.99-2.05 (m, 8H), 2.36 (t, 4H), 2.52-2.58 (m, 6H), 2.92-2.96 (m, 4H), 3.22-3.26 (m, 2H), 3.66 (s, 2H), 4.30-4.50 (m, 8H), 5.28-5.38 (m, 6H), 6.97-7.00 (m, 2H), 7.27-7.30 (m, 2H)

[Example 46] Synthesis of Compound 46

Synthesis of Compound 46

By a synthesis route similar to that in Example 42 except that intermediate 41 and myristic acid were used, compound 46 was synthesized.

$^1$H-NMR (600 MHz, $CDCl_3$) of Compound 46

δ:0.89 (t, 6H), 1.04 (t, 6H), 1.25-1.35 (m, 32H), 1.42 (s, 3H), 1.55-1.65 (m, 4H), 2.36 (t, 4H), 2.52-2.58 (m, 6H), 2.92-2.96 (m, 4H), 3.22-3.26 (m, 2H), 3.66 (s, 2H), 4.30-4.50 (m, 8H), 5.28-5.31 (m, 2H), 6.97-7.00 (m, 2H), 7.27-7.30 (m, 2H)

[Comparative Example] Synthesis of O-Ph-P4C2

The title compound was synthesized by the synthesis route described in Example 3 of Patent Literature 3.

$^1$H-NMR (600 MHz, $CDCl_3$) of O-Ph-P4C2

δ0.88 (t, 6H), 1.22-1.42 (m, 46H), 1.54-1.76 (m, 12H), 1.94-2.03 (m, 12H), 2.52-2.56 (m, 4H), 2.62-2.66 (m, 4H), 2.80-2.89 (m, 8H), 3.59 (s, 4H), 4.13 (t, 4H), 5.34-5.37 (m, 4H), 7.02-7.05 (m, 4H), 7.27-7.30 (m, 4H)

[Experimental Example 1] Measurement of Liposomal pKa

Lipid nanoparticles (LNP) without containing nucleic acid were used for the evaluation of Liposomal pKa.

1. Preparation of LNP by Micro Flow Path (1) Preparation of Ethanol Solution of Lipid A 10 mM ethanol solution of cationic lipid, a 5 mM ethanol solution of DOPC, and a 10 mM ethanol solution of Chol were mixed at desired ratio (cationic lipid:DOPC:Chol=52.5:7.5:40 (molar ratio)) in an Eppendorf tube to achieve the total lipid amount of 720 nmol. To the obtained mixture was further added DMG-PEG2k (2 mM ethanol solution) in an amount of about 1.5 mol with respect to the total amount 100 mol of cationic lipid, DOPC, and Chol, and then ethanol was added to prepare an ethanol solution of the lipid (total amount: 360 μL).

(2) Preparation of LNP Using Micro Flow Path

An acidic malic acid buffer (20 mM, pH 3.0) (1080 μL) containing NaCl at a final concentration of 30 mM and an ethanol solution (360 μL) of lipid were each weighed in a syringe. Using an ultra high-speed nanomedicament producing apparatus NanoAssmblr (manufactured by Precision NanoSystems), LNP was prepared under the conditions of addition rate of acidic buffer solution: 3 mL/min, addition rate of ethanol solution of lipid: 1 mL/min, and syringe holder temperature: 25° C., and collected in a 15 mL tube. MES buffer (pH 6.5) (3000 μL) was added to the 15 mL tube, the obtained mixture was transferred to Amicon Ultra 4, and ultrafiltration was performed under centrifugation conditions (25° C., 1000 g, 6 min) to concentrate the mixture to about 100 μL. The obtained concentrate was diluted with PBS to 4 mL, and the mixture was concentrated again under centrifugation conditions (25° C., 1000 g, 6 min), and this operation was performed twice. The obtained concentrate was diluted with PBS to a lipid concentration of 0.5 mM to give a dispersion containing LNP.

2. Measurement of Liposomal pKa 20 mM Citrate buffer, sodium phosphate buffer, and tris HCl buffer, each containing NaCl at a final concentration of 150 mM and adjusted to various pHs within the range of pH 3.0 to 10.0, were prepared. TNS (manufactured by Sigma) was diluted with ultrapure water to 0.6 mM. TNS solution (2 μL), dispersions (12 μL) containing LNP prepared in [Experimental Example 1], 1., and buffers adjusted to various pHs (186 μL) were added to a black 96 well plate. The plate was protected from light and shaken at 400 rpm for 10 min. The fluorescence intensity (excitation: 321 nm/emission: 447 nm) was measured using a plate reader (manufactured by TECAN). The relative fluorescence intensity was calculated as a percentage, with the maximum value of the fluorescence intensity in each LNP being 100% and the minimum value being 0%. Furthermore, the pH at which the relative fluorescence intensity was 50% was taken as Liposomal pKa. The Liposomal pKa of respective LNPs are shown in Table 4. In Comparative Example, the cationic lipid described in the aforementioned Table 3 were used.

TABLE 4

| cationic lipid used to form LNP (Example No.) | Liposomal pKa |
|---|---|
| 1 | 5.7 |
| 2 | 5.7 |
| 4 | 7.8 |
| 5 | 7.8 |
| 7 | 7.8 |
| 8 | 7.8 |
| 9 | 7.8 |
| 10 | 7.4 |
| 11 | 7.0 |
| 12 | 6.2 |
| 13 | 6.3 |
| 15 | 6.3 |
| 16 | 6.4 |
| 17 | 6.2 |
| 18 | 6.8 |
| 19 | 8.2 |
| 20 | 8.8 |
| 21 | 7.9 |
| 22 | 7.5 |
| 23 | 8.3 |
| 24 | 8.2 |
| 25 | 8.6 |
| 26 | 5.7 |
| 27 | 5.7 |
| 28 | 6.7 |
| 29 | 6.7 |
| 30 | 6.4 |
| 31 | 7.6 |
| 32 | 7.2 |
| 33 | 7.1 |
| 34 | 7.2 |
| 35 | 6.8 |
| 36 | 7.3 |
| 42 | 7.3 |
| Comparative Example | 6.3 |

3. Results

All LNPs showed Liposomal pKa within the pKa range (5.0 to 9.5) preferable for endosomal escape.

[Experimental Example 2] Preparation of mRNA-Encapsulating Particles and Property Evaluation 1. Preparation of LNP by Micro Flow Path Method (1) Preparation of Ethanol Solution of Lipid A 10 mM ethanol solution of cationic lipid, a 5 mM ethanol solution of DOPC, and a 10 mM ethanol solution of Chol were mixed at desired ratio (cationic lipid:DOPC:Chol=55:5:40 (molar ratio)) in an Eppendorf tube to achieve the total lipid amount of 720 nmol. To the obtained mixture was further added DMG-PEG2k (2 mM ethanol solution) in an amount of about 1 mol with respect to the total amount 100 mol of cationic lipid, DOPC, and Chol, and then ethanol was added to prepare an ethanol solution of the lipid (total amount: 360 μL).

(2) Preparation of Acidic Buffer Solution of Nucleic Acid

An acidic buffer solution (total amount: 1080 μL) of nucleic acid was prepared by weighing 7.2 μg of mRNA solution (0.6 mg/mL) in a 5 mL tube and adding acidic malate buffer (20 mM, pH 3.0) containing NaCl at a final concentration of 30 mM.

(3) Preparation of LNP Using Micro Flow Path

An acidic buffer solution of nucleic acid and an ethanol solution of lipid were each weighed in a syringe. Using an ultra high-speed nanomedicament producing apparatus NanoAssmblr (manufactured by Precision NanoSystems), LNP was prepared under the conditions of addition rate of acidic buffer solution of nucleic acid: 3 mL/min, addition rate of ethanol solution of lipid: 1 mL/min, and syringe holder temperature: 25° C., and collected in a 15 mL tube. MES buffer (pH 6.5) (3000 μL) was added to the 15 mL tube, the obtained mixture was transferred to Amicon Ultra 4, and ultrafiltration was performed under centrifugation conditions (25° C., 1000 g, 6 min) to concentrate the mixture to about 100 μL. The obtained concentrate was diluted with PBS to 4 mL, and the mixture was concentrated again under centrifugation conditions (25° C., 1000 g, 6 min), and this operation was performed twice. The obtained concentrate was diluted with PBS to a lipid concentration of 2 mM to give a dispersion containing LNP.

2. Measurement of Particle Size, PdI and Zeta Potential of mRNA-Encapsulating LNPs The particle size, PdI (Polydispersity Index), and zeta potential of the mRNA-encapsulating LNP prepared by the method of the above-mentioned 1 were measured by a dynamic light scattering method. The results are shown in Table 5. In Comparative Example, the cationic lipid described in the aforementioned Table 3 were used.

TABLE 5

| Example No. | particle size (nm) | PdI | zeta potential (mV) |
|---|---|---|---|
| 1 | 82 | 0.072 | −3.4 |
| 2 | 84 | 0.072 | −2.9 |
| 3 | 90 | 0.078 | −3.0 |
| 4 | 64 | 0.116 | 12.2 |
| 5 | 74 | 0.081 | −2.9 |
| 7 | 92 | 0.077 | 6.8 |
| 8 | 72 | 0.101 | 5.3 |
| 9 | 96 | 0.168 | 12.1 |
| 10 | 80 | 0.077 | 4.9 |
| 11 | 86 | 0.079 | −0.9 |
| 12 | 84 | 0.071 | −4.4 |
| 13 | 94 | 0.086 | −10.2 |
| 14 | 67 | 0.071 | −4.1 |
| 15 | 65 | 0.112 | 6.0 |
| 16 | 97 | 0.067 | −2.5 |
| 17 | 105 | 0.064 | −2.6 |
| 18 | 105 | 0.132 | 5.3 |
| 19 | 73 | 0.121 | 13.1 |
| 21 | 116 | 0.118 | 6.4 |
| 22 | 96 | 0.090 | 4.7 |
| 23 | 94 | 0.160 | 13.8 |
| 24 | 96 | 0.109 | 12.2 |
| 25 | 78 | 0.126 | 14.7 |
| 28 | 66 | 0.070 | −1.4 |
| 29 | 59 | 0.080 | 1.2 |
| 30 | 59 | 0.080 | 2.3 |
| 31 | 59 | 0.072 | 4.1 |
| 34 | 63 | 0.060 | 0.4 |
| 35 | 70 | 0.068 | −4.0 |
| 36 | 92 | 0.090 | −2.5 |
| 38 | 106 | 0.106 | −3.8 |
| 39 | 107 | 0.128 | −5.3 |

TABLE 5-continued

| Example No. | particle size (nm) | PdI | zeta potential (mV) |
|---|---|---|---|
| 40 | 89 | 0.104 | 0.1 |
| 41 | 80 | 0.091 | 4.0 |
| Comparative Example | 73 | 0.064 | −1.5 |

3. Results

All of the mRNA-encapsulated LNPs had a particle size of 30 to 300 nm, which is in a preferred form, and the charge (zeta potential) at physiological pH was also in the preferred range (−15 to +15 mV).

[Experimental Example 3] Evaluation of In Vitro Gene Expression in HeLa Cell

1. Preparation of mRNA-Encapsulating LNP

LNP encapsulating mRNA that expresses luciferase (cationic lipid:DOPC:Chol:DMG-PEG2k=55:5:40:1 (molar ratio)) was prepared by the method described in [Experimental Example 2], 1.

2. Time-Course Evaluation of Gene Expression in HeLa Cells

HeLa cells, which are human cervical cancer cells, were seeded in a 3.5 cm dish at $5.0\times10^4$ cells/2 mL/Dish 24 hours before transfection. After 24 hours, the medium was exchanged with a culture medium (D-MEM) containing 0.1 mM D-luciferin. Prepared mRNA-encapsulating LNP was diluted with PBS such that the concentration of mRNA was about 8 μg/mL. The diluted mRNA-encapsulating LNP solution (about 50 μL, mRNA: 0.4 μg) was added to the 3.5 cm dish and set in an incubator luminometer KronosDio. The luminescence intensity of luciferase was measured for 2 min every one hour. The cumulative luciferase luminescence intensity for 24 hr was calculated from the obtained time change of expression. The results are shown in Table 6. "E+0a" (a: integer) indicated in Table 6 means "10a". For example, "1.0E+06" means "$1.0\times10^6$". In Comparative Example, the cationic lipid described in the aforementioned Table 3 were used.

TABLE 6

| Example No. | cumulative luciferase luminescence intensity over 24 hr (RLU) | relative value based on Comparative Example |
|---|---|---|
| 4 | 3.09E+05 | 0.03 |
| 5 | 2.15E+08 | 19.4 |
| 7 | 2.13E+08 | 19.2 |
| 8 | 2.83E+08 | 25.5 |
| 9 | 1.25E+08 | 11.3 |
| 10 | 1.90E+08 | 17.1 |
| 11 | 6.71E+07 | 6.06 |
| 12 | 1.13E+05 | 0.01 |
| 13 | 1.44E+05 | 0.01 |
| 15 | 8.22E+07 | 7.43 |
| 17 | 8.39E+04 | <0.01 |
| 18 | 3.99E+06 | 0.36 |
| 19 | 2.55E+07 | 2.30 |
| 21 | 1.22E+08 | 11.0 |
| 22 | 2.38E+08 | 21.5 |
| 23 | 2.05E+07 | 1.85 |

TABLE 6-continued

| Example No. | cumulative luciferase luminescence intensity over 24 hr (RLU) | relative value based on Comparative Example |
|---|---|---|
| 24 | 6.22E+07 | 5.62 |
| 25 | 1.25E+07 | 1.13 |
| 26 | 3.29E+05 | 0.03 |
| 27 | 9.60E+05 | 0.09 |
| 28 | 4.57E+07 | 4.13 |
| 29 | 1.75E+07 | 1.58 |
| 30 | 1.35E+07 | 1.22 |
| 31 | 1.58E+08 | 14.2 |
| 32 | 8.77E+07 | 7.92 |
| 33 | 5.38E+06 | 0.49 |
| 34 | 1.08E+08 | 9.72 |
| 35 | 6.34E+07 | 5.72 |
| 36 | 7.66E+07 | 6.91 |
| 38 | 1.31E+05 | 0.01 |
| 39 | 3.95E+04 | <0.01 |
| 40 | 2.33E+05 | 0.02 |
| 42 | 3.62E+07 | 3.27 |
| Comparative Example | 1.11E+07 | 1.00 |

3. Results

As shown in Table 6, the LNP containing cationic of Example 5, 7, 8, 9, 10, 11, 15, 19, 21, 22, 23, 24, 25, 28, 29, 30, 31, 32, 34, 35, 36, or 42 showed superior gene expression activity compared to Comparative Example. Therefore, it has become clear that the LNP containing cationic lipid of Example 5, 7, 8, 9, 10, 11, 15, 19, 21, 22, 23, 24, 25, 28, 29, 30, 31, 32, 34, 35, 36, or 42 is beneficial as an LNP capable of promoting the expression of mRNA.

[Experimental Example 4] Evaluation of In Vivo Gene Expression

1. Preparation of mRNA-Encapsulating LNP

LNP encapsulating mRNA that expresses luciferase (cationic lipid:DOPC:Chol:DMG-PEG2k=55:5:40:1 (molar ratio)) was prepared by the method described in [Experimental Example 2], 1.

2. Evaluation of In Vivo Gene Expression

The prepared each mRNA-encapsulating LNP dispersion was administered from the tail vein of BALB/c mouse (male, 5-week-old). The dose of mRNA was set to 0.05 mg per 1 kg body weight of the mouse, and the dose of the mRNA-encapsulating LNP dispersion was set to 10 μL per 1 g body weight of the mouse. After 4.5 hr from the administration of the mRNA-encapsulating LNP dispersion, a PBS solution of D-luciferin potassium was administered into the abdominal cavity of the mouse. The dose of D-luciferin potassium was set to 3 mg per mouse, and the dose of the PBS solution of D-luciferin potassium was set to 200 μL per mouse. After 15 min from the administration of the PBS solution of D-luciferin potassium, the mouse was euthanized, and the liver, spleen, kidney, heart, and lung were isolated. The luminescence in each organ was quantified using an in vivo imaging system (IVIS) with an exposure of 10 sec. The amount of luminescence in each organ was quantified by image analysis using Live Imaging software attached to IVIS. The amount of luminescence (photons/sec) was calculated from the acquired image and used as an index of gene expression activity. The results are shown in Table 7 and Table 8. "E+0a" (a: integer) indicated in Table 7 and Table 8 means "$10^a$". For example, "1.0E+02" means "$1.0\times10^2$". In Comparative Example, the cationic lipid described in the aforementioned Table 3 were used.

TABLE 7

| Example | amount of luminescence in each organ (photons/sec) | | | | |
|---|---|---|---|---|---|
| No. | liver | heart | spleen | kidney | lung |
| 7 | 1.23E+06 | 6.86E+05 | 4.03E+06 | 6.35E+05 | 8.28E+05 |
| 13 | 5.00E+07 | 1.00E+06 | 2.00E+06 | 8.00E+05 | 8.67E+05 |
| 20 | 4.95E+05 | 6.26E+05 | 5.18E+05 | 4.34E+05 | 3.68E+05 |
| 21 | 3.68E+05 | 3.41E+05 | 5.86E+05 | 5.83E+05 | 6.51E+05 |
| 22 | 8.31E+06 | 3.91E+05 | 3.16E+06 | 4.45E+05 | 5.20E+05 |
| 23 | 2.36E+05 | 1.00E−03 | 4.45E+05 | 1.53E+05 | 5.02E+05 |
| 24 | 5.08E+05 | 4.78E+05 | 5.09E+05 | 4.84E+05 | 5.58E+05 |
| 25 | 1.67E+05 | 4.74E+05 | 3.07E+05 | 3.63E+05 | 2.74E+05 |
| 28 | 9.90E+07 | 6.88E+05 | 1.68E+06 | 6.48E+05 | 9.12E+05 |
| 29 | 8.05E+07 | 7.27E+05 | 3.16E+06 | 6.29E+05 | 7.49E+05 |
| 30 | 1.98E+07 | 6.17E+05 | 1.24E+06 | 3.80E+05 | 5.26E+05 |
| 31 | 2.62E+07 | 7.26E+05 | 1.88E+07 | 5.53E+05 | 9.16E+05 |
| 34 | 2.52E+07 | 6.83E+05 | 1.37E+07 | 5.04E+05 | 6.02E+05 |
| 35 | 1.35E+07 | 6.31E+05 | 4.03E+06 | 3.94E+05 | 4.65E+05 |
| 36 | 2.33E+06 | 9.67E+05 | 2.00E+06 | 6.33E+05 | 8.67E+05 |

TABLE 8

| Example No. | amount of luminescence in spleen (photons/sec) | relative value based on Comparative Example |
|---|---|---|
| 7 | 4.03E+06 | 0.37 |
| 13 | 2.00E+06 | 0.19 |
| 20 | 5.18E+05 | 0.05 |
| 21 | 5.86E+05 | 0.05 |
| 22 | 3.16E+06 | 0.29 |
| 23 | 4.45E+05 | 0.04 |
| 24 | 5.09E+05 | 0.05 |
| 25 | 3.07E+05 | 0.03 |
| 28 | 1.68E+06 | 0.16 |
| 29 | 3.16E+06 | 0.29 |
| 30 | 1.24E+06 | 0.12 |
| 31 | 1.88E+07 | 1.74 |
| 34 | 1.37E+07 | 1.27 |
| 35 | 4.03E+06 | 0.37 |
| 36 | 2.00E+06 | 0.19 |
| Comparative Example | 1.08E+07 | 1.00 |

3. Results

As shown in Table 8, the LNP containing cationic lipid of Example 31 or 34 showed superior gene expression activity in particularly the spleen, compared to Comparative Example. Therefore, it was clarified that the LNP containing cationic lipid of Example 31 or 34 is beneficial as an LNP capable of promoting the expression of mRNA.

INDUSTRIAL APPLICABILITY

The cationic lipid of the present invention is useful for nucleic acid medicaments, gene therapy, biochemical experiments, and the like.

This application is based on patent application No. 2022-051912 filed in Japan, the contents of which are encompassed in full herein.

The invention claimed is:

1. A cationic lipid having a disulfide bond represented by the formula (1):

$$X—(R^1—L^1)_k—R^x—S—S—R^y—L^2—R^2—Y \quad (1)$$

wherein

X is a nitrogen-containing aliphatic group containing one or more tertiary nitrogens, $R^1$ is an aliphatic hydrocarbon group having not more than 8 carbon atoms, $L^1$ is an ester bond, an amide bond, a carbamate bond, an N-alkylcarbamate bond, a carbonate bond or a urea bond, k is 0 or 1, $R^x$ and $R^y$ are each independently an alkylene group having 2-5 carbon atoms, $L^2$ is an ester bond, an amide bond, a carbamate bond, a carbonate bond, an ether bond or a urea bond, $R^2$ is an alkylene group having not more than 8 carbon atoms, or absent, and Y is a group which (i) contains one or more divalent groups derived from an aromatic compound optionally having a hetero atom, (ii) contains a group containing at least one selected from the group consisting of an ester bond and a carbonate bond on the aromatic ring of the divalent group, and (iii) contains at least one selected from the group consisting of an aliphatic hydrocarbon group having 10-37 carbon atoms, a liposoluble vitamin residue, and a residue of a sterol derivative.

2. The cationic lipid having a disulfide bond according to claim 1, wherein

X is a group represented by the formula (2):

$$R^{\alpha}—N(R^{\beta})— \quad (2)$$

wherein $R^{\alpha}$ is an aliphatic hydrocarbon group, and $R^{\beta}$ is an aliphatic hydrocarbon group, an aliphatic group containing one or more hetero atoms other than nitrogen, or an aliphatic group containing one or more tertiary amines, or $R^{\alpha}$ and $R^{\beta}$ are optionally bonded to form a 3- to 8-membered nitrogen-containing alicyclic ring.

3. The cationic lipid having a disulfide bond according to claim 1, wherein

X is a dialkylamino group (wherein the two alkyl groups of the dialkylamino group each independently have 1 to 8 carbon atoms), a 3- to 6-membered cyclic amino group optionally having a hetero atom, or $—N(R^a)—R^b$, $R^a$ is an alkyl group having 1-8 carbon atoms, $R^b$ is $—(CH_2)q-O—R^c$, $R^c$ is a hydrogen or an alkyl group having 1-8 carbon atoms, and q is an integer of 2 to 4.

4. The cationic lipid having a disulfide bond according to claim 1, wherein $R^1$ is an alkylene group having not more than 8 carbon atoms, or an alkenylene group having not more than 8 carbon atoms.

5. The cationic lipid having a disulfide bond according to claim 1, wherein

Y is a group represented by the formula (3):

(3)

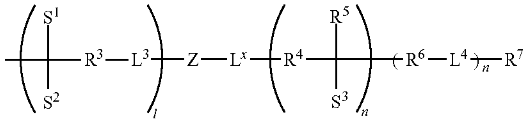

wherein $R^3$ is an alkylene group having not more than 8 carbon atoms, $L^3$ is an ester bond or a carbonate bond, $S^1$ is a hydrogen, an alkyl group having 1-8 carbon atoms, $—R^e-L^a-R^{7\prime}$, or $—R^e-L^a-Z'-L^b-R^{7\prime}$, $S^2$ is $—R^{e\prime}-L^a-R^{7\prime\prime}$ or $—R^{e\prime}-L^a-Z''-L^b-R^{7\prime\prime}$, $R^e$ and $R^{e\prime}$ are each independently an alkylene group having not more than 8 carbon atoms, $L^a$ is an ester bond or a carbonate bond, $L^b$ is an ester bond or a carbonate bond, l is 0 or 1, Z, Z' and Z" are each independently a divalent group derived from an aromatic compound having 3-16 carbon atoms and at least one aromatic ring, and optionally having a hetero atom, $L^x$ is an ester bond or a carbonate bond, $R^4$ is an alkylene group having not more than 8 carbon atoms, or absent, $R^5$ is a hydrogen or an alkyl group having 1-8 carbon atoms, $S^3$ is $—R^{6\prime}-L^{4\prime}-R^{7\prime\prime\prime}$, m is 0 or 1, $R^6$ and $R^{6\prime}$ are each independently an alkylene group having not more than 8 carbon atoms, or absent, $L^4$ and $L^{4\prime}$ are each independently an ester bond or a carbonate bond, $R^7$, $R^{7\prime}$, $R^{7\prime\prime}$ and $R^{7\prime\prime\prime}$ are each independently an aliphatic hydrocarbon group having 10-37 carbon atoms, or $—(CH_2)p-C(═O)—R^f$, $R^f$ is a residue of a liposoluble vitamin having a hydroxyl group or a residue of a sterol derivative having a hydroxyl group, and p is 2 or 3, and n is 0 or 1.

6. The cationic lipid having a disulfide bond according to claim 5, wherein

Z, Z' and Z" are each a group represented by the formula (4):

(4)

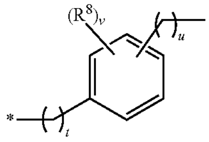

wherein t is an integer of 0 to 3, u is an integer of 0 to 3, v is an integer of 0 to 4, and $R^8$ in the number of v are each independently a substituent, and

* is the bonding position with $L^3$ or $L^a$.

7. The cationic lipid having a disulfide bond according to claim 1, wherein $R^x$ and $R^y$ are each an ethylene group.

8. The cationic lipid having a disulfide bond according to claim 5, wherein $R^7$, $R^{7'}$, $R^{7''}$ and $R^{7'''}$ are each independently an aliphatic hydrocarbon group having 10 to 37 carbon atoms, or $—(CH_2)_2—C(═O)—R^f$, and $R^f$ is a residue of a liposoluble vitamin having a hydroxyl group.

9. A lipid membrane structure comprising the cationic lipid having a disulfide bond according to claim 1 as a constituent lipid of a membrane.

10. A lipid membrane structure comprising the cationic lipid having a disulfide bond according to claim 1 as a constituent lipid of a membrane, and further comprising a nucleic acid.

11. A nucleic acid-introducing agent comprising the cationic lipid having a disulfide bond according to claim 1.

12. A pharmaceutical composition comprising the cationic lipid having a disulfide bond according to claim 1.

13. A method for introducing a nucleic acid into a cell in vitro, comprising bringing the nucleic acid-introducing agent according to claim 11 into contact with the cell, wherein the nucleic acid is encapsulated in the nucleic acid-introducing agent.

14. A method for introducing a nucleic acid into a target cell, comprising administering the nucleic acid-introducing agent according to claim 11 to a living organism to allow for delivery of the nucleic acid to the target cell, wherein the nucleic acid is encapsulated in the nucleic acid-introducing agent.

15. A method for producing a cell medicine comprising a cell expressing a specific gene, comprising contacting a cell with the nucleic acid-introducing agent according to claim 11 encapsulating a nucleic acid, and introducing the nucleic acid into the cell.

16. A nucleic acid-introducing agent comprising the lipid membrane structure according to claim 10.

17. A pharmaceutical composition comprising the lipid membrane structure according to claim 10.

18. A method for introducing a nucleic acid into a cell in vitro, comprising bringing the nucleic acid-introducing agent according to claim 16 into contact with the cell, wherein the nucleic acid is encapsulated in the nucleic acid-introducing agent.

19. A method for introducing a nucleic acid into a target cell, comprising administering the nucleic acid-introducing agent according to claim 16 to a living organism to allow for delivery of the nucleic acid to the target cell, wherein the nucleic acid is encapsulated in the nucleic acid-introducing agent.

20. A method for producing a cell medicine comprising a cell expressing a specific gene, comprising contacting a cell with the nucleic acid-introducing agent according to claim 16 encapsulating a nucleic acid, and introducing the nucleic acid into the cell.

* * * * *